(12) United States Patent
Cadaval et al.

(10) Patent No.: US 8,296,073 B2
(45) Date of Patent: Oct. 23, 2012

(54) DIAGNOSTIC METHOD

(75) Inventors: Ainara Cadaval, Derio (ES); Diego Tejedor Hernández, Derio (ES); Antonio Martínez Martínez, Derio (ES); Laureano Simón Buela, Derio (ES)

(73) Assignees: Progenika Biopharma, S.A., Barcelona (ES); Bioiberica, S.A., Barcelona (ES)

( * ) Notice: Subject to any disclaimer, the term of this patent is extended or adjusted under 35 U.S.C. 154(b) by 482 days.

(21) Appl. No.: 12/309,162

(22) PCT Filed: Jul. 12, 2007

(86) PCT No.: PCT/IB2007/002363
§ 371 (c)(1),
(2), (4) Date: Nov. 30, 2009

(87) PCT Pub. No.: WO2008/010083
PCT Pub. Date: Jan. 24, 2008

(65) Prior Publication Data
US 2010/0069334 A1    Mar. 18, 2010

(30) Foreign Application Priority Data

Jul. 12, 2006 (GB) .................................. 0613843.2
Nov. 24, 2006 (GB) .................................. 0623502.2

(51) Int. Cl.
*G06F 7/00* (2006.01)
(52) U.S. Cl. ................ 702/19; 702/20; 703/11; 707/700
(58) Field of Classification Search ........................ None
See application file for complete search history.

(56) References Cited

U.S. PATENT DOCUMENTS

2006/0057612 A1    3/2006  Styrkarsdottir et al.
2009/0299645 A1*  12/2009  Colby et al. .................... 702/19

FOREIGN PATENT DOCUMENTS

| WO | WO 97/27321    | 7/1997  |
| WO | WO 00/15836    | 3/2000  |
| WO | WO 03/066903   | 8/2003  |
| WO | WO 2004/046381 | 6/2004  |
| WO | WO 2004/097044 | 11/2004 |

OTHER PUBLICATIONS

Notification of Decision on Protest, PCT Application No. PCT/IB2007/002363, May 11, 2010.
Gennari et al., "Estrogen Receptor Gene Polymorphisms and the Genetics of Osteoporosis: A HuGE Review," *American Journal of Epidemiology*, vol. 161, No. 4, pp. 307-320, 2005.
Hosoi et al., "Association Study of Parathyroid Hormone Gene Polymorphism and Bone Mineral Density in Japanese Postmenopausal Women," *Calcif. Tissue Int.*, vol. 64, pp. 205-208, 1999.
Ioannidis et al., "Differential Genetic Effects of ESR1 Gene Polymorphisms on Osteoporosis Outcomes," *JAMA*, vol. 292 No. 17, pp. 2105-2114, 2004.
Katsumata et al., "Association of gene polymorphisms and bone density in Japanese girls," *J. Bone Miner. Metab.*, vol. 20, pp. 164-169, 2002.
Kobayashi et al., "Association of Bone Mineral Density with Polymorphism of the Estrogen Receptor Gene," *Journal of Bone and Mineral Research*, vol. 11, No. 3, pp. 306-311, 1996.
Shields et al., "DraII and XmnI polymorphisms at the human parathyroid hormone locus," *Nucleic Acid Research*, vol. 19, No. 15, p. 4312, 1992.

* cited by examiner

*Primary Examiner* — Mary Zeman
(74) *Attorney, Agent, or Firm* — Klarquist Sparkman, LLP.

(57) ABSTRACT

A method for prognosing osteoporosis phenotypes or estimating osteoporosis quantitative traits comprising determining outcomes for selected SNP variables and clinical variables. Products and methods for genotyping multiple osteoporosis associated genetic variations.

12 Claims, 65 Drawing Sheets

Figure 1A

Table 1A: Genetic variations associated with osteoporosis

The polymorphisms T27823C, A60890G, C61970T in the gene VDR.

The polymorphisms IVS1-397T/C, IVS1-351 G/A in the gene ESR1 and A1082G, G1730A in the gene ESR2.

The polymorphisms G84848C, T124843C, A36673G, A114758G in the gene CYP19.

The polymorphism G1240T in the gene Col1A1.

The polymorphisms A19994C, C14599T, in the gene Col1A2.

The polymorphisms A98G, G252A, C462A, in the gene PTH.

The polymorphisms T78536C, A59894G, G119895A, G119962A, C5276T, A20149G, G29008A, C29263T, in the gene LRP5.

The polymorphisms G-22018A, C-13910T, in the gene LCT.

The polymorphism T518C in the gene CYP17.

The polymorphism C4887A, in the gene CYP1A1.

The polymorphism A986S in the gene CaSR.

The polymorphism G1733A in the gene AR.

The polymorphism G-174C in the gene IL-6.

The polymorphisms G-511T, C3954T in the gene IL-1b.

The polymorphisms C-509T, C329T in the gene TGF-B1.

The polymorphism G-1082A in the gene IL-10.

The polymorphism C1377T, T1340C in the gene CTR.

The polymorphisms A163G, T245G, T950C, G1181C, A6890C in the gene OPG.

The polymorphisms G-308A, G489A, in the gene TNFalfa..

The polymorphism C677T in the gene MTHFR.

The polymorphism G158A in the gene COMT.

The polymorphism A9598T in the gene IL-1Ra.

The polymorphism T676G in the gene TNFR2.

The polymorphisms A49T, A89T, in the gene SRD5A2.

The polymorphism Leu162Val in the gene Ppar alpha.

The polymorphism Glu496Ala (A1539C), in the gene P2X7Receptor.

The polymorphisms Arg16Gly, Gln27Glu, Thr164Ile, -367T/C, -42 T/C in the gene ADRB2.

The polymorphisms Ser49Gly, Gly389Arg, in the gene ADRB1.

The polymorphism Trp64Arg in the gene ADRB3.

The polymorphism V192A, in the gene RANK (TNFRSF11A).

The polymorphisms G-1752A, G-1699A, Glu254Lys, in the gene ALOX5
The polymorphism G-366A in the gene ALOX5AP.
The polymorphisms Gln261Arg, Ser322Asn in the gene ALOX12.
The polymorphisms Leu237Met, Val481Ile, in the gene COX1.
The polymorphisms C-645T, Val511Ala, in the gene COX2.
The polymorphism C787T in the gene ALPL.
The polymorphism Ile1062Val in the gene LRP6.
The polymorphism T176C in the gene Integrin B3.
The polymorphisms A>G(UTR), V418M, Silent A390A, C>T Intron, Silent P42P, in the gene CLCN7.
The polymorphism A>G (5'UTR) in the gene RANKL.
The polymorphism Pro12Ala in the gene PPARG.
The polymorphisms G395A, C1818T, in the gene KL.
The polymorphisms C52813T, A58250G, T60162C, T61407C, in the gene PTHR1.
The polymorphism Ser37Ala in he gene BMP2.
The polymorphism C1294G in the gene CYP1B1.
The polymorphism C266T in the gene IGF-II.
The polymorphism G11988A in the gene SOST.
The polymorphism C-1563T in the BNP gene.
The polymorphism A>C in the gene FDPS.
The polymorphism –5826 G>A, 3564 C>T in the gene BMP4.
The polymorphism A147G (ex 1) in the gene RUNX 2.
The polymorphism –5229 G>A in the gene ALOX15.
The polymorphism c1283G>C, IVS4 –6838 A/G, IVS5 +24C/T in the gene BMP6.
The polymorphism C-305T in the gene BMP9.
The polymorphism 681 C/G promoter in the gene PPAR g3.
The polymorphism C161T (ex.6) in the gene PPAR gamma.
The polymorphism -600 C/T, -545 C/T, Ala56Thre (ex1) G/A, A/G (int2), Tyr187His (ex3) in the gene MKP1.
The polymorphism –2322 A/G (5´flanking) in the gene OSCAR.
The polymorphism 5-2353A (promoter) in the gene POMC.

(...cont'd)

Figure 1B: Table 1B

| #SNP | Gene Symbol | Gene Name | |
|---|---|---|---|
| 1.00 | VDR | Vitamin D Receptor. VDR 2T/C | rs10735810 |
| 2.00 | VDR | Vitamin D Receptor. VDR (BsmI) | rs1544410 |
| 3.00 | VDR | Vitamin D Receptor. VDR (Taql) | rs731236 |
| 4.00 | ESR1 | Estrogen Receptor.ESR 1IVS1-397T/C | rs2234693 |
| 5.00 | ESR2 | Estrogen Receptor ESR 1IVS1-351 G/A | rs9340799 |
| 6.00 | ESR2 | Estrogen Receptor ESR 2 (Rsal) A1082G | rs1256049 |
| 7.00 | CYP19 | CytochromeP450 family 19CYP19 G>C. Rs1062033Posicion 84848 en AY957953 | rs1062033 |
| 8.00 | CYP19 | CytochromeP450 family 19 CYP19 (SfaNI). (probes to detect the polymorphismC/G of the geneCYP19 ) | rs700519 |
| 9.00 | CYP19 | CytochromeP450 family 19 CYP19 (SfaNI). (probes to detect the polymorphismC/T of the geneCYP19 ) | rs700519 |
| 10.00 | CYP19 | CytochromeP450 family 19 CYP19 | rs3784307 |
| 11.00 | CYP19 | CytochromeP450 family 19CYP19 | rs10046 |
| 12.00 | ColI1A1 | Collagen type 1A1 .ColIA1 | rs1800012 |
| 13.00 | ColI1A2 | Collagen type 1AColI1A2 (PvuII) | rs412777 |
| 14.00 | ColI1A2 | Collagen type 1AColI1A2 | rs17166249 |
| 15.00 | PTH | Parathyroid hormonePTH | rs694 |
| 16.00 | PTH | Parathyroid hormone PTH (BstBI) | rs6254 |
| 17.00 | PTH | Parathyroid hormone PTH (DraII) | rs6256 |
| 18.00 | LRP-5 | Low density lipoprotein receptor-related protein 5LRP5 (IVS4-4T/C) | rs314776 |
| 19.00 | LRP-5 | Low density lipoprotein receptor-related protein 5 LRP5 exon 9 | rs2277268 |
| 20.00 | LRP-5 | Low density lipoprotein receptor-related protein 5 LRP5 exon 9 | rs4988321 |
| 21.00 | LRP-5 | Low density lipoprotein receptor-related protein 5LRP5 exon10 | rs2306862 |
| 22.00 | LRP-5 | Low density lipoprotein receptor-related protein 5 LRP5 exon 15 | rs556442 |
| 23.00 | LRP-5 | Low density lipoprotein receptor-related protein 5LRP5EXON 18 | rs3736228 |
| 24.00 | LCT | LactaseLCT gene. G-22018A | rs182549 |
| 25.00 | LCT | LactaseLCTC-13910T | rs4988236 |
| 26.00 | CYP17 | CytochromeP450 family 17CYP17 | rs743572 |
| 27.00 | CaSR | Calcium-sensing receptorCaSR | rs1801725 |
| 28.00 | AR | Androgen Receptor | rs6152 |
| 29.00 | IL-6 | Interleukin-6IL-6 | rs1800795 |

Figure 1B (cont.)

| | | | | |
|---|---|---|---|---|
| 30.00 | IL-1b | Interleukin 1-betaIL-1b | | rs1799916 |
| 31.00 | IL-1b | Interleukin 1-betaIL-1b C3954T | | rs1143634 |
| 32.00 | TGF-B1 | Transforming growth factor B-1TGF-B1 (-509) | | rs1800469 |
| 33.00 | TGF-B1 | Transforming growth factor B-1TGF-B1 codon 10 | | rs17849267 |
| 34.00 | IL-10 | Interleukin-10IL-10 (G-1082A) | | rs1800896 |
| 35.00 | ESR2 | Estrogen receptor 2 (ER beta)ESR 2 (AluI) G1730G/A | | |
| 36.00 | LRP-5 | Low density lipoprotein receptor-related protein 5 LRP5 exon 2 | | |
| 37.00 | LRP-5 | Low density lipoprotein receptor-related protein 5 LPR5 (IVS17-30) | | rs1799814 |
| 38.00 | CYP1A1 | CytochromeP450, family 1CYP1A1 | | rs1801197 |
| 39.00 | CTR | Calcitonin receptorCTRLeu447Pro | | rs3102735 |
| 40.00 | OPG | OsteoprogeterinOPG A163G | | rs3134069 |
| 41.00 | OPG | OsteoprogeterinOPGT245G | | rs2073617 |
| 42.00 | OPG | OsteoprogeterinOPGT950C | | rs2073618 |
| 43.00 | OPG | OsteoprogeterinOPG G1181C | | rs7844539 |
| 44.00 | OPG | OsteoprogeterinOPG A6890C | | rs1800629 |
| 45.00 | TNFa | Tumor necrosis factor aTNFalfa (-308) | | rs1800610 |
| 46.00 | TNFa | Tumor necrosis factor a TNFalfa (+489) | | rs1801133 |
| 47.00 | MTHFR | Methylenetetrahydrofolate reductase MTHFR (+677) | | rs4680 |
| 48.00 | COMT | Catechol-O-methyltransferaseCOMT | | rs454078 |
| 49.00 | IL-1RA | Interleukin 1 receptor antagonistIL-1Ra (A9598T) | | |
| 50.00 | TNFR2 (TNFRSF1B) | Tumor necrosis factor beta receptorTNFR2 (TNFRSF1B) | | rs1061622 |
| 51.00 | SRD5A2 | Steroid-5-alpha-reductaseSRD5A2 (probes to detect the polymorphism G/A of the geneSRD5A2) | | rs9282858 |
| 52.00 | SRD5A2 | Steroid-5-alpha-reductaseSRD5A2 (probes to detect the polymorphism G/C of the geneSRD5A2) | | rs523349 |
| 53.00 | RUNX 2 | Runt-related transcription factor 2 RUNX2 | | rs6921145 |
| 54.00 | PPARA | Peroxisome proliferative activated receptor, gammaPpar alpha | | rs1800206 |
| 55.00 | P2X7Receptor | Purinergic receptorP2X, ligand-gated ion channel, 7P2X7Receptor (A139C)A>C.Posición 18337 de AC069209 | | rs3751143 |
| 56.00 | ADRB2 | Adrenergic receptor, beta 2 ADRB2 Arg16Gly | | rs1042713 |
| 57.00 | ADRB2 | Adrenergic receptor, beta 2 ADRB2Gln27Glu | | rs1042714 |
| 58.00 | ADRB1 | Adrenergic receptor, beta 1 ADRB1 Gly389Arg | | rs1801253 |
| 59.00 | ADRB2 | Adrenergic receptor, beta 2 ADRB2Thr164Ile | | rs1800888 |
| 60.00 | ADRB2 | Adrenergic receptor, beta 2 ADRB2 -42T/C | | rs1042711 |
| 61.00 | ADRB1 | Adrenergic receptor, beta 1 ADRB1Ser49Gly | | rs1801252 |

Figure 1B (cont.)

| | | | |
|---|---|---|---|
| 62.00 | ADRB3 | Adrenergic receptor, beta 3 ADRB3 | rs4994 |
| 63.00 | RANK (TNFRSF11A) | Tumor necrosis factor receptor superfamily, member 11a,NFKB activator RANK (TNFRSF11A) V192A | rs1805034 |
| 64.00 | ALOX5 | Arachidonate 5-lipoxygenase ALOX5 (-1752 G>A) | rs6413416 |
| 65.00 | ALOX5 | Arachidonate 5-lipoxygenase ALOX5 (-1699G>A) | rs4986832 |
| 66.00 | ALOX5AP | Arachidonate 5-lipoxygenase ALOX5 (Glu254Lys) | rs2228065 |
| 67.00 | ALOX12 | Arachidonate 12-lipoxygenase ALOX12 (gln261arg) | rs1126667 |
| 68.00 | ALOX12 | Arachidonate 12-lipoxygenase ALOX12 (Ser322Asn)) | rs434473 |
| 69.00 | COX1 (PTGS1) | Prostaglandin-endoperoxide synthase 1COX1 (PTGS1)Leu237met | rs5789 |
| 70.00 | COX1 (PTGS1) | Prostaglandin-endoperoxide synthase 1 COX1 (PTGS1) VA481Ile | rs5794 |
| 71.00 | COX2 (PTGS2) | Prostaglandin-endoperoxide synthase 2 COX2 (PTGS2) -645C/T | rs20420 |
| 72.00 | COX2 (PTGS2) | Prostaglandin-endoperoxide synthase 2 COX2 (PTGS2) Val511 Ala | rs5273 |
| 73.00 | LRP6 | Low density lipoprotein receptor-related protein 6LRP6 | rs2302685 |
| 74.00 | ITGB3 | Integrin, beta 3ITGB3(T176C) | rs5918 |
| 75.00 | CLCN7 | Chloride channel 7CLCN7 (UTR) | rs2294542 |
| 76.00 | CLCN7 | Chloride channel 7CLCN7 (V418M) | rs12926089 |
| 77.00 | CLCN7 | Chloride channel 7CLCN7 (Silent A390A) | rs2235579 |
| 78.00 | CLCN7 | Chloride channel 7CLCN7 (Intron) | rs2235580 |
| 79.00 | CLCN7 | Chloride channel 7CLCN7 (SilentP42P) | rs3751884 |
| 80.00 | RANK (TNFRSF11A) | Tumor necrosis factor (ligand) superfamily, member 11 RANKL (TNSF11) A>G | rs2277438 |
| 81.00 | PPARG | Peroxisome proliferative activated receptor, gammaPPARG | rs1805192 |
| 82.00 | KL | Klotho geneKL | rs1207568 |
| 83.00 | KL | Klotho geneKL | rs564481 |
| 84.00 | PTHR1 | Parathyroid hormone receptor 1PTHR1 | rs724449 |
| 85.00 | PTHR1 | Parathyroid hormone receptor 1PTHR1 | rs2242116 |
| 86.00 | PTHR1 | Parathyroid hormone receptor 1PTHR1 | rs1531137 |
| 87.00 | PTHR1 | Parathyroid hormone receptor 1PTHR1 | rs1869872 |
| 88.00 | BMP 2 | Bone morphogenetic protein 2 BMP2 (Ser37Ala) | rs2273073 |
| 89.00 | CYP1B1 | CytochromeP450, family 1, subfamily B, polypeptide 1CYP1B1 | rs1056836 |
| 90.00 | IGF-II | Insulin-like growth factor 2IGF-II | rs2230949 |
| 91.00 | SOST | Sclerosteosis SOST | rs17882143 |
| 92.00 | NPPB | Natriuretic peptide precursor BNPPB (BNP Gene) | |
| 93.00 | ADRB2 | Adrenergic, beta-2-, receptor, surface ADRB2 -367T/C | rs11959427 |

Figure 1B (cont.)

| | | | |
|---|---|---|---|
| 94.00 | TNSALP (ALPL) | Alkaline phosphatase, liver/bone/kidney TNSALP (ALPL) | rs3200254 |
| 95.00 | ALOX5AP | Arachidonate 5-lipoxygenase-activating protein ALOX5AP | rs9550373 |
| 96.00 | FDPS | Farnesyl diphosphate synthase FDPS | rs2297480 |
| 97.00 | ALOX15 | Arachidonate 15-lipoxygenase ALOX15 | rs748694 |
| 98.00 | BMP 4 | Bone morphogenetic protein 4  BMP4 (6007C/T) | rs17563 |
| 99.00 | BMP 4 | Bone morphogenetic protein 4  BMP4 (-5826 G/A) | rs1957860 |
| 100.00 | BMP 4 | Bone morphogenetic protein 4  BMP4 (3564C/T) | rs2855532 |
| 101.00 | CYP19 | CytochromeP450, family 19 , subfamily A, ARO1 (CYP19A1) (C/T) | rs4775936 |
| 102.00 | MKP1 | Mitogen-activatedprotein kinase (MAPK) familyMKP1 (C/T) | rs881152 |
| 103.00 | MKP1 | Mitogen-activatedprotein kinase (MAPK) familyMKP1 (C/T) | rs2070996 |
| 104.00 | MKP1 | Mitogen-activatedprotein kinase (MAPK) familyMKP1 Ala56Thre (G/A) | rs12521930 |
| 105.00 | MKP1 | Mitogen-activatedprotein kinase (MAPK) familyMKP1 (intron 2) (A/G) | rs7702178 |
| 106.00 | MKP1 | Mitogen-activatedprotein kinase (MAPK) familyMKP1ex3TyrHis (T/C) | desconocido |
| 107.00 | ESRRAL | Estrogen-related receptor alpha,ESRRA (I/D) | rs3217060 |
| 108.00 | PPARG | Peroxisome proliferative activated receptor, gammaPPARg3 (C/G) | rs10865710 |
| 109.00 | PPARG | Peroxisome proliferative activated receptor, gammaPPARg (C/T) | rs3856806 |
| 110.00 | POMC | ProopiomelanocortinPOMC –2353A (A/G) | rs3754863 |
| 111.00 | BMP6 | Bone morphogenetic protein 6  BMP6 IVS4 –6838 (A/G) | rs592849 |
| 112.00 | BMP6 | Bone morphogenetic protein 6  BMP6 IVS5 +24 (C/T) | |

Figure 2A: Table 2A

| #SNP | Gene Symbol | ID Number | Sequence |
|---|---|---|---|
| 1 | VDR | SEQ ID NO 221 | TCTTACAGGGACGGAGGCAATGG |
| | | SEQ ID NO 222 | TCTTACAGGGATGGAGGCAATGG |
| | | SEQ ID NO 223 | CCATTGCCTCCTTCCCTGTAAGA |
| | | SEQ ID NO 224 | CCATTGCCTCCATCCCTGTAAGA |
| 2 | VDR | SEQ ID NO 225 | GACAGGCCTGCGCATTCCCAATA |
| | | SEQ ID NO 226 | GACAGGCCTGCACATTCCCAATA |
| | | SEQ ID NO 227 | TATTGGGAATGCGCAGGCCTGTC |
| | | SEQ ID NO 228 | TATTGGGAATGTGCAGGCCTGTC |
| 3 | VDR | SEQ ID NO 229 | GCCGCGCTGATTGAGGCCATCCA |
| | | SEQ ID NO 230 | GCCGCGCTGATCGAGGCCATCCA |
| | | SEQ ID NO 231 | TGGATGGCCTCAATCAGCGCGGC |
| | | SEQ ID NO 232 | TGGATGGCCTCGATCAGCGCGGC |
| 4 | ESR1 | SEQ ID NO 233 | AATGTCCCAGCTGTTTTATGCTT |
| | | SEQ ID NO 234 | AATGTCCCAGCCGTTTTATGCTT |
| | | SEQ ID NO 235 | AAGCATAAAACAGCTGGGACATT |
| | | SEQ ID NO 236 | AAGCATAAAACGGCTGGGACATT |
| 5 | ESR2 | SEQ ID NO 237 | GAGTGTGGTCTAGAGTTGGGATG |
| | | SEQ ID NO 238 | GAGTGTGGTCTGGAGTTGGGATG |
| | | SEQ ID NO 239 | CATCCCAACTCTAGACCACACTC |
| | | SEQ ID NO 240 | CATCCCAACTCCAGACCACACTC |
| 6 | ESR2 | SEQ ID NO 241 | TTCGACCAAGTGCGGCTCTTGGA |
| | | SEQ ID NO 242 | TTCGACCAAGTACGGCTCTTGGA |
| | | SEQ ID NO 243 | TCCAAGAGCCGCACTTGGTCGAA |
| | | SEQ ID NO 244 | TCCAAGAGCCGTACTTGGTCGAA |
| 7 | CYP19 | SEQ ID NO 245 | AAGCTCCCTGAGTTCCCCGCCTG |
| | | SEQ ID NO 246 | AAGCTCCCTGACTTCCCCGCCTG |
| | | SEQ ID NO 247 | CAGGCGGGGAACTCAGGGAGCTT |
| | | SEQ ID NO 248 | CAGGCGGGGAAGTCAGGGAGCTT |
| 8 | CYP19 | SEQ ID NO 249 | CAGAAAAAAGACGCAGGATTTCC |
| | | SEQ ID NO 250 | CAGAAAAAAGAGGCAGGATTTCC |
| | | SEQ ID NO 251 | GGAAATCCTGCGTCTTTTTTCTG |
| | | SEQ ID NO 252 | GGAAATCCTGCCTCTTTTTTCTG |
| 9 | CYP19 | SEQ ID NO 253 | CAGAAAAAAGACGCAGGATTTCC |
| | | SEQ ID NO 254 | CAGAAAAAAGATGCAGGATTTCC |
| | | SEQ ID NO 255 | GGAAATCCTGCGTCTTTTTTCTG |
| | | SEQ ID NO 256 | GGAAATCCTGCATCTTTTTTCTG |
| 10 | CYP19 | SEQ ID NO 257 | TAGCATCACTGGATTGGAGTGGA |
| | | SEQ ID NO 258 | TAGCATCACTGAATTGGAGTGGA |
| | | SEQ ID NO 259 | TCCACTCCAATCCAGTGATGCTA |
| | | SEQ ID NO 260 | TCCACTCCAATTCAGTGATGCTA |
| 11 | CYP19 | SEQ ID NO 261 | TGGTCAGTACCCACTCTGGAGCA |
| | | SEQ ID NO 262 | TGGTCAGTACCTACTCTGGAGCA |
| | | SEQ ID NO 263 | TGCTCCAGAGTGGGTACTGACCA |
| | | SEQ ID NO 264 | TGCTCCAGAGTAGGTACTGACCA |
| 12 | CollA1 | SEQ ID NO 265 | CCCAGGGAATGGGGCGGGATGA |
| | | SEQ ID NO 266 | CCCAGGGAATGTGGGCGGGATGA |
| | | SEQ ID NO 267 | TCATCCCGCCCCCATTCCCTGGG |
| | | SEQ ID NO 268 | TCATCCCGCCCACATTCCCTGGG |

Figure 2A (cont.)

| | | | |
|---|---|---|---|
| 13 | Col1A2 | SEQ ID NO 269 | CCAATTGGCCCAGCTGGAGCAAG |
| | | SEQ ID NO 270 | CCAATTGGCCCCGCTGGAGCAAG |
| | | SEQ ID NO 271 | CTTGCTCCAGCTGGGCCAATTGG |
| | | SEQ ID NO 272 | CTTGCTCCAGCGGGGCCAATTGG |
| 14 | Col1A2 | SEQ ID NO 273 | TCACATAGAATCCTGGAAATTAA |
| | | SEQ ID NO 274 | TCACATAGAATTCTGGAAATTAA |
| | | SEQ ID NO 275 | TTAATTTCCAGGATTCTATGTGA |
| | | SEQ ID NO 276 | TTAATTTCCAGAATTCTATGTGA |
| 15 | PTH | SEQ ID NO 277 | CCATTTTGCTTGTCCTTTTAGTG |
| | | SEQ ID NO 278 | CCATTTTGCTTATCCTTTTAGTG |
| | | SEQ ID NO 279 | CACTAAAAGGACAAGCAAAATGG |
| | | SEQ ID NO 280 | CACTAAAAGGATAAGCAAAATGG |
| 16 | PTH | SEQ ID NO 281 | TTTATCATTTCGAAGTGGGGAGC |
| | | SEQ ID NO 282 | TTTATCATTTCAAAGTGGGGAGC |
| | | SEQ ID NO 283 | GCTCCCCACTTCGAAATGATAAA |
| | | SEQ ID NO 284 | GCTCCCCACTTTGAAATGATAAA |
| 17 | PTH | SEQ ID NO 285 | CCCAGAGGCCCCGAAAAAAGGAA |
| | | SEQ ID NO 286 | CCCAGAGGCCCAGAAAAAAGGAA |
| | | SEQ ID NO 287 | TTCCTTTTTTCGGGGCCTCTGGG |
| | | SEQ ID NO 288 | TTCCTTTTTTCTGGGCCTCTGGG |
| 18 | LRP-5 | SEQ ID NO 289 | TCCTGGTTTTCTCAGTCCACACT |
| | | SEQ ID NO 290 | TCCTGGTTTTCCCAGTCCACACT |
| | | SEQ ID NO 291 | AGTGTGGACTGAGAAAACCAGGA |
| | | SEQ ID NO 292 | AGTGTGGACTGGGAAAACCAGGA |
| 19 | LRP-5 | SEQ ID NO 293 | ACCAAGAAGGCGTCAGGCACGAT |
| | | SEQ ID NO 294 | ACCAAGAAGGCATCAGGCACGAT |
| | | SEQ ID NO 295 | ATCGTGCCTGACGCCTTCTTGGT |
| | | SEQ ID NO 296 | ATCGTGCCTGATGCCTTCTTGGT |
| 20 | LRP-5 | SEQ ID NO 297 | ATAACAACGACGTGGCCATCCCG |
| | | SEQ ID NO 298 | ATAACAACGACATGGCCATCCCG |
| | | SEQ ID NO 299 | CGGGATGGCCACGTCGTTGTTAT |
| | | SEQ ID NO 300 | CGGGATGGCCATGTCGTTGTTAT |
| 21 | LRP-5 | SEQ ID NO 301 | ACTGGGACCAACAGAATCGAAGT |
| | | SEQ ID NO 302 | ACTGGGACCAATAGAATCGAAGT |
| | | SEQ ID NO 303 | ACTTCGATTCTGTTGGTCCCAGT |
| | | SEQ ID NO 304 | ACTTCGATTCTATTGGTCCCAGT |
| 22 | LRP-5 | SEQ ID NO 305 | GCCCTGGTGGTAGACAACACACT |
| | | SEQ ID NO 306 | GCCCTGGTGGTGGACAACACACT |
| | | SEQ ID NO 307 | AGTGTGTTGTCTACCACCAGGGC |
| | | SEQ ID NO 308 | AGTGTGTTGTCCACCACCAGGGC |
| 23 | LRP-5 | SEQ ID NO 309 | CTCAGACGAGGCGGACTGTGACG |
| | | SEQ ID NO 310 | CTCAGACGAGGTGGACTGTGACG |
| | | SEQ ID NO 311 | CGTCACAGTCCGCCTCGTCTGAG |
| | | SEQ ID NO 312 | CGTCACAGTCCACCTCGTCTGAG |
| 24 | LCT | SEQ ID NO 313 | GTGAGCCACCGGGCCCAGCTGAG |
| | | SEQ ID NO 314 | GTGAGCCACCGGACCCAGCTGAG |
| | | SEQ ID NO 315 | CTCAGCTGGGCCCGGTGGCTCAC |
| | | SEQ ID NO 316 | CTCAGCTGGGCCTGGTGGCTCAC |
| 25 | LCT | SEQ ID NO 317 | ATAATGTAGCCCCTGGCCTCAAA |
| | | SEQ ID NO 318 | ATAATGTAGCCTCTGGCCTCAAA |
| | | SEQ ID NO 319 | TTTGAGGCCAGGGGCTACATTAT |

Figure 2A (cont.)

| | | SEQ ID NO 320 | TTTGAGGCCAGAGGCTACATTAT | |
|---|---|---|---|---|
| 26 | CYP17 | SEQ ID NO 321 | TTCTACTCCACTGCTGTCTATCT | |
| | | SEQ ID NO 322 | TTCTACTCCACCGCTGTCTATCT | |
| | | SEQ ID NO 323 | AGATAGACAGAAGTGGAGTAGAA | |
| | | SEQ ID NO 324 | AGATAGACAGGAGTGGAGTAGAA | |
| 27 | CaSR | SEQ ID NO 325 | CTCAGAAGAACGCCATGGCCCAC | |
| | | SEQ ID NO 326 | CTCAGAAGAACTCCATGGCCCAC | |
| | | SEQ ID NO 327 | GTGGGCCATGGCGTTCTTCTGAG | |
| | | SEQ ID NO 328 | GTGGGCCATGGAGTTCTTCTGAG | |
| 28 | AR | SEQ ID NO 329 | AGAGCGAGGGAGGCCTCGGGGGC | |
| | | SEQ ID NO 330 | AGAGCGAGGGAAGCCTCGGGGGC | |
| | | SEQ ID NO 331 | GCCCCCGAGGCCTCCCTCGCTCT | |
| | | SEQ ID NO 332 | GCCCCCGAGGCTTCCCTCGCTCT | |
| 29 | IL-6 | SEQ ID NO 333 | TTGTGTCTTGCGATGCTAAAGGA | |
| | | SEQ ID NO 334 | TTGTGTCTTGCCATGCTAAAGGA | |
| | | SEQ ID NO 335 | TCCTTTAGCATCGCAAGACACAA | |
| | | SEQ ID NO 336 | TCCTTTAGCATGGCAAGACACAA | |
| 30 | IL-1b | SEQ ID NO 337 | ACAGGCTGCTCTGGGATTCTCTT | |
| | | SEQ ID NO 338 | ACAGGCTGCTCGGGGATTCTCTT | |
| | | SEQ ID NO 339 | AAGAGAATCCCAGAGCAGCCTGT | |
| | | SEQ ID NO 340 | AAGAGAATCCCCGAGCAGCCTGT | |
| 31 | IL-1b | SEQ ID NO 341 | CCTATCTTCTTCGACACATGGGA | |
| | | SEQ ID NO 342 | CCTATCTTCTTTGACACATGGGA | |
| | | SEQ ID NO 343 | TCCCATGTGTCGAAGAAGATAGG | |
| | | SEQ ID NO 344 | TCCCATGTGTCAAAGAAGATAGG | |
| 32 | TGF-B1 | SEQ ID NO 345 | CCCTTCCATCCCTCAGGTGTCCT | |
| | | SEQ ID NO 346 | CCCTTCCATCCTTCAGGTGTCCT | |
| | | SEQ ID NO 347 | AGGACACCTGAGGGATGGAAGGG | |
| | | SEQ ID NO 348 | AGGACACCTGAAGGATGGAAGGG | |
| 33 | TGF-B1 | SEQ ID NO 349 | GTAGCAGCAGCAGCAGCAGCCGC | |
| | | SEQ ID NO 350 | GTAGCAGCAGCGGCAGCAGCCGC | |
| | | SEQ ID NO 351 | GCGGCTGCTGCTGCTGCTGCTAC | |
| | | SEQ ID NO 352 | GCGGCTGCTGCCGCTGCTGCTAC | |
| 34 | IL-10 | SEQ ID NO 353 | CTTCTTTGGGAGGGGGAAGTAGG | |
| | | SEQ ID NO 354 | CTTCTTTGGGAAGGGGAAGTAGG | |
| | | SEQ ID NO 355 | CCTACTTCCCCCAGGGTTTCTTC | |
| | | SEQ ID NO 356 | CCTACTTCCCCTAGGGTTTCTTC | |
| 35 | ESR2 | SEQ ID NO 357 | CAGAGGTCACAGGCTGAAGCGTG | |
| | | SEQ ID NO 358 | CAGAGGTCACAAGCTGAAGCGTG | |
| | | SEQ ID NO 359 | CACGCTTCAGCCTGTGACCTCTG | |
| | | SEQ ID NO 360 | CACGCTTCAGCTTGTGACCTCTG | |
| 36 | LRP-5 | SEQ ID NO 361 | GGCCATCAAGCAGACCTACCTGA | |
| | | SEQ ID NO 362 | GGCCATCAAGCGGACCTACCTGA | |
| | | SEQ ID NO 363 | TCAGGTAGGTCTGCTTGATGGCC | |
| | | SEQ ID NO 364 | TCAGGTAGGTCCGCTTGATGGCC | |
| 37 | LRP-5 | SEQ ID NO 365 | GGCGGGGCTGCGTGTGATGTTCT | |
| | | SEQ ID NO 366 | GGCGGGGCTGCATGTGATGTTCT | |
| | | SEQ ID NO 367 | AGAACATCACACGCAGCCCCGCC | |
| | | SEQ ID NO 368 | AGAACATCACATGCAGCCCCGCC | |
| 38 | CYP1A1 | SEQ ID NO 369 | TATCGGTGAGACCATTGCCCGCT | |
| | | SEQ ID NO 370 | TATCGGTGAGAACATTGCCCGCT | |

Figure 2A (cont.)

| | | SEQ ID NO 371 | AGCGGGCAATGGTCTCACCGATA | |
|---|---|---|---|---|
| | | SEQ ID NO 372 | AGCGGGCAATGTTCTCACCGATA | |
| 39 | CTR | SEQ ID NO 373 | CCATCAGGAGCTGAGGAATGAAC | |
| | | SEQ ID NO 374 | CCATCAGGAGCCGAGGAATGAAC | |
| | | SEQ ID NO 375 | GTTCATTCCTCAGCTCCTGATGG | |
| | | SEQ ID NO 376 | GTTCATTCCTCGGCTCCTGATGG | |
| 40 | OPG | SEQ ID NO 377 | GTCTCCCCCATAAATTCCCTGGT | |
| | | SEQ ID NO 378 | GTCTCCCCCATGAATTCCCTGGT | |
| | | SEQ ID NO 379 | ACCAGGGAATTTATGGGGGAGAC | |
| | | SEQ ID NO 380 | ACCAGGGAATTCATGGGGGAGAC | |
| 41 | OPG | SEQ ID NO 381 | ACTTCTGGAGTTGCCTCCTCGAG | |
| | | SEQ ID NO 382 | ACTTCTGGAGTGGCCTCCTCGAG | |
| | | SEQ ID NO 383 | CTCGAGGAGGCAACTCCAGAAGT | |
| | | SEQ ID NO 384 | CTCGAGGAGGCCACTCCAGAAGT | |
| 42 | OPG | SEQ ID NO 385 | GAAAGCGTTAATCCTGGAGCTTT | |
| | | SEQ ID NO 386 | GAAAGCGTTAACCCTGGAGCTTT | |
| | | SEQ ID NO 387 | AAAGCTCCAGGATTAACGCTTTC | |
| | | SEQ ID NO 388 | AAAGCTCCAGGGTTAACGCTTTC | |
| 43 | OPG | SEQ ID NO 389 | ACAATGAACAAGTTGCTGTGCTG | |
| | | SEQ ID NO 390 | ACAATGAACAACTTGCTGTGCTG | |
| | | SEQ ID NO 391 | CAGCACAGCAACTTGTTCATTGT | |
| | | SEQ ID NO 392 | CAGCACAGCAAGTTGTTCATTGT | |
| 44 | OPG | SEQ ID NO 393 | TTATTTTAGATAATCATACCTTG | |
| | | SEQ ID NO 394 | TTATTTTAGATCATCATACCTTG | |
| | | SEQ ID NO 395 | CAAGGTATGATTATCTAAAATAA | |
| | | SEQ ID NO 396 | CAAGGTATGATGATCTAAAATAA | |
| 45 | TNFa | SEQ ID NO 397 | TGAGGGGCATGGGGACGGGGTTC | |
| | | SEQ ID NO 398 | TGAGGGGCATGAGGACGGGGTTC | |
| | | SEQ ID NO 399 | GAACCCCGTCCCCATGCCCCTCA | |
| | | SEQ ID NO 400 | GAACCCCGTCCTCATGCCCCTCA | |
| 46 | TNFa | SEQ ID NO 401 | GAGAAAAAAACATGGAGAAAGAC | |
| | | SEQ ID NO 402 | GAGAAAAAAACGTGGAGAAAGAC | |
| | | SEQ ID NO 403 | GTCTTTCTCCATGTTTTTTTCTC | |
| | | SEQ ID NO 404 | GTCTTTCTCCACGTTTTTTTCTC | |
| 47 | MTHFR | SEQ ID NO 405 | GTCTGCGGGAGCCGATTTCATCA | |
| | | SEQ ID NO 406 | GTCTGCGGGAGTCGATTTCATCA | |
| | | SEQ ID NO 407 | TGATGAAATCGGCTCCCGCAGAC | |
| | | SEQ ID NO 408 | TGATGAAATCGACTCCCGCAGAC | |
| 48 | COMT | SEQ ID NO 409 | ATTTCGCTGGCGTGAAGGACAAG | |
| | | SEQ ID NO 410 | ATTTCGCTGGCATGAAGGACAAG | |
| | | SEQ ID NO 411 | CTTGTCCTTCACGCCAGCGAAAT | |
| | | SEQ ID NO 412 | CTTGTCCTTCATGCCAGCGAAAT | |
| 49 | IL-1RA | SEQ ID NO 413 | GAAACAACCAAAATTTTTTCTTA | |
| | | SEQ ID NO 414 | GAAACAACCAATATTTTTTCTTA | |
| | | SEQ ID NO 415 | TAAGAAAAAATTTTGGTTGTTTC | |
| | | SEQ ID NO 416 | TAAGAAAAAATATTGGTTGTTTC | |
| 50 | TNFR2 (TNFRSF1B) | SEQ ID NO 417 | GAATGCAAGCATGGATGCAGTCT | |
| | | SEQ ID NO 418 | GAATGCAAGCAGGGATGCAGTCT | |
| | | SEQ ID NO 419 | AGACTGCATCCATGCTTGCATTC | |
| | | SEQ ID NO 420 | AGACTGCATCCCTGCTTGCATTC | |

Figure 2A (cont.)

| | | | |
|---|---|---|---|
| 51 | SRD5A2 | SEQ ID NO 421 | CCCGCCTGCCAGCCCGCGCCGCC |
| | | SEQ ID NO 422 | CCCGCCTGCCAACCCGCGCCGCC |
| | | SEQ ID NO 423 | GGCGGCGCGGGCTGGCAGGCGGG |
| | | SEQ ID NO 424 | GGCGGCGCGGGTTGGCAGGCGGG |
| 52 | SRD5A2 | SEQ ID NO 425 | GCCTCTTCTGCGTACATTACTTC |
| | | SEQ ID NO 426 | GCCTCTTCTGCCTACATTACTTC |
| | | SEQ ID NO 427 | GAAGTAATGTACGCAGAAGAGGC |
| | | SEQ ID NO 428 | GAAGTAATGTAGGCAGAAGAGGC |
| 53 | RUNX 2 | SEQ ID NO 429 | GCTGCGGCGGCGGCGGCGGCTGC |
| | | SEQ ID NO 430 | GCTGCGGCGGCAGCGGCGGCTGC |
| | | SEQ ID NO 431 | GCAGCCGCCGCCGCCGCCGCAGC |
| | | SEQ ID NO 432 | GCAGCCGCCGCTGCCGCCGCAGC |
| 54 | PPARA | SEQ ID NO 433 | TTCACAAGTGCCTTTCTGTCGGG |
| | | SEQ ID NO 434 | TTCACAAGTGCGTTTCTGTCGGG |
| | | SEQ ID NO 435 | CCCGACAGAAAGGCACTTGTGAA |
| | | SEQ ID NO 436 | CCCGACAGAAACGCACTTGTGAA |
| 55 | P2X7Receptor | SEQ ID NO 437 | GGCAGCACAGCACCTCCAGGCAC |
| | | SEQ ID NO 438 | GGCAGCACAGCCCCTCCAGGCAC |
| | | SEQ ID NO 439 | GTGCCTGGAGGTGCTGTGCTGCC |
| | | SEQ ID NO 440 | GTGCCTGGAGGGGCTGTGCTGCC |
| 56 | ADRB2 | SEQ ID NO 441 | CTGGCACCCAATGGAAGCCATGCGC |
| | | SEQ ID NO 442 | CTGGCACCCAATAGAAGCCATGCGC |
| | | SEQ ID NO 443 | GCGCATGGCTTCCATTGGGTGCCAG |
| | | SEQ ID NO 444 | GCGCATGGCTTCTATTGGGTGCCAG |
| 57 | ADRB2 | SEQ ID NO 445 | GACGTCACGCAGCAAAGGGACGAGG |
| | | SEQ ID NO 446 | GACGTCACGCAGGAAAGGGACGAGG |
| | | SEQ ID NO 447 | CCTCGTCCCTTTGCTGCGTGACGTC |
| | | SEQ ID NO 448 | CCTCGTCCCTTTCCTGCGTGACGTC |
| 58 | ADRB1 | SEQ ID NO 449 | AGGCCTTCCAGCGACTGCTCTGC |
| | | SEQ ID NO 450 | AGGCCTTCCAGGGACTGCTCTGC |
| | | SEQ ID NO 451 | GCAGAGCAGTCGCTGGAAGGCCT |
| | | SEQ ID NO 452 | GCAGAGCAGTCCCTGGAAGGCCT |
| 59 | ADRB2 | SEQ ID NO 453 | GTCAGGCCTTACCTCCTTCTTGC |
| | | SEQ ID NO 454 | GTCAGGCCTTATCTCCTTCTTGC |
| | | SEQ ID NO 455 | GCAAGAAGGAGGTAAGGCCTGAC |
| | | SEQ ID NO 456 | GCAAGAAGGAGATAAGGCCTGAC |
| 60 | ADRB2 | SEQ ID NO 457 | GTGGGTCCGCCTGCTGAGGCGCC |
| | | SEQ ID NO 458 | GTGGGTCCGCCGGCTGAGGCGCC |
| | | SEQ ID NO 459 | GGCGCCTCAGCAGGCGGACCCAC |
| | | SEQ ID NO 460 | GGCGCCTCAGCCGGCGGACCCAC |
| 61 | ADRB1 | SEQ ID NO 461 | CCGCCAGCGAAAGCCCCGAGCCG |
| | | SEQ ID NO 462 | CCGCCAGCGAAGGCCCCGAGCCG |
| | | SEQ ID NO 463 | CGGCTCGGGGCTTTCGCTGGCGG |
| | | SEQ ID NO 464 | CGGCTCGGGGCCTTCGCTGGCGG |
| 62 | ADRB3 | SEQ ID NO 465 | TGGCCATCGCCTGGACTCCGAGA |
| | | SEQ ID NO 466 | TGGCCATCGCCCGGACTCCGAGA |
| | | SEQ ID NO 467 | TCTCGGAGTCCAGGCGATGGCCA |
| | | SEQ ID NO 468 | TCTCGGAGTCCGGGCGATGGCCA |
| 63 | RANK (TNFRSF11A) | SEQ ID NO 469 | GAAATCCGATGTGGTTTGCAGTT |
| | | SEQ ID NO 470 | GAAATCCGATGCGGTTTGCAGTT |

Figure 2A (cont.)

| | | SEQ ID NO 471 | AACTGCAAACCACATCGGATTTC | |
|---|---|---|---|---|
| | | SEQ ID NO 472 | AACTGCAAACCGCATCGGATTTC | |
| 64 | ALOX5 | SEQ ID NO 473 | AACTTACTATAGCACTGCGGTAA | |
| | | SEQ ID NO 474 | AACTTACTATAACACTGCGGTAA | |
| | | SEQ ID NO 475 | TTACCGCAGTGCTATAGTAAGTT | |
| | | SEQ ID NO 476 | TTACCGCAGTGTTATAGTAAGTT | |
| 65 | ALOX5 | SEQ ID NO 477 | ATTACAGATCAGTGGACTAGAAT | |
| | | SEQ ID NO 478 | ATTACAGATCAATGGACTAGAAT | |
| | | SEQ ID NO 479 | ATTCTAGTCCACTGATCTGTAAT | |
| | | SEQ ID NO 480 | ATTCTAGTCCATTGATCTGTAAT | |
| 66 | ALOX5AP | SEQ ID NO 481 | CAGAGCTGCCCGAGAAGCTCCCG | |
| | | SEQ ID NO 482 | CAGAGCTGCCCAAGAAGCTCCCG | |
| | | SEQ ID NO 483 | CGGGAGCTTCTCGGGCAGCTCTG | |
| | | SEQ ID NO 484 | CGGGAGCTTCTTGGGCAGCTCTG | |
| 67 | ALOX12 | SEQ ID NO 485 | GGAAGAGCTTCGGGCTCAACTGG | |
| | | SEQ ID NO 486 | GGAAGAGCTTCAGGCTCAACTGG | |
| | | SEQ ID NO 487 | CCAGTTGAGCCCGAAGCTCTTCC | |
| | | SEQ ID NO 488 | CCAGTTGAGCCTGAAGCTCTTCC | |
| 68 | ALOX12 | SEQ ID NO 489 | TCAGCCTCCCAACCCCAGCTCTC | |
| | | SEQ ID NO 490 | TCAGCCTCCCAGCCCCAGCTCTC | |
| | | SEQ ID NO 491 | GAGAGCTGGGGTTGGGAGGCTGA | |
| | | SEQ ID NO 492 | GAGAGCTGGGGCTGGGAGGCTGA | |
| 69 | COX1 (PTGS1) | SEQ ID NO 493 | ATGGAGACAATCTGGAGCGTCAG | |
| | | SEQ ID NO 494 | ATGGAGACAATCTGGAGCGTCAG | |
| | | SEQ ID NO 495 | CTGACGCTCCAGATTGTCTCCAT | |
| | | SEQ ID NO 496 | CTGACGCTCCAGATTGTCTCCAT | |
| 70 | COX1 (PTGS1) | SEQ ID NO 497 | TCCAGGAGCTCGTAGGTGAGCAG | |
| | | SEQ ID NO 498 | TCCAGGAGCTCATAGGTGAGCAG | |
| | | SEQ ID NO 499 | CTGCTCACCTACGAGCTCCTGGA | |
| | | SEQ ID NO 500 | CTGCTCACCTATGAGCTCCTGGA | |
| 71 | COX2 (PTGS2) | SEQ ID NO 501 | CCCCAGTCTGTCCCGACGTGACT | |
| | | SEQ ID NO 502 | CCCCAGTCTGTTCCGACGTGACT | |
| | | SEQ ID NO 503 | AGTCACGTCGGGACAGACTGGGG | |
| | | SEQ ID NO 504 | AGTCACGTCGGAACAGACTGGGG | |
| 72 | COX2 (PTGS2) | SEQ ID NO 505 | CATGGTAGAAGTTGGAGCACCAT | |
| | | SEQ ID NO 506 | CATGGTAGAAGCTGGAGCACCAT | |
| | | SEQ ID NO 507 | ATGGTGCTCCAACTTCTACCATG | |
| | | SEQ ID NO 508 | ATGGTGCTCCAGCTTCTACCATG | |
| 73 | LRP6 | SEQ ID NO 509 | GTTTACCACAATGGCTCGAGGTC | |
| | | SEQ ID NO 510 | GTTTACCACAACGGCTCGAGGTC | |
| | | SEQ ID NO 511 | GACCTCGAGCCATTGTGGTAAAC | |
| | | SEQ ID NO 512 | GACCTCGAGCCGTTGTGGTAAAC | |
| 74 | ITGB3 | SEQ ID NO 513 | GGCCCTGCCTCTGGGCTCACCTC | |
| | | SEQ ID NO 514 | GGCCCTGCCTCCGGGCTCACCTC | |
| | | SEQ ID NO 515 | GAGGTGAGCCCAGAGGCAGGGCC | |
| | | SEQ ID NO 516 | GAGGTGAGCCCGGAGGCAGGGCC | |
| 75 | CLCN7 | SEQ ID NO 517 | AAGCTCTGGGGATTGGGGGACCA | |
| | | SEQ ID NO 518 | AAGCTCTGGGGGTTGGGGGACCA | |
| | | SEQ ID NO 519 | TGGTCCCCCAATCCCCAGAGCTT | |
| | | SEQ ID NO 520 | TGGTCCCCCAACCCCCAGAGCTT | |
| 76 | CLCN7 | SEQ ID NO 521 | GGCCACCAGCACGGCCTCAATCA | |

Figure 2A (cont.)

| | | SEQ ID NO 522 | GGCCACCAGCATGGCCTCAATCA | |
|---|---|---|---|---|
| | | SEQ ID NO 523 | TGATTGAGGCCGTGCTGGTGGCC | |
| | | SEQ ID NO 524 | TGATTGAGGCCATGCTGGTGGCC | |
| 77 | CLCN7 | SEQ ID NO 525 | GCATTGAACACTGCTCCAAGCAC | |
| | | SEQ ID NO 526 | GCATTGAACACAGCTCCAAGCAC | |
| | | SEQ ID NO 527 | GTGCTTGGAGCAGTGTTCAATGC | |
| | | SEQ ID NO 528 | GTGCTTGGAGCTGTGTTCAATGC | |
| 78 | CLCN7 | SEQ ID NO 529 | TGAACCCCGGCCCTGGGGCCCCA | |
| | | SEQ ID NO 530 | TGAACCCCGGCTCTGGGGCCCCA | |
| | | SEQ ID NO 531 | TGGGGCCCCAGGGCCGGGGTTCA | |
| | | SEQ ID NO 532 | TGGGGCCCCAGAGCCGGGGTTCA | |
| 79 | CLCN7 | SEQ ID NO 533 | CGCGCAGCCCCAGGCCCAGCCCC | |
| | | SEQ ID NO 534 | CGCGCAGCCCCGGGCCCAGCCCC | |
| | | SEQ ID NO 535 | GGGGCTGGGCCTGGGGCTGCGCG | |
| | | SEQ ID NO 536 | GGGGCTGGGCCCGGGGCTGCGCG | |
| 80 | RANK (TNFRSF11A) | SEQ ID NO 537 | AAGACTCTTGCAAGTATGAATTT | |
| | | SEQ ID NO 538 | AAGACTCTTGCGAGTATGAATTT | |
| | | SEQ ID NO 539 | AAATTCATACTTGCAAGAGTCTT | |
| | | SEQ ID NO 540 | AAATTCATACTCGCAAGAGTCTT | |
| 81 | PPARG | SEQ ID NO 541 | TGCCATTCTGGCCCACCAACTTT | |
| | | SEQ ID NO 542 | TGCCATTCTGGGCCACCAACTTT | |
| | | SEQ ID NO 543 | AAAGTTGGTGGGCCAGAATGGCA | |
| | | SEQ ID NO 544 | AAAGTTGGTGGCCCAGAATGGCA | |
| 82 | KL | SEQ ID NO 545 | CGACCAACTTTGCCCGACTTGGG | |
| | | SEQ ID NO 546 | CGACCAACTTTACCCGACTTGGG | |
| | | SEQ ID NO 547 | CCCAAGTCGGGCAAAGTTGGTCG | |
| | | SEQ ID NO 548 | CCCAAGTCGGGTAAAGTTGGTCG | |
| 83 | KL | SEQ ID NO 549 | CAGGAAATGCACGTTACACATTT | |
| | | SEQ ID NO 550 | CAGGAAATGCATGTTACACATTT | |
| | | SEQ ID NO 551 | AAATGTGTAACGTGCATTTCCTG | |
| | | SEQ ID NO 552 | AAATGTGTAACATGCATTTCCTG | |
| 84 | PTHR1 | SEQ ID NO 553 | CATGGATGCCCGAGCCTGCTGAC | |
| | | SEQ ID NO 554 | CATGGATGCCCAAGCCTGCTGAC | |
| | | SEQ ID NO 555 | GTCAGCAGGCTCGGGCATCCATG | |
| | | SEQ ID NO 556 | GTCAGCAGGCTTGGGCATCCATG | |
| 85 | PTHR1 | SEQ ID NO 557 | GCCCTGCTGTTACCTGAGCCTGG | |
| | | SEQ ID NO 558 | GCCCTGCTGTTCCCTGAGCCTGG | |
| | | SEQ ID NO 559 | CCAGGCTCAGGTAACAGCAGGGC | |
| | | SEQ ID NO 560 | CCAGGCTCAGGGAACAGCAGGGC | |
| 86 | PTHR1 | SEQ ID NO 561 | GGGCTGGTTCCCGGGGACGCAGG | |
| | | SEQ ID NO 562 | GGGCTGGTTCCTGGGGACGCAGG | |
| | | SEQ ID NO 563 | CCTGCGTCCCCGGGAACCAGCCC | |
| | | SEQ ID NO 564 | CCTGCGTCCCCAGGAACCAGCCC | |
| 87 | PTHR1 | SEQ ID NO 565 | TGTTTCTGCAACGGCGAGGTAAG | |
| | | SEQ ID NO 566 | TGTTTCTGCAATGGCGAGGTAAG | |
| | | SEQ ID NO 567 | CTTACCTCGCCGTTGCAGAAACA | |
| | | SEQ ID NO 568 | CTTACCTCGCCATTGCAGAAACA | |
| 88 | BMP 2 | SEQ ID NO 569 | TCGCGGCGGCGTCGTCGGGCCGC | |
| | | SEQ ID NO 570 | TCGCGGCGGCGGCGTCGGGCCGC | |
| | | SEQ ID NO 571 | GCGGCCCGACGACGCCGCCGCGA | |

Figure 2A (cont.)

| | | SEQ ID NO 572 | GCGGCCCGACGCCGCCGCCGCGA | |
|---|---|---|---|---|
| 89 | CYP1B1 | SEQ ID NO 573 | ATCATGACCCACTGAAGTGGCCT | |
| | | SEQ ID NO 574 | ATCATGACCCAGTGAAGTGGCCT | |
| | | SEQ ID NO 575 | AGGCCACTTCAGTGGGTCATGAT | |
| | | SEQ ID NO 576 | AGGCCACTTCACTGGGTCATGAT | |
| 90 | IGF-II | SEQ ID NO 577 | CTGCAGCCCGGCGCCACCATCCT | |
| | | SEQ ID NO 578 | CTGCAGCCCGGTGCCACCATCCT | |
| | | SEQ ID NO 579 | AGGATGGTGGCGCCGGGCTGCAG | |
| | | SEQ ID NO 580 | AGGATGGTGGCACCGGGCTGCAG | |
| 91 | SOST | SEQ ID NO 581 | CCCTGTGTCTCATCTGCCTGCTG | |
| | | SEQ ID NO 582 | CCCTGTGTCTCGTCTGCCTGCTG | |
| | | SEQ ID NO 583 | CAGCAGGCAGATGAGACACAGGG | |
| | | SEQ ID NO 584 | CAGCAGGCAGACGAGACACAGGG | |
| 92 | NPPB | SEQ ID NO 585 | TTCTCTGGAAGGGGAGTGACATC | |
| | | SEQ ID NO 586 | TTCTCTGGAAGAGGAGTGACATC | |
| | | SEQ ID NO 587 | GATGTCACTCCCCTTCCAGAGAA | |
| | | SEQ ID NO 588 | GATGTCACTCCTCTTCCAGAGAA | |
| 93 | ADRB2 | SEQ ID NO 589 | CCGGGCCAGCCCCAGGAGAAGGA | |
| | | SEQ ID NO 590 | CCGGGCCAGCCTCAGGAGAAGGA | |
| | | SEQ ID NO 591 | TCCTTCTCCTGGGGCTGGCCCGG | |
| | | SEQ ID NO 592 | TCCTTCTCCTGAGGCTGGCCCGG | |
| 94 | TNSALP (ALPL) | SEQ ID NO 593 | TCAAACCGAGATACAAGGTAGCC | |
| | | SEQ ID NO 594 | TCAAACCGAGACACAAGGTAGCC | |
| | | SEQ ID NO 595 | GGCTACCTTGTATCTCGGTTTGA | |
| | | SEQ ID NO 596 | GGCTACCTTGTGTCTCGGTTTGA | |
| 95 | ALOX5AP | SEQ ID NO 597 | CATGACCAGCACGAGCCCAGCAC | |
| | | SEQ ID NO 598 | CATGACCAGCATGAGCCCAGCAC | |
| | | SEQ ID NO 599 | GTGCTGGGCTCGTGCTGGTCATG | |
| | | SEQ ID NO 600 | GTGCTGGGCTCATGCTGGTCATG | |
| 96 | FDPS | SEQ ID NO 601 | ACTCCCACCCCAGCCTTAGCCCA | |
| | | SEQ ID NO 602 | ACTCCCACCCCCGCCTTAGCCCA | |
| | | SEQ ID NO 603 | TGGGCTAAGGCTGGGGTGGGAGT | |
| | | SEQ ID NO 604 | TGGGCTAAGGCGGGGGTGGGAGT | |
| 97 | ALOX15 | SEQ ID NO 605 | AATAAGTGACATATTGGCTGCAG | |
| | | SEQ ID NO 606 | AATAAGTGACACATTGGCTGCAG | |
| | | SEQ ID NO 607 | CTGCAGCCAATATGTCACTTATT | |
| | | SEQ ID NO 608 | CTGCAGCCAATGTGTCACTTATT | |
| 98 | BMP 4 | SEQ ID NO 609 | CAATCCTGGCATGTTCCTTAAAC | |
| | | SEQ ID NO 610 | CAATCCTGGCACGTTCCTTAAAC | |
| | | SEQ ID NO 611 | GTTTAAGGAACATGCCAGGATTG | |
| | | SEQ ID NO 612 | GTTTAAGGAACGTGCCAGGATTG | |
| 99 | BMP 4 | SEQ ID NO 613 | CCTTCCCCCTCTCCGGAATTCAC | |
| | | SEQ ID NO 614 | CCTTCCCCCTCCCCGGAATTCAC | |
| | | SEQ ID NO 615 | GTGAATTCCGGAGAGGGGGAAGG | |
| | | SEQ ID NO 616 | GTGAATTCCGGGGAGGGGGAAGG | |
| 100 | BMP 4 | SEQ ID NO 617 | TGAGAACGAGGTGATCTCCTCTG | |
| | | SEQ ID NO 618 | TGAGAACGAGGCGATCTCCTCTG | |
| | | SEQ ID NO 619 | CAGAGGAGATCACCTCGTTCTCA | |
| | | SEQ ID NO 620 | CAGAGGAGATCGCCTCGTTCTCA | |
| 101 | CYP19 | SEQ ID NO 621 | AATGGCATGTTGAAAAACACAGC | |
| | | SEQ ID NO 622 | AATGGCATGTTAAAAAACACAGC | |

Figure 2A (cont.)

| | | SEQ ID NO 623 | GCTGTGTTTTTCAACATGCCATT | |
|---|---|---|---|---|
| | | SEQ ID NO 624 | GCTGTGTTTTTCAACATGCCATT | |
| 102 | MKP1 | SEQ ID NO 625 | GGCACGTCGCCCGTTCTCCCGGC | |
| | | SEQ ID NO 626 | AGCGAGCCCTCTTCCTCCCCGCT | |
| | | SEQ ID NO 627 | GCCGGGAGAACGGGCGACGTGAA | |
| | | SEQ ID NO 628 | GCCGGGAGAACAGGCGACGTGAA | |
| 103 | MKP1 | SEQ ID NO 629 | AGCGAGCCCTCCTCCTCCCCGCT | |
| | | SEQ ID NO 630 | AGCGAGCCCTCTTCCTCCCCGCT | |
| | | SEQ ID NO 631 | AGCGGGGAGGAGGAGGGCTCGCT | |
| | | SEQ ID NO 632 | AGCGGGGAGGAAGAGGGCTCGCT | |
| 104 | MKP1 | SEQ ID NO 633 | GCCTCCAGCGTCCAGGGTGCCCA | |
| | | SEQ ID NO 634 | GCCTCCAGCGTTCAGGGTGCCCA | |
| | | SEQ ID NO 635 | GCCTCCAGCGTCCAGGGTGCCCA | |
| | | SEQ ID NO 636 | GCCTCCAGCGTTCAGGGTGCCCA | |
| 105 | MKP1 | SEQ ID NO 637 | CCGAGTCTCCAATTGTAGGCTCT | |
| | | SEQ ID NO 638 | CCGAGTCTCCAGTTGTAGGCTCT | |
| | | SEQ ID NO 639 | AGAGCCTACAATTGGAGACTCGG | |
| | | SEQ ID NO 640 | AGAGCCTACAACTGGAGACTCGG | |
| 106 | MKP1 | SEQ ID NO 641 | TGGGCAGTGCGTATCACGCTTCC | |
| | | SEQ ID NO 642 | TGGGCAGTGCGCATCACGCTTCC | |
| | | SEQ ID NO 643 | GGGCAGTGCGTATCACGCTTC | |
| | | SEQ ID NO 644 | GGGCAGTGCGCATCACGCTTC | |
| 107 | ESRRAL | SEQ ID NO 645 | ATGAAGGTCACGGGGAAGGGCG | |
| | | SEQ ID NO 646 | ATGAAGGTCACTGCGGTGACCGA | |
| | | SEQ ID NO 647 | CGCCCTTCCCCGTGACCTTCAT | |
| | | SEQ ID NO 648 | TCGGTCACCGCAGTGACCTTCAT | |
| 108 | PPARG | SEQ ID NO 649 | TGTTTTGTCTTCATGGAAAATAC | |
| | | SEQ ID NO 650 | TGTTTTGTCTTGATGGAAAATAC | |
| | | SEQ ID NO 651 | TGTTTTGTCTTCATGGAAAATAC | |
| | | SEQ ID NO 652 | TGTTTTGTCTTGATGGAAAATAC | |
| 109 | PPARG | SEQ ID NO 653 | GTCACGGAACACGTGCAGCTACT | |
| | | SEQ ID NO 654 | GTCACGGAACATGTGCAGCTACT | |
| | | SEQ ID NO 655 | TCACGGAACACGTGCAGCTAC | |
| | | SEQ ID NO 656 | TCACGGAACATGTGCAGCTAC | |
| 110 | POMC | SEQ ID NO 657 | TGCGGTGAGCCAAGATCGCGCCA | |
| | | SEQ ID NO 658 | TGCGGTGAGCCGAGATCGCGCCA | |
| | | SEQ ID NO 659 | TGGCGCGATCTTGGCTCACCGCA | |
| | | SEQ ID NO 660 | TGGCGCGATCTCGGCTCACCGCA | |
| 111 | BMP6 | SEQ ID NO 661 | AACCAATACCAGGGGCAGTGGGA | |
| | | SEQ ID NO 662 | AACCAATACCAAGGGCAGTGGGA | |
| | | SEQ ID NO 663 | TCCCACTGCCCCTGGTATTGGTT | |
| | | SEQ ID NO 664 | TCCCACTGCCCTTGGTATTGGTT | |
| 112 | BMP6 | SEQ ID NO 665 | GACACGGGGACAAAGGTCCTTT | |
| | | SEQ ID NO 666 | GACACGGGGATAAAGGTCCTTT | |
| | | SEQ ID NO 667 | AAAGGACCTTTGTCCCCCGTGTC | |
| | | SEQ ID NO 668 | AAAGGACCTTTATCCCCCGTGTC | |

Figure 2B: Table 2B

| # SNP | Gene Symbol | ID Number | Sequence |
|---|---|---|---|
| 1 | VDR | SEQ ID NO 693 | CCATTGCCTCCGTCCCTGTAAGA |
| 4 | ESR1 | SEQ ID NO 694 | AATGTCCCAGCTGTTTTATGCTT |
| | | SEQ ID NO 695 | AATGTCCCAGCCGTTTTATGCTT |
| 13 | Coll1A2 | SEQ ID NO 696 | CCCAATTGGCCCCAGCTGGAGCAAGA |
| | | SEQ ID NO 697 | CCCAATTGGCCCCGCTGGAGCAAGA |
| 15 | PTH | SEQ ID NO 698 | TCACTAAAAGGACAAGCAAAATGGA |
| | | SEQ ID NO 699 | TCACTAAAAGGATAAGCAAAATGGA |
| 17 | LRP-5 | SEQ ID NO 700 | CCTTTTTTCGGGGCCTCTG |
| | | SEQ ID NO 701 | CCTTTTTTCTGGGCCTCTG |
| | | SEQ ID NO 702 | TCCTTTTTTCGGGGCCTCTGG |
| | | SEQ ID NO 703 | TCCTTTTTTCTGGGCCTCTGG |
| 19 | LRP-5 | SEQ ID NO 704 | GACCAAGAAGGCGTCAGGCACGATG |
| | | SEQ ID NO 705 | GACCAAGAAGGCATCAGGCACGATG |
| | | SEQ ID NO 706 | CATCGTGCCTGACGCCTTCTTGGTC |
| | | SEQ ID NO 707 | CATCGTGCCTGATGCCTTCTTGGTC |
| 21 | LRP-5 | SEQ ID NO 708 | CTTCGATTCTGTTGGTCCCAG |
| | | SEQ ID NO 709 | CTTCGATTCTATTGGTCCCAG |
| | | SEQ ID NO 710 | TTCGATTCTGTTGGTCCCA |
| | | SEQ ID NO 711 | TTCGATTCTATTGGTCCCA |
| 23 | LRP-5 | SEQ ID NO 712 | GTCACAGTCCGCCTCGTCTGA |
| | | SEQ ID NO 713 | GTCACAGTCCACCTCGTCTGA |
| 26 | CYP17 | SEQ ID NO 714 | TCTACTCCACTGCTGTCTATC |
| | | SEQ ID NO 715 | TCTACTCCACCGCTGTCTATC |
| | | SEQ ID NO 716 | CTACTCCACTGCTGTCTAT |
| | | SEQ ID NO 717 | CTACTCCACCGCTGTCTAT |
| 31 | IL-1b | SEQ ID NO 718 | CTATCTTCTTCGACACATGGG |
| | | SEQ ID NO 719 | CTATCTTCTTTGACACATGGG |
| | | SEQ ID NO 720 | TATCTTCTTCGACACATGG |
| | | SEQ ID NO 721 | TATCTTCTTTGACACATGG |
| 34 | IL-10 | SEQ ID NO 722 | GCTTCTTTGGGAGGGGGAAGTAGGG |
| | | SEQ ID NO 723 | GCTTCTTTGGGAAGGGGAAGTAGGG |
| | | SEQ ID NO 724 | GGCTTCTTTGGGAGGGGGAAGTAGGGA |
| | | SEQ ID NO 725 | GGCTTCTTTGGGAAGGGGAAGTAGGGA |
| 37 | LRP-5 | SEQ ID NO 726 | gcggggctgcgtgtgatgttc |
| | | SEQ ID NO 727 | gcggggctgcatgtgatgttc |
| | | SEQ ID NO 728 | cggggctgcgtgtgatgtt |
| | | SEQ ID NO 729 | cggggctgcatgtgatgtt |
| 41 | OPG | SEQ ID NO 730 | CCTCGAGGAGGCAACTCCAGAAGTT |
| | | SEQ ID NO 731 | CCTCGAGGAGGCCACTCCAGAAGTT |
| 44 | OPG | SEQ ID NO 732 | TCCAAGGTATGATTATCTAAAATAAAA |
| | | SEQ ID NO 733 | TCCAAGGTATGATGATCTAAAATAAAA |
| 45 | TNFa | SEQ ID NO 734 | AACCCCGTCCCCATGCCCCTC |
| | | SEQ ID NO 735 | AACCCCGTCCTCATGCCCCTC |
| | | SEQ ID NO 736 | ACCCCGTCCCCATGCCCCT |
| | | SEQ ID NO 737 | ACCCCGTCCTCATGCCCCT |
| 46 | TNFa | SEQ ID NO 738 | TCTTTCTCCATGTTTTTTTCT |
| | | SEQ ID NO 739 | TCTTTCTCCACGTTTTTTTCT |
| | | SEQ ID NO 740 | CTTTCTCCATGTTTTTTTC |

Figure 2B (cont.)

| | | SEQ ID NO 741 | CTTTCTCCACGTTTTTTTC | |
|---|---|---|---|---|
| 47 | MTHFR | SEQ ID NO 742 | TCTGCGGGAGCCGATTTCATC | |
| | | SEQ ID NO 743 | TCTGCGGGAGTCGATTTCATC | |
| | | SEQ ID NO 744 | CTGCGGGAGCCGATTTCAT | |
| | | SEQ ID NO 745 | CTGCGGGAGTCGATTTCAT | |
| 48 | COMT | SEQ ID NO 746 | TTGTCCTTCACGCCAGCGAAA | |
| | | SEQ ID NO 747 | TTGTCCTTCATGCCAGCGAAA | |
| | | SEQ ID NO 748 | TGTCCTTCACGCCAGCGAA | |
| | | SEQ ID NO 749 | TGTCCTTCATGCCAGCGAA | |
| 51 | SRD5A2 | SEQ ID NO 750 | CCGCCTGCCAGCCCGCGCCGC | |
| | | SEQ ID NO 751 | CCGCCTGCCAACCCGCGCCGC | |
| | | SEQ ID NO 752 | CGCCTGCCAGCCCGCGCCG | |
| | | SEQ ID NO 753 | CGCCTGCCAACCCGCGCCG | |
| 52 | SRD5A2 | SEQ ID NO 754 | CCTCTTCTGCGTACATTACTT | |
| | | SEQ ID NO 755 | CCTCTTCTGCCTACATTACTT | |
| | | SEQ ID NO 756 | CTCTTCTGCGTACATTACT | |
| | | SEQ ID NO 757 | CTCTTCTGCCTACATTACT | |
| 54 | PPARA | SEQ ID NO 758 | TCACAAGTGCCTTTCTGTCGG | |
| | | SEQ ID NO 759 | TCACAAGTGCGTTTCTGTCGG | |
| | | SEQ ID NO 760 | CACAAGTGCCTTTCTGTCG | |
| | | SEQ ID NO 761 | CACAAGTGCGTTTCTGTCG | |
| 56 | ADRB2 | SEQ ID NO 762 | CTGGCACCCAATGGAAGCCATGCGC | |
| | | SEQ ID NO 763 | CTGGCACCCAATAGAAGCCATGCGC | |
| | | SEQ ID NO 764 | GCGCATGGCTTCCATTGGGTGCCAG | |
| | | SEQ ID NO 765 | GCGCATGGCTTCTATTGGGTGCCAG | |
| 57 | ADRB2 | SEQ ID NO 766 | TCGTCCCTTTGCTGCGTGACG | |
| | | SEQ ID NO 767 | TCGTCCCTTTCCTGCGTGACG | |
| | | SEQ ID NO 768 | CGTCCCTTTGCTGCGTGAC | |
| | | SEQ ID NO 769 | CGTCCCTTTCCTGCGTGAC | |
| 58 | ADRB1 | SEQ ID NO 770 | CAGAGCAGTCGCTGGAAGGCC | |
| | | SEQ ID NO 771 | CAGAGCAGTCCCTGGAAGGCC | |
| | | SEQ ID NO 772 | AGAGCAGTCGCTGGAAGGC | |
| | | SEQ ID NO 773 | AGAGCAGTCCCTGGAAGGC | |
| 61 | ADRB1 | SEQ ID NO 774 | GGCTCGGGGCTTTCGCTGGCG | |
| | | SEQ ID NO 775 | GGCTCGGGGCCTTCGCTGGCG | |
| | | SEQ ID NO 776 | GCTCGGGGCTTTCGCTGGC | |
| | | SEQ ID NO 777 | GCTCGGGGCCTTCGCTGGC | |
| 70 | COX1 (PTGS1) | SEQ ID NO 778 | TGCTCACCTACGAGCTCCTGG | |
| | | SEQ ID NO 779 | TGCTCACCTATGAGCTCCTGG | |
| | | SEQ ID NO 780 | GCTGCTCACCTACGAGCTCCTGGAA | |
| | | SEQ ID NO 781 | GCTGCTCACCTATGAGCTCCTGGAA | |
| 73 | LRP6 | SEQ ID NO 782 | ACCTCGAGCCATTGTGGTAAA | |
| | | SEQ ID NO 783 | ACCTCGAGCCGTTGTGGTAAA | |
| | | SEQ ID NO 784 | CCTCGAGCCATTGTGGTAA | |
| | | SEQ ID NO 785 | CCTCGAGCCGTTGTGGTAA | |
| 74 | ITGB3 | SEQ ID NO 786 | GCCCTGCCTCTGGGCTCACCT | |
| | | SEQ ID NO 787 | GCCCTGCCTCCGGGCTCACCT | |
| 75 | CLCN7 | SEQ ID NO 788 | AGCTCTGGGGATTGGGGACC | |
| | | SEQ ID NO 789 | AGCTCTGGGGGTTGGGGACC | |
| | | SEQ ID NO 790 | GGTCCCCCAATCCCCAGAGCT | |
| | | SEQ ID NO 791 | GGTCCCCCAACCCCCAGAGCT | |

Figure 2B (cont.)

| 76 | CLCN7 | SEQ ID NO 792 | GGTCCCCCAATCCCCAGAGCT | |
| | | SEQ ID NO 793 | GGTCCCCCAACCCCCAGAGCT | |
| 77 | CLCN7 | SEQ ID NO 794 | CATTGAACACTGCTCCAAGCA | |
| | | SEQ ID NO 795 | CATTGAACACAGCTCCAAGCA | |
| | | SEQ ID NO 796 | TGCTTGGAGCAGTGTTCAATG | |
| | | SEQ ID NO 797 | TGCTTGGAGCTGTGTTCAATG | |
| 78 | CLCN7 | SEQ ID NO 798 | CTGAACCCCGGCCCTGGGGCCCCAC | |
| | | SEQ ID NO 799 | CTGAACCCCGGCTCTGGGGCCCCAC | |
| 80 | RANK (TNFRSF11A) | SEQ ID NO 800 | AAAATTCATACTTGCAAGAGTCTTT | |
| | | SEQ ID NO 801 | AAAATTCATACTCGCAAGAGTCTTT | |
| 84 | PTHR1 | SEQ ID NO 802 | ATGGATGCCCGAGCCTGCTGA | |
| | | SEQ ID NO 803 | ATGGATGCCCAAGCCTGCTGA | |
| | | SEQ ID NO 804 | TGGATGCCCGAGCCTGCTG | |
| | | SEQ ID NO 805 | TGGATGCCCAAGCCTGCTG | |
| 85 | PTHR1 | SEQ ID NO 806 | CCCTGCTGTTACCTGAGCCTG | |
| | | SEQ ID NO 807 | CCCTGCTGTTCCCTGAGCCTG | |
| | | SEQ ID NO 808 | CCTGCTGTTACCTGAGCCT | |
| | | SEQ ID NO 809 | CCTGCTGTTCCCTGAGCCT | |
| 86 | PTHR1 | SEQ ID NO 810 | GGGGCTGGTTCCCGGGGACGCAGGC | |
| | | SEQ ID NO 811 | GGGGCTGGTTCCTGGGGACGCAGGC | |
| | | SEQ ID NO 812 | GGCTGGTTCCCGGGGACGCAG | |
| | | SEQ ID NO 813 | GGCTGGTTCCTGGGGACGCAG | |
| 87 | PTHR1 | SEQ ID NO 814 | GTTTCTGCAACGGCGAGGTAA | |
| | | SEQ ID NO 815 | GTTTCTGCAATGGCGAGGTAA | |
| | | SEQ ID NO 816 | TTTCTGCAACGGCGAGGTA | |
| | | SEQ ID NO 817 | TTTCTGCAATGGCGAGGTA | |
| 90 | IGF-II | SEQ ID NO 818 | TGCAGCCCGGCGCCACCATCC | |
| | | SEQ ID NO 819 | TGCAGCCCGGTGCCACCATCC | |
| 91 | SOST | SEQ ID NO 820 | CCTGTGTCTCATCTGCCTGCT | |
| | | SEQ ID NO 821 | CCTGTGTCTCGTCTGCCTGCT | |
| | | SEQ ID NO 822 | CTGTGTCTCATCTGCCTGC | |
| | | SEQ ID NO 823 | CTGTGTCTCGTCTGCCTGC | |
| 92 | NPPB | SEQ ID NO 824 | attctctggaaggggagtgacatca | |
| | | SEQ ID NO 825 | attctctggaagaggagtgacatca | |
| 93 | ADRB2 | SEQ ID NO 826 | CCTTCTCCTGGGGCTGGCCCG | |
| | | SEQ ID NO 827 | CCTTCTCCTGAGGCTGGCCCG | |
| 109 | PPARG | SEQ ID NO 828 | TCACGGAACACGTGCAGCTAC | |
| | | SEQ ID NO 829 | TCACGGAACATGTGCAGCTAC | |

Figure 2C: Table 2C

| # SNP | Gene Symbol | ID number | Sequence |
|---|---|---|---|
| 1 | VDR | SEQ ID NO 221 | TCTTACAGGGACGGAGGCAATGG |
|  |  | SEQ ID NO 222 | TCTTACAGGGATGGAGGCAATGG |
|  |  | SEQ ID NO 693 | CCATTGCCTCCGTCCCTGTAAGA |
|  |  | SEQ ID NO 224 | CCATTGCCTCCATCCCTGTAAGA |
| 2 | VDR | SEQ ID NO 225 | GACAGGCCTGCGCATTCCCAATA |
|  |  | SEQ ID NO 226 | GACAGGCCTGCACATTCCCAATA |
|  |  | SEQ ID NO 227 | TATTGGGAATGCGCAGGCCTGTC |
|  |  | SEQ ID NO 228 | TATTGGGAATGTGCAGGCCTGTC |
| 3 | VDR | SEQ ID NO 229 | GCCGCGCTGATTGAGGCCATCCA |
|  |  | SEQ ID NO 230 | GCCGCGCTGATCGAGGCCATCCA |
|  |  | SEQ ID NO 231 | TGGATGGCCTCAATCAGCGCGGC |
|  |  | SEQ ID NO 232 | TGGATGGCCTCGATCAGCGCGGC |
| 4 | ESR1 | SEQ ID NO 694 | AATGTCCCAGCTGTTTTATGCTT |
|  |  | SEQ ID NO 695 | AATGTCCCAGCCGTTTTATGCTT |
|  |  | SEQ ID NO 694 | AATGTCCCAGCTGTTTTATGCTT |
|  |  | SEQ ID NO 695 | AATGTCCCAGCCGTTTTATGCTT |
| 5 | ESR2 | SEQ ID NO 237 | GAGTGTGGTCTAGAGTTGGGATG |
|  |  | SEQ ID NO 238 | GAGTGTGGTCTGGAGTTGGGATG |
|  |  | SEQ ID NO 239 | CATCCCAACTCTAGACCACACTC |
|  |  | SEQ ID NO 240 | CATCCCAACTCCAGACCACACTC |
| 6 | ESR2 | SEQ ID NO 241 | TTCGACCAAGTGCGGCTCTTGGA |
|  |  | SEQ ID NO 242 | TTCGACCAAGTACGGCTCTTGGA |
|  |  | SEQ ID NO 243 | TCCAAGAGCCGCACTTGGTCGAA |
|  |  | SEQ ID NO 244 | TCCAAGAGCCGTACTTGGTCGAA |
| 7 | CYP19 | SEQ ID NO 245 | AAGCTCCCTGAGTTCCCCGCCTG |
|  |  | SEQ ID NO 246 | AAGCTCCCTGACTTCCCCGCCTG |
|  |  | SEQ ID NO 247 | CAGGCGGGGAACTCAGGGAGCTT |
|  |  | SEQ ID NO 248 | CAGGCGGGGAAGTCAGGGAGCTT |
| 8 | CYP19 | SEQ ID NO 249 | CAGAAAAAAGACGCAGGATTTCC |
|  |  | SEQ ID NO 250 | CAGAAAAAAGAGGCAGGATTTCC |
|  |  | SEQ ID NO 251 | GGAAATCCTGCGTCTTTTTTCTG |
|  |  | SEQ ID NO 252 | GGAAATCCTGCCTCTTTTTTCTG |
| 9 | CYP19 | SEQ ID NO 253 | CAGAAAAAAGACGCAGGATTTCC |
|  |  | SEQ ID NO 254 | CAGAAAAAAGATGCAGGATTTCC |
|  |  | SEQ ID NO 255 | GGAAATCCTGCGTCTTTTTTCTG |
|  |  | SEQ ID NO 256 | GGAAATCCTGCATCTTTTTTCTG |
| 10 | CYP19 | SEQ ID NO 257 | TAGCATCACTGGATTGGAGTGGA |
|  |  | SEQ ID NO 258 | TAGCATCACTGAATTGGAGTGGA |
|  |  | SEQ ID NO 259 | TCCACTCCAATCCAGTGATGCTA |
|  |  | SEQ ID NO 260 | TCCACTCCAATTCAGTGATGCTA |
| 11 | CYP19 | SEQ ID NO 261 | TGGTCAGTACCCACTCTGGAGCA |
|  |  | SEQ ID NO 262 | TGGTCAGTACCTACTCTGGAGCA |
|  |  | SEQ ID NO 263 | TGCTCCAGAGTGGGTACTGACCA |
|  |  | SEQ ID NO 264 | TGCTCCAGAGTAGGTACTGACCA |
| 12 | CollA1 | SEQ ID NO 265 | CCCAGGGAATGGGGGCGGGATGA |
|  |  | SEQ ID NO 266 | CCCAGGGAATGTGGGCGGGATGA |
|  |  | SEQ ID NO 267 | TCATCCCGCCCCCATTCCCTGGG |
|  |  | SEQ ID NO 268 | TCATCCCGCCCACATTCCCTGGG |

Figure 2C (cont.)

| 13 | Col1A2 | SEQ ID NO 696 | CCCAATTGGCCCAGCTGGAGCAAGA |
|---|---|---|---|
| | | SEQ ID NO 697 | CCCAATTGGCCCCGCTGGAGCAAGA |
| | | SEQ ID NO 271 | CTTGCTCCAGCTGGGCCAATTGG |
| | | SEQ ID NO 272 | CTTGCTCCAGCGGGGCCAATTGG |
| 14 | Col1A2 | SEQ ID NO 275 | TTAATTTCCAGGATTCTATGTGA |
| | | SEQ ID NO 276 | TTAATTTCCAGAATTCTATGTGA |
| | | SEQ ID NO 275 | TTAATTTCCAGGATTCTATGTGA |
| | | SEQ ID NO 276 | TTAATTTCCAGAATTCTATGTGA |
| 15 | PTH | SEQ ID NO 277 | CCATTTTGCTTGTCCTTTTAGTG |
| | | SEQ ID NO 278 | CCATTTTGCTTATCCTTTTAGTG |
| | | SEQ ID NO 698 | TCACTAAAAGGACAAGCAAAATGGA |
| | | SEQ ID NO 699 | TCACTAAAAGGATAAGCAAAATGGA |
| 16 | PTH | SEQ ID NO 281 | TTTATCATTTCGAAGTGGGGAGC |
| | | SEQ ID NO 282 | TTTATCATTTCAAAGTGGGGAGC |
| | | SEQ ID NO 283 | GCTCCCCACTTCGAAATGATAAA |
| | | SEQ ID NO 284 | GCTCCCCACTTTGAAATGATAAA |
| 17 | PTH | SEQ ID NO 700 | CCTTTTTTCGGGGCCTCTG |
| | | SEQ ID NO 701 | CCTTTTTTCTGGGCCTCTG |
| | | SEQ ID NO 702 | TCCTTTTTTCGGGGCCTCTGG |
| | | SEQ ID NO 703 | TCCTTTTTTCTGGGCCTCTGG |
| 18 | LRP-5 | SEQ ID NO 289 | TCCTGGTTTTCTCAGTCCACACT |
| | | SEQ ID NO 290 | TCCTGGTTTTCCCAGTCCACACT |
| | | SEQ ID NO 291 | AGTGTGGACTGAGAAAACCAGGA |
| | | SEQ ID NO 292 | AGTGTGGACTGGGAAAACCAGGA |
| 19 | LRP-5 | SEQ ID NO 704 | GACCAAGAAGGCGTCAGGCACGATG |
| | | SEQ ID NO 705 | GACCAAGAAGGCATCAGGCACGATG |
| | | SEQ ID NO 706 | CATCGTGCCTGACGCCTTCTTGGTC |
| | | SEQ ID NO 707 | CATCGTGCCTGATGCCTTCTTGGTC |
| 20 | LRP-5 | SEQ ID NO 299 | CGGGATGGCCACGTCGTTGTTAT |
| | | SEQ ID NO 300 | CGGGATGGCCATGTCGTTGTTAT |
| | | SEQ ID NO 299 | CGGGATGGCCACGTCGTTGTTAT |
| | | SEQ ID NO 300 | CGGGATGGCCATGTCGTTGTTAT |
| 21 | LRP-5 | SEQ ID NO 708 | CTTCGATTCTGTTGGTCCCAG |
| | | SEQ ID NO 709 | CTTCGATTCTATTGGTCCCAG |
| | | SEQ ID NO 710 | TTCGATTCTGTTGGTCCCA |
| | | SEQ ID NO 711 | TTCGATTCTATTGGTCCCA |
| 22 | LRP-5 | SEQ ID NO 305 | GCCCTGGTGGTAGACAACACACT |
| | | SEQ ID NO 306 | GCCCTGGTGGTGGACAACACACT |
| | | SEQ ID NO 307 | AGTGTGTTGTCTACCACCAGGGC |
| | | SEQ ID NO 308 | AGTGTGTTGTCCACCACCAGGGC |
| 23 | LRP-5 | SEQ ID NO 712 | GTCACAGTCCGCCTCGTCTGA |
| | | SEQ ID NO 713 | GTCACAGTCCACCTCGTCTGA |
| | | SEQ ID NO 311 | CGTCACAGTCCGCCTCGTCTGAG |
| | | SEQ ID NO 312 | CGTCACAGTCCACCTCGTCTGAG |
| 24 | LCT | SEQ ID NO 313 | GTGAGCCACCGGGCCCAGCTGAG |
| | | SEQ ID NO 314 | GTGAGCCACCGGACCCAGCTGAG |
| | | SEQ ID NO 313 | GTGAGCCACCGGGCCCAGCTGAG |
| | | SEQ ID NO 314 | GTGAGCCACCGGACCCAGCTGAG |
| 25 | LCT | SEQ ID NO 317 | ATAATGTAGCCCCTGGCCTCAAA |
| | | SEQ ID NO 318 | ATAATGTAGCCTCTGGCCTCAAA |
| | | SEQ ID NO 319 | TTTGAGGCCAGGGGCTACATTAT |

Figure 2C (cont.)

|    |        |              |                            |
|----|--------|--------------|----------------------------|
|    |        | SEQ ID NO 320 | TTTGAGGCCAGAGGCTACATTAT |
| 26 | CYP17  | SEQ ID NO 714 | TCTACTCCACTGCTGTCTATC |
|    |        | SEQ ID NO 715 | TCTACTCCACCGCTGTCTATC |
|    |        | SEQ ID NO 716 | CTACTCCACTGCTGTCTAT |
|    |        | SEQ ID NO 717 | CTACTCCACCGCTGTCTAT |
| 27 | CaSR   | SEQ ID NO 327 | GTGGGCCATGGCGTTCTTCTGAG |
|    |        | SEQ ID NO 328 | GTGGGCCATGGAGTTCTTCTGAG |
|    |        | SEQ ID NO 327 | GTGGGCCATGGCGTTCTTCTGAG |
|    |        | SEQ ID NO 328 | GTGGGCCATGGAGTTCTTCTGAG |
| 28 | AR     | SEQ ID NO 329 | AGAGCGAGGGAGGCCTCGGGGGC |
|    |        | SEQ ID NO 330 | AGAGCGAGGGAAGCCTCGGGGGC |
|    |        | SEQ ID NO 331 | GCCCCCGAGGCCTCCCTCGCTCT |
|    |        | SEQ ID NO 332 | GCCCCCGAGGCTTCCCTCGCTCT |
| 29 | IL-6   | SEQ ID NO 333 | TTGTGTCTTGCGATGCTAAAGGA |
|    |        | SEQ ID NO 334 | TTGTGTCTTGCCATGCTAAAGGA |
|    |        | SEQ ID NO 335 | TCCTTTAGCATCGCAAGACACAA |
|    |        | SEQ ID NO 336 | TCCTTTAGCATGGCAAGACACAA |
| 30 | IL-1b  | SEQ ID NO 337 | ACAGGCTGCTCTGGGATTCTCTT |
|    |        | SEQ ID NO 338 | ACAGGCTGCTCGGGGATTCTCTT |
|    |        | SEQ ID NO 339 | AAGAGAATCCCAGAGCAGCCTGT |
|    |        | SEQ ID NO 340 | AAGAGAATCCCCGAGCAGCCTGT |
| 31 | IL-1b  | SEQ ID NO 718 | CTATCTTCTTCGACACATGGG |
|    |        | SEQ ID NO 719 | CTATCTTCTTTGACACATGGG |
|    |        | SEQ ID NO 720 | TATCTTCTTCGACACATGG |
|    |        | SEQ ID NO 721 | TATCTTCTTTGACACATGG |
| 32 | TGF-B1 | SEQ ID NO 345 | CCCTTCCATCCCTCAGGTGTCCT |
|    |        | SEQ ID NO 346 | CCCTTCCATCCTTCAGGTGTCCT |
|    |        | SEQ ID NO 347 | AGGACACCTGAGGGATGGAAGGG |
|    |        | SEQ ID NO 348 | AGGACACCTGAAGGATGGAAGGG |
| 34 | IL-10  | SEQ ID NO 722 | GCTTCTTTGGGAGGGGGAAGTAGGG |
|    |        | SEQ ID NO 723 | GCTTCTTTGGGAAGGGGAAGTAGGG |
|    |        | SEQ ID NO 724 | GGCTTCTTTGGGAGGGGGAAGTAGGGA |
|    |        | SEQ ID NO 725 | GGCTTCTTTGGGAAGGGGAAGTAGGGA |
| 35 | ESR2   | SEQ ID NO 357 | CAGAGGTCACAGGCTGAAGCGTG |
|    |        | SEQ ID NO 358 | CAGAGGTCACAAGCTGAAGCGTG |
|    |        | SEQ ID NO 359 | CACGCTTCAGCCTGTGACCTCTG |
|    |        | SEQ ID NO 360 | CACGCTTCAGCTTGTGACCTCTG |
| 36 | LRP-5  | SEQ ID NO 361 | GGCCATCAAGCAGACCTACCTGA |
|    |        | SEQ ID NO 362 | GGCCATCAAGCGGACCTACCTGA |
|    |        | SEQ ID NO 363 | TCAGGTAGGTCTGCTTGATGGCC |
|    |        | SEQ ID NO 364 | TCAGGTAGGTCCGCTTGATGGCC |
| 37 | LRP-5  | SEQ ID NO 726 | gcggggctgcgtgatgttc |
|    |        | SEQ ID NO 727 | gcggggctgcatgtgatgttc |
|    |        | SEQ ID NO 728 | cggggctgcgtgtgatgtt |
|    |        | SEQ ID NO 729 | cggggctgcatgtgatgtt |
| 38 | CYP1A1 | SEQ ID NO 369 | TATCGGTGAGACCATTGCCCGCT |
|    |        | SEQ ID NO 370 | TATCGGTGAGAACATTGCCCGCT |
|    |        | SEQ ID NO 371 | AGCGGGCAATGGTCTCACCGATA |
|    |        | SEQ ID NO 372 | AGCGGGCAATGTTCTCACCGATA |
| 39 | CTR    | SEQ ID NO 373 | CCATCAGGAGCTGAGGAATGAAC |
|    |        | SEQ ID NO 374 | CCATCAGGAGCCGAGGAATGAAC |

Figure 2C (cont.)

| | | | |
|---|---|---|---|
| | | SEQ ID NO 375 | GTTCATTCCTCAGCTCCTGATGG |
| | | SEQ ID NO 376 | GTTCATTCCTCGGCTCCTGATGG |
| 40 | OPG | SEQ ID NO 377 | GTCTCCCCCATAAATTCCCTGGT |
| | | SEQ ID NO 378 | GTCTCCCCCATGAATTCCCTGGT |
| | | SEQ ID NO 377 | GTCTCCCCCATAAATTCCCTGGT |
| | | SEQ ID NO 378 | GTCTCCCCCATGAATTCCCTGGT |
| 41 | OPG | SEQ ID NO 730 | CCTCGAGGAGGCAACTCCAGAAGTT |
| | | SEQ ID NO 731 | CCTCGAGGAGGCCACTCCAGAAGTT |
| | | SEQ ID NO 383 | CTCGAGGAGGCAACTCCAGAAGT |
| | | SEQ ID NO 384 | CTCGAGGAGGCCACTCCAGAAGT |
| 42 | OPG | SEQ ID NO 385 | GAAAGCGTTAATCCTGGAGCTTT |
| | | SEQ ID NO 386 | GAAAGCGTTAACCCTGGAGCTTT |
| | | SEQ ID NO 387 | AAAGCTCCAGGATTAACGCTTTC |
| | | SEQ ID NO 388 | AAAGCTCCAGGGTTAACGCTTTC |
| 43 | OPG | SEQ ID NO 389 | ACAATGAACAAGTTGCTGTGCTG |
| | | SEQ ID NO 390 | ACAATGAACAACTTGCTGTGCTG |
| | | SEQ ID NO 391 | CAGCACAGCAACTTGTTCATTGT |
| | | SEQ ID NO 392 | CAGCACAGCAAGTTGTTCATTGT |
| 44 | OPG | SEQ ID NO 732 | TCCAAGGTATGATTATCTAAAATAAAA |
| | | SEQ ID NO 733 | TCCAAGGTATGATGATCTAAAATAAAA |
| | | SEQ ID NO 732 | TCCAAGGTATGATTATCTAAAATAAAA |
| | | SEQ ID NO 733 | TCCAAGGTATGATGATCTAAAATAAAA |
| 45 | TNFa | SEQ ID NO 734 | AACCCCGTCCCCATGCCCCTC |
| | | SEQ ID NO 735 | AACCCCGTCCTCATGCCCCTC |
| | | SEQ ID NO 736 | ACCCCGTCCCCATGCCCCT |
| | | SEQ ID NO 737 | ACCCCGTCCTCATGCCCCT |
| 46 | TNFa | SEQ ID NO 738 | TCTTTCTCCATGTTTTTTTCT |
| | | SEQ ID NO 739 | TCTTTCTCCACGTTTTTTTCT |
| | | SEQ ID NO 740 | CTTTCTCCATGTTTTTTTC |
| | | SEQ ID NO 741 | CTTTCTCCACGTTTTTTTC |
| 47 | MTHFR | SEQ ID NO 742 | TCTGCGGGAGCCGATTTCATC |
| | | SEQ ID NO 743 | TCTGCGGGAGTCGATTTCATC |
| | | SEQ ID NO 744 | CTGCGGGAGCCGATTTCAT |
| | | SEQ ID NO 745 | CTGCGGGAGTCGATTTCAT |
| 48 | COMT | SEQ ID NO 746 | TTGTCCTTCACGCCAGCGAAA |
| | | SEQ ID NO 747 | TTGTCCTTCATGCCAGCGAAA |
| | | SEQ ID NO 748 | TGTCCTTCACGCCAGCGAA |
| | | SEQ ID NO 749 | TGTCCTTCATGCCAGCGAA |
| 49 | IL-1RA | SEQ ID NO 413 | GAAACAACCAAAATTTTTTCTTA |
| | | SEQ ID NO 414 | GAAACAACCAATATTTTTTCTTA |
| | | SEQ ID NO 415 | TAAGAAAAAATTTTGGTTGTTTC |
| | | SEQ ID NO 416 | TAAGAAAAAATATTGGTTGTTTC |
| 50 | TNFR2 (TNFRSF1B) | SEQ ID NO 417 | GAATGCAAGCATGGATGCAGTCT |
| | | SEQ ID NO 418 | GAATGCAAGCAGGGATGCAGTCT |
| | | SEQ ID NO 419 | AGACTGCATCCATGCTTGCATTC |
| | | SEQ ID NO 420 | AGACTGCATCCCTGCTTGCATTC |
| 51 | SRD5A2 | SEQ ID NO 750 | CCGCCTGCCAGCCCGCGCCGC |
| | | SEQ ID NO 751 | CCGCCTGCCAACCCGCGCCGC |
| | | SEQ ID NO 752 | CGCCTGCCAGCCCGCGCCG |
| | | SEQ ID NO 753 | CGCCTGCCAACCCGCGCCG |

Figure 2C (cont.)

| | | | |
|---|---|---|---|
| 52 | SRD5A2 | SEQ ID NO 754 | CCTCTTCTGCGTACATTACTT |
| | | SEQ ID NO 755 | CCTCTTCTGCCTACATTACTT |
| | | SEQ ID NO 756 | CTCTTCTGCGTACATTACT |
| | | SEQ ID NO 757 | CTCTTCTGCCTACATTACT |
| 54 | PPARA | SEQ ID NO 758 | TCACAAGTGCCTTTCTGTCGG |
| | | SEQ ID NO 759 | TCACAAGTGCGTTTCTGTCGG |
| | | SEQ ID NO 760 | CACAAGTGCCTTTCTGTCG |
| | | SEQ ID NO 761 | CACAAGTGCGTTTCTGTCG |
| 55 | P2X7Receptor | SEQ ID NO 439 | GTGCCTGGAGGTGCTGTGCTGCC |
| | | SEQ ID NO 440 | GTGCCTGGAGGGGCTGTGCTGCC |
| | | SEQ ID NO 439 | GTGCCTGGAGGTGCTGTGCTGCC |
| | | SEQ ID NO 440 | GTGCCTGGAGGGGCTGTGCTGCC |
| 56 | ADRB2 | SEQ ID NO 762 | CTGGCACCCAATGGAAGCCATGCGC |
| | | SEQ ID NO 763 | CTGGCACCCAATAGAAGCCATGCGC |
| | | SEQ ID NO 764 | GCGCATGGCTTCCATTGGGTGCCAG |
| | | SEQ ID NO 765 | GCGCATGGCTTCTATTGGGTGCCAG |
| 57 | ADRB2 | SEQ ID NO 766 | TCGTCCCTTTGCTGCGTGACG |
| | | SEQ ID NO 767 | TCGTCCCTTTCCTGCGTGACG |
| | | SEQ ID NO 768 | CGTCCCTTTGCTGCGTGAC |
| | | SEQ ID NO 769 | CGTCCCTTTCCTGCGTGAC |
| 58 | ADRB1 | SEQ ID NO 770 | CAGAGCAGTCGCTGGAAGGCC |
| | | SEQ ID NO 771 | CAGAGCAGTCCCTGGAAGGCC |
| | | SEQ ID NO 772 | AGAGCAGTCGCTGGAAGGC |
| | | SEQ ID NO 773 | AGAGCAGTCCCTGGAAGGC |
| 59 | ADRB2 | SEQ ID NO 453 | GTCAGGCCTTACCTCCTTCTTGC |
| | | SEQ ID NO 454 | GTCAGGCCTTATCTCCTTCTTGC |
| | | SEQ ID NO 455 | GCAAGAAGGAGGTAAGGCCTGAC |
| | | SEQ ID NO 456 | GCAAGAAGGAGATAAGGCCTGAC |
| 61 | ADRB1 | SEQ ID NO 774 | GGCTCGGGGCTTTCGCTGGCG |
| | | SEQ ID NO 775 | GGCTCGGGGCCTTCGCTGGCG |
| | | SEQ ID NO 776 | GCTCGGGGCTTTCGCTGGC |
| | | SEQ ID NO 777 | GCTCGGGGCCTTCGCTGGC |
| 63 | RANK (TNFRSF11A) | SEQ ID NO 469 | GAAATCCGATGTGGTTTGCAGTT |
| | | SEQ ID NO 470 | GAAATCCGATGCGGTTTGCAGTT |
| | | SEQ ID NO 471 | AACTGCAAACCACATCGGATTTC |
| | | SEQ ID NO 472 | AACTGCAAACCGCATCGGATTTC |
| 64 | ALOX5 | SEQ ID NO 473 | AACTTACTATAGCACTGCGGTAA |
| | | SEQ ID NO 474 | AACTTACTATAACACTGCGGTAA |
| | | SEQ ID NO 475 | TTACCGCAGTGCTATAGTAAGTT |
| | | SEQ ID NO 476 | TTACCGCAGTGTTATAGTAAGTT |
| 65 | ALOX5 | SEQ ID NO 477 | ATTACAGATCAGTGGACTAGAAT |
| | | SEQ ID NO 478 | ATTACAGATCAATGGACTAGAAT |
| | | SEQ ID NO 479 | ATTCTAGTCCACTGATCTGTAAT |
| | | SEQ ID NO 480 | ATTCTAGTCCATTGATCTGTAAT |
| 66 | ALOX5AP | SEQ ID NO 481 | CAGAGCTGCCCGAGAAGCTCCCG |
| | | SEQ ID NO 482 | CAGAGCTGCCCAAGAAGCTCCCG |
| | | SEQ ID NO 483 | CGGGAGCTTCTCGGGCAGCTCTG |
| | | SEQ ID NO 484 | CGGGAGCTTCTTGGGCAGCTCTG |
| 67 | ALOX12 | SEQ ID NO 485 | GGAAGAGCTTCGGGCTCAACTGG |
| | | SEQ ID NO 486 | GGAAGAGCTTCAGGCTCAACTGG |

Figure 2C (cont.)

| | | SEQ ID NO 487 | CCAGTTGAGCCCGAAGCTCTTCC |
|---|---|---|---|
| | | SEQ ID NO 488 | CCAGTTGAGCCTGAAGCTCTTCC |
| 68 | ALOX12 | SEQ ID NO 489 | TCAGCCTCCCAACCCCAGCTCTC |
| | | SEQ ID NO 490 | TCAGCCTCCCAGCCCCAGCTCTC |
| | | SEQ ID NO 491 | GAGAGCTGGGGTTGGGAGGCTGA |
| | | SEQ ID NO 492 | GAGAGCTGGGGCTGGGAGGCTGA |
| 69 | COX1 (PTGS1) | SEQ ID NO 493 | ATGGAGACAATCTGGAGCGTCAG |
| | | SEQ ID NO 494 | ATGGAGACAATCTGGAGCGTCAG |
| | | SEQ ID NO 495 | CTGACGCTCCAGATTGTCTCCAT |
| | | SEQ ID NO 496 | CTGACGCTCCAGATTGTCTCCAT |
| 70 | COX1 (PTGS1) | SEQ ID NO 778 | TGCTCACCTACGAGCTCCTGG |
| | | SEQ ID NO 779 | TGCTCACCTATGAGCTCCTGG |
| | | SEQ ID NO 780 | GCTGCTCACCTACGAGCTCCTGGAA |
| | | SEQ ID NO 781 | GCTGCTCACCTATGAGCTCCTGGAA |
| 71 | COX2 (PTGS2) | SEQ ID NO 501 | CCCCAGTCTGTCCCGACGTGACT |
| | | SEQ ID NO 502 | CCCCAGTCTGTTCCGACGTGACT |
| | | SEQ ID NO 501 | CCCCAGTCTGTCCCGACGTGACT |
| | | SEQ ID NO 502 | CCCCAGTCTGTTCCGACGTGACT |
| 72 | COX2 (PTGS2) | SEQ ID NO 505 | CATGGTAGAAGTTGGAGCACCAT |
| | | SEQ ID NO 506 | CATGGTAGAAGCTGGAGCACCAT |
| | | SEQ ID NO 507 | ATGGTGCTCCAACTTCTACCATG |
| | | SEQ ID NO 508 | ATGGTGCTCCAGCTTCTACCATG |
| 73 | LRP6 | SEQ ID NO 782 | ACCTCGAGCCATTGTGGTAAA |
| | | SEQ ID NO 783 | ACCTCGAGCCGTTGTGGTAAA |
| | | SEQ ID NO 784 | CCTCGAGCCATTGTGGTAA |
| | | SEQ ID NO 785 | CCTCGAGCCGTTGTGGTAA |
| 74 | ITGB3 | SEQ ID NO 786 | GCCCTGCCTCTGGGCTCACCT |
| | | SEQ ID NO 787 | GCCCTGCCTCCGGGCTCACCT |
| | | SEQ ID NO 786 | GCCCTGCCTCTGGGCTCACCT |
| | | SEQ ID NO 787 | GCCCTGCCTCCGGGCTCACCT |
| 75 | CLCN7 | SEQ ID NO 788 | AGCTCTGGGGATTGGGGGACC |
| | | SEQ ID NO 789 | AGCTCTGGGGGTTGGGGGACC |
| | | SEQ ID NO 790 | GGTCCCCCAATCCCCAGAGCT |
| | | SEQ ID NO 791 | GGTCCCCCAACCCCCAGAGCT |
| 76 | CLCN7 | SEQ ID NO 792 | GGTCCCCCAATCCCCAGAGCT |
| | | SEQ ID NO 793 | GGTCCCCCAACCCCCAGAGCT |
| | | SEQ ID NO 792 | GGTCCCCCAATCCCCAGAGCT |
| | | SEQ ID NO 793 | GGTCCCCCAACCCCCAGAGCT |
| 77 | CLCN7 | SEQ ID NO 794 | CATTGAACACTGCTCCAAGCA |
| | | SEQ ID NO 795 | CATTGAACACAGCTCCAAGCA |
| | | SEQ ID NO 796 | TGCTTGGAGCAGTGTTCAATG |
| | | SEQ ID NO 797 | TGCTTGGAGCTGTGTTCAATG |
| 78 | CLCN7 | SEQ ID NO 529 | TGAACCCCGGCCCTGGGGCCCCA |
| | | SEQ ID NO 530 | TGAACCCCGGCTCTGGGGCCCCA |
| | | SEQ ID NO 798 | CTGAACCCCGGCCCTGGGGCCCCAC |
| | | SEQ ID NO 799 | CTGAACCCCGGCTCTGGGGCCCCAC |
| 80 | RANK (TNFRSF11A) | SEQ ID NO 800 | AAAATTCATACTTGCAAGAGTCTTT |
| | | SEQ ID NO 801 | AAAATTCATACTCGCAAGAGTCTTT |
| | | SEQ ID NO 539 | AAATTCATACTTGCAAGAGTCTT |
| | | SEQ ID NO 540 | AAATTCATACTCGCAAGAGTCTT |

Figure 2C (cont.)

| | | | |
|---|---|---|---|
| 81 | PPARG | SEQ ID NO 541 | TGCCATTCTGGCCCACCAACTTT |
| | | SEQ ID NO 542 | TGCCATTCTGGGCCACCAACTTT |
| | | SEQ ID NO 543 | AAAGTTGGTGGGCCAGAATGGCA |
| | | SEQ ID NO 544 | AAAGTTGGTGGCCCAGAATGGCA |
| 82 | KL | SEQ ID NO 545 | CGACCAACTTTGCCCGACTTGGG |
| | | SEQ ID NO 546 | CGACCAACTTTACCCGACTTGGG |
| | | SEQ ID NO 545 | CGACCAACTTTGCCCGACTTGGG |
| | | SEQ ID NO 546 | CGACCAACTTTACCCGACTTGGG |
| 83 | KL | SEQ ID NO 549 | CAGGAAATGCACGTTACACATTT |
| | | SEQ ID NO 550 | CAGGAAATGCATGTTACACATTT |
| | | SEQ ID NO 551 | AAATGTGTAACGTGCATTTCCTG |
| | | SEQ ID NO 552 | AAATGTGTAACATGCATTTCCTG |
| 84 | PTHR1 | SEQ ID NO 802 | ATGGATGCCCGAGCCTGCTGA |
| | | SEQ ID NO 803 | ATGGATGCCCAAGCCTGCTGA |
| | | SEQ ID NO 804 | TGGATGCCCGAGCCTGCTG |
| | | SEQ ID NO 805 | TGGATGCCCAAGCCTGCTG |
| 85 | PTHR1 | SEQ ID NO 806 | CCCTGCTGTTACCTGAGCCTG |
| | | SEQ ID NO 807 | CCCTGCTGTTCCCTGAGCCTG |
| | | SEQ ID NO 808 | CCTGCTGTTACCTGAGCCT |
| | | SEQ ID NO 809 | CCTGCTGTTCCCTGAGCCT |
| 86 | PTHR1 | SEQ ID NO 810 | GGGGCTGGTTCCCGGGGACGCAGGC |
| | | SEQ ID NO 811 | GGGGCTGGTTCCTGGGGACGCAGGC |
| | | SEQ ID NO 812 | GGCTGGTTCCCGGGGACGCAG |
| | | SEQ ID NO 813 | GGCTGGTTCCTGGGGACGCAG |
| 87 | PTHR1 | SEQ ID NO 814 | GTTTCTGCAACGGCGAGGTAA |
| | | SEQ ID NO 815 | GTTTCTGCAATGGCGAGGTAA |
| | | SEQ ID NO 816 | TTTCTGCAACGGCGAGGTA |
| | | SEQ ID NO 817 | TTTCTGCAATGGCGAGGTA |
| 88 | BMP 2 | SEQ ID NO 571 | GCGGCCCGACGACGCCGCCGCGA |
| | | SEQ ID NO 572 | GCGGCCCGACGCCGCCGCCGCGA |
| | | SEQ ID NO 571 | GCGGCCCGACGACGCCGCCGCGA |
| | | SEQ ID NO 572 | GCGGCCCGACGCCGCCGCCGCGA |
| 89 | CYP1B1 | SEQ ID NO 573 | ATCATGACCCACTGAAGTGGCCT |
| | | SEQ ID NO 574 | ATCATGACCCAGTGAAGTGGCCT |
| | | SEQ ID NO 573 | ATCATGACCCACTGAAGTGGCCT |
| | | SEQ ID NO 574 | ATCATGACCCAGTGAAGTGGCCT |
| 90 | IGF-II | SEQ ID NO 577 | CTGCAGCCCGGCGCCACCATCCT |
| | | SEQ ID NO 578 | CTGCAGCCCGGTGCCACCATCCT |
| | | SEQ ID NO 818 | TGCAGCCCGGCGCCACCATCC |
| | | SEQ ID NO 819 | TGCAGCCCGGTGCCACCATCC |
| 91 | SOST | SEQ ID NO 820 | CCTGTGTCTCATCTGCCTGCT |
| | | SEQ ID NO 821 | CCTGTGTCTCGTCTGCCTGCT |
| | | SEQ ID NO 822 | CTGTGTCTCATCTGCCTGC |
| | | SEQ ID NO 823 | CTGTGTCTCGTCTGCCTGC |
| 92 | NPPB | SEQ ID NO 585 | ttctctggaaggggagtgacatc |
| | | SEQ ID NO 586 | ttctctggaagaggagtgacatc |
| | | SEQ ID NO 824 | attctctggaaggggagtgacatca |
| | | SEQ ID NO 825 | attctctggaagaggagtgacatca |
| 93 | ADRB2 | SEQ ID NO 826 | CCTTCTCCTGGGGCTGGCCCG |
| | | SEQ ID NO 827 | CCTTCTCCTGAGGCTGGCCCG |
| | | SEQ ID NO 826 | CCTTCTCCTGGGGCTGGCCCG |

Figure 2C (cont.)

| | | | |
|---|---|---|---|
| | | SEQ ID NO 827 | CCTTCTCCTGAGGCTGGCCCG |
| 94 | TNSALP (ALPL) | SEQ ID NO 593 | TCAAACCGAGATACAAGGTAGCC |
| | | SEQ ID NO 594 | TCAAACCGAGACACAAGGTAGCC |
| | | SEQ ID NO 595 | GGCTACCTTGTATCTCGGTTTGA |
| | | SEQ ID NO 596 | GGCTACCTTGTGTCTCGGTTTGA |
| 95 | ALOX5AP | SEQ ID NO 597 | CATGACCAGCACGAGCCCAGCAC |
| | | SEQ ID NO 598 | CATGACCAGCATGAGCCCAGCAC |
| | | SEQ ID NO 599 | GTGCTGGGCTCGTGCTGGTCATG |
| | | SEQ ID NO 600 | GTGCTGGGCTCATGCTGGTCATG |
| 96 | FDPS | SEQ ID NO 601 | ACTCCCACCCCAGCCTTAGCCCA |
| | | SEQ ID NO 602 | ACTCCCACCCCGCCTTAGCCCA |
| | | SEQ ID NO 603 | TGGGCTAAGGCTGGGGTGGGAGT |
| | | SEQ ID NO 604 | TGGGCTAAGGCGGGGGTGGGAGT |
| 97 | ALOX15 | SEQ ID NO 605 | AATAAGTGACATATTGGCTGCAG |
| | | SEQ ID NO 606 | AATAAGTGACACATTGGCTGCAG |
| | | SEQ ID NO 607 | CTGCAGCCAATATGTCACTTATT |
| | | SEQ ID NO 608 | CTGCAGCCAATGTGTCACTTATT |
| 98 | BMP 4 | SEQ ID NO 609 | CAATCCTGGCATGTTCCTTAAAC |
| | | SEQ ID NO 610 | CAATCCTGGCACGTTCCTTAAAC |
| | | SEQ ID NO 611 | GTTTAAGGAACATGCCAGGATTG |
| | | SEQ ID NO 612 | GTTTAAGGAACGTGCCAGGATTG |
| 99 | BMP 4 | SEQ ID NO 613 | CCTTCCCCCTCTCCGGAATTCAC |
| | | SEQ ID NO 614 | CCTTCCCCCTCCCCGGAATTCAC |
| | | SEQ ID NO 615 | GTGAATTCCGGAGAGGGGGAAGG |
| | | SEQ ID NO 616 | GTGAATTCCGGGGAGGGGGAAGG |
| 104 | MKP1 | SEQ ID NO 633 | GCCTCCAGCGTCCAGGGTGCCCA |
| | | SEQ ID NO 634 | GCCTCCAGCGTTCAGGGTGCCCA |
| | | SEQ ID NO 635 | GCCTCCAGCGTCCAGGGTGCCCA |
| | | SEQ ID NO 636 | GCCTCCAGCGTTCAGGGTGCCCA |
| 105 | MKP1 | SEQ ID NO 637 | CCGAGTCTCCAATTGTAGGCTCT |
| | | SEQ ID NO 638 | CCGAGTCTCCAGTTGTAGGCTCT |
| | | SEQ ID NO 639 | AGAGCCTACAATTGGAGACTCGG |
| | | SEQ ID NO 640 | AGAGCCTACAACTGGAGACTCGG |
| 106 | MKP1 | SEQ ID NO 641 | TGGGCAGTGCGTATCACGCTTCC |
| | | SEQ ID NO 642 | TGGGCAGTGCGCATCACGCTTCC |
| | | SEQ ID NO 643 | GGGCAGTGCGTATCACGCTTC |
| | | SEQ ID NO 644 | GGGCAGTGCGCATCACGCTTC |
| 108 | PPARG | SEQ ID NO 649 | TGTTTTGTCTTCATGGAAAATAC |
| | | SEQ ID NO 650 | TGTTTTGTCTTGATGGAAAATAC |
| | | SEQ ID NO 651 | TGTTTTGTCTTCATGGAAAATAC |
| | | SEQ ID NO 652 | TGTTTTGTCTTGATGGAAAATAC |
| 109 | PPARG | SEQ ID NO 653 | GTCACGGAACACGTGCAGCTACT |
| | | SEQ ID NO 654 | GTCACGGAACATGTGCAGCTACT |
| | | SEQ ID NO 828 | TCACGGAACACGTGCAGCTAC |
| | | SEQ ID NO 829 | TCACGGAACATGTGCAGCTAC |
| 110 | POMC | SEQ ID NO 657 | TGCGGTGAGCCAAGATCGCGCCA |
| | | SEQ ID NO 658 | TGCGGTGAGCCGAGATCGCGCCA |
| | | SEQ ID NO 659 | TGGCGCGATCTTGGCTCACCGCA |
| | | SEQ ID NO 660 | TGGCGCGATCTCGGCTCACCGCA |
| 111 | BMP6 | SEQ ID NO 661 | AACCAATACCAGGGGCAGTGGGA |
| | | SEQ ID NO 662 | AACCAATACCAAGGGCAGTGGGA |

Figure 2C (cont.)

| | | | |
|---|---|---|---|
| | | SEQ ID NO 663 | TCCCACTGCCCCTGGTATTGGTT |
| | | SEQ ID NO 664 | TCCCACTGCCCTTGGTATTGGTT |
| 112 | BMP6 | SEQ ID NO 665 | GACACGGGGGACAAAGGTCCTTT |
| | | SEQ ID NO 666 | GACACGGGGGATAAAGGTCCTTT |
| | | SEQ ID NO 667 | AAAGGACCTTTGTCCCCCGTGTC |
| | | SEQ ID NO 668 | AAAGGACCTTTATCCCCCGTGTC |

Figure 3A: Table 3A

| # SNP | Gene Symbol | ID Number | Sequence |
|---|---|---|---|
| 1 | VDR | SEQ ID NO 1 | AGGGCGAATCATGTATGAGG |
| | | SEQ ID NO 2 | TCAAAGTCTCCAGGGTCAGG |
| 2 | VDR | SEQ ID NO 3 | CCTCACTGCCCTTAGCTCTG |
| | | SEQ ID NO 4 | CCCGCAAGAAACCTCAAATA |
| 3 | VDR | SEQ ID NO 5 | AGCTCCTGTGCCTTCTTCTCT |
| | | SEQ ID NO 6 | TCGGCTAGCTTCTGGATCAT |
| 4 | ESR1 | SEQ ID NO 7 | AGGGTTATGTGGCAATGACG |
| | | SEQ ID NO 8 | ACCAATGCTCATCCCAACTC |
| 5 | ESR2 | SEQ ID NO 9 | CCAAATGTCCCAGCTGTTTT |
| | | SEQ ID NO 10 | CCTGCACCAGAATATGTTACCT |
| 6 | ESR2 | SEQ ID NO 11 | ACACACAGGGAGCTGAGGAG |
| | | SEQ ID NO 12 | CCAGAACAAGATCTGGAGCA |
| 7 | CYP19 | SEQ ID NO 13 | GGGCCATCATTTTCAGGATA |
| | | SEQ ID NO 14 | AGCTGTTATCAGCGGTCCTG |
| 8 + 9 | CYP19 | SEQ ID NO 15 | CAGCAAGGATTTGAAAGATGC |
| | | SEQ ID NO 16 | TGTGGCATGGGAATTACAGT |
| 10 | CYP19 | SEQ ID NO 17 | GTGAGGCGGTAGAGTTGGAG |
| | | SEQ ID NO 18 | TGGCAGAAGGAAGAGGAGAG |
| 11 | CYP19 | SEQ ID NO 19 | CCTTGCACCCAGATGAGACT |
| | | SEQ ID NO 20 | GGCAAGGATGGATGATTTGT |
| 12 | Coll1A1 | SEQ ID NO 21 | AGCCGCTCCCATTCTCTTAG |
| | | SEQ ID NO 22 | GCGTGGTAGAGACAGGAGGA |
| 13 | Coll1A2 | SEQ ID NO 23 | ATCCGTGGCAGCATCATAAG |
| | | SEQ ID NO 24 | TTCTTACAGTGGGGCCTTTG |
| 14 | Coll1A2 | SEQ ID NO 25 | TCACACATCTAGAGGTTAGAAAGTCA |
| | | SEQ ID NO 26 | TCTGATTTAGATATAGGGGAAATATGG |
| 15 | PTH | SEQ ID NO 27 | CTCGTGAAAACCAACCCAAT |
| | | SEQ ID NO 28 | CCAATTCCAAGGCAAAACAG |
| 16 | PTH | SEQ ID NO 29 | CTGTTTTGCCTTGGAATTGG |
| | | SEQ ID NO 30 | GCTTCTTACGCAGCCATTCT |
| 17 | PTH | SEQ ID NO 31 | ACAATTTTGTTGCCCTTGGA |
| | | SEQ ID NO 32 | TGTTTTCATTTTCACTGGGATTT |
| 18 | LRP-5 | SEQ ID NO 33 | GACACACTGGAGGCTGTCAC |
| | | SEQ ID NO 34 | GTGTAGAAAGGCTCGCTTGG |
| 19 | LRP-5 | SEQ ID NO 35 | ATGGCCACGTCGTTGTTATT |
| | | SEQ ID NO 36 | AGCCACCTGTGCTTCTTCAC |
| 20 | LRP-5 | SEQ ID NO 37 | ACATGAAGACCTGCATCGTG |
| | | SEQ ID NO 38 | TGTGGTTGTTGGACACATCA |
| 21 | LRP-5 | SEQ ID NO 39 | GAGCACGTGGTGGAGTTTG |
| | | SEQ ID NO 40 | TTGTCCAAGTCCCTCCACAC |
| 22 | LRP-5 | SEQ ID NO 41 | ACTTCACCAACATGCAGGAC |
| | | SEQ ID NO 42 | CAGGTCACAGCTCTCAATGC |
| 23 | LRP-5 | SEQ ID NO 43 | GGGTCAGTGTGTGGACCTG |
| | | SEQ ID NO 44 | GCAGCCCCAAGCTCGTAT |
| 24 | LCT | SEQ ID NO 45 | CTCCTGACCTCAGGTGATCC |
| | | SEQ ID NO 46 | AAGAAGTCAGAATACCCCTACCC |
| 25 | LCT | SEQ ID NO 47 | CTGCGCTGGCAATACAGATA |
| | | SEQ ID NO 48 | GCTTTGGTTGAAGCGAAGAT |

Figure 3A (cont.)

| | | | | |
|---|---|---|---|---|
| 26 | CYP17 | SEQ ID NO 49 | GGGCTCCAGGAGAATCTTTC | |
| | | SEQ ID NO 50 | AGGGTAAGCAGCAAGAGAGC | |
| 27 | CaSR | SEQ ID NO 51 | CAGATGCAAGCAGAAGGTCA | |
| | | SEQ ID NO 52 | GGTCCTTGCAGACCTGTTTC | |
| 28 | AR | SEQ ID NO 53 | CAACTCCTTCAGCAACAGCA | |
| | | SEQ ID NO 54 | GACACCGACACTGCCTTACA | |
| 29 | IL-6 | SEQ ID NO 55 | GCCTCAATGACGACCTAAGC | |
| | | SEQ ID NO 56 | GCCTCAGACATCTCCAGTCC | |
| 30 | IL-1b | SEQ ID NO 57 | AAACAGCGAGGGAGAAACTG | |
| | | SEQ ID NO 58 | AGGCAGAGAGGGAAGGAGAG | |
| 31 | IL-1b | SEQ ID NO 59 | TGTTCTTAGCCACCCCACTC | |
| | | SEQ ID NO 60 | GTGATCGTACAGGTGCATCG | |
| 32 | TGF-B1 | SEQ ID NO 61 | TGGGAGGTGCTCAGTAAAGG | |
| | | SEQ ID NO 62 | ACCCAGAACGGAAGGAGAGT | |
| 33 | TGF-B1 | SEQ ID NO 63 | TCGATAGTCTTGCAGGTGGA | |
| | | SEQ ID NO 64 | ACCACACCAGCCCTGTTC | |
| 34 | IL-10 | SEQ ID NO 65 | TTCCCCAGGTAGAGCAACAC | |
| | | SEQ ID NO 66 | GATGGGGTGGAAGAAGTTGA | |
| 35 | ESR2 | SEQ ID NO 67 | cggcagaggacagtaaaagc | |
| | | SEQ ID NO 68 | gtggagggaaggatggtaca | |
| 36 | LRP-5 | SEQ ID NO 69 | cgcagtggacttccagtttt | |
| | | SEQ ID NO 70 | gatgcggttggtctctgagt | |
| 37 | LRP-5 | SEQ ID NO 71 | cgctgagtccctctcaactt | |
| | | SEQ ID NO 72 | cggggatacagtcgatctc | |
| 38 | CYP1A1 | SEQ ID NO 73 | CTCACCCCTGATGGTGCTAT | |
| | | SEQ ID NO 74 | TTTGGAAGTGCTCACAGCAG | |
| 39 | CTR | SEQ ID NO 75 | CTGGCGACATCCCAATTTAC | |
| | | SEQ ID NO 76 | CATGGTCTTTCTCCCAGGAA | |
| 40 | OPG | SEQ ID NO 77 | GCACTTTGCTCTAGGGTTCG | |
| | | SEQ ID NO 78 | TCCTTCCCTTGAATCTGGTG | |
| 41 | OPG | SEQ ID NO 79 | ATAACCTTGCGGAGCACTGT | |
| | | SEQ ID NO 80 | AGACAGCGAACCCTAGAGCA | |
| 42 | OPG | SEQ ID NO 81 | CTCCCTGGGGGATCCTTT | |
| | | SEQ ID NO 82 | AGGAAGTATCGCCTGCCTTT | |
| 43 | OPG | SEQ ID NO 83 | AGGTGCAAAGTTTGGTCCAG | |
| | | SEQ ID NO 84 | CCCAGGGACTTACCACGAG | |
| 44 | OPG | SEQ ID NO 85 | CCAACAGGGAAACAAGATCC | |
| | | SEQ ID NO 86 | GGCAACACAGCTCACAAGAA | |
| 45 | TNFa | SEQ ID NO 87 | ACCTGGTCCCCAAAAGAAAT | |
| | | SEQ ID NO 88 | AAAGTTGGGGACACACAAGC | |
| 46 | TNFa | SEQ ID NO 89 | CAGAGGGAAGAGGTGAGTGC | |
| | | SEQ ID NO 90 | GCCAGACATCCTGTCTCTCC | |
| 47 | MTHFR | SEQ ID NO 91 | GCCTCTCCTGACTGTCATCC | |
| | | SEQ ID NO 92 | TCACAAAGCGGAAGAATGTG | |
| 48 | COMT | SEQ ID NO 93 | CATCACCATCGAGATCAACC | |
| | | SEQ ID NO 94 | ACTTTGTCCTCCCCACCAG | |
| 49 | IL-1RA | SEQ ID NO 95 | GGAATCCATGGAGGGAAGAT | |
| | | SEQ ID NO 96 | tgaatgcagcttccaaagtg | |
| 50 | TNFR2 (TNFRSF1B) | SEQ ID NO 97 | CTCTCCTATCCTGCCTGCTG | |
| | | SEQ ID NO 98 | GGCTGGGGTAAGTGTACTGC | |

Figure 3A (cont.)

| | | | | |
|---|---|---|---|---|
| 51 + 52 | SRD5A2 | SEQ ID NO 99 | AGCACACGGAGAGCCTGA | |
| | | SEQ ID NO 100 | AGGGGAAAAACGCTACCTGT | |
| 53 | RUNX 2 | SEQ ID NO 101 | acagcagcagcaacagca | |
| | | SEQ ID NO 102 | ACAGGAAGTTGGGGCTGTC | |
| 54 | PPARA | SEQ ID NO 103 | AGTAAAGCAAGTGCGCTGGT | |
| | | SEQ ID NO 104 | AACGAACTGGGAAAATGTGC | |
| 55 | P2X7Receptor | SEQ ID NO 105 | TCCTGGTAGAGCAGGAGGAA | |
| | | SEQ ID NO 106 | TTCCTGGACAACCAGAGGAG | |
| 56 | ADRB2 | SEQ ID NO 107 | GCTCACCTGCCAGACTGC | |
| | | SEQ ID NO 108 | GCCAGGACGATGAGAGACAT | |
| 57 | ADRB2 | SEQ ID NO 109 | GCTCACCTGCCAGACTGC | |
| | | SEQ ID NO 110 | GCCAGGACGATGAGAGACAT | |
| 58 | ADRB1 | SEQ ID NO 111 | CCGCAGCCCCGACTTC | |
| | | SEQ ID NO 112 | GCCGGTCTCCGTGGGT | |
| 59 | ADRB2 | SEQ ID NO 113 | ATCGCAGTGGATCGCTACTT | |
| | | SEQ ID NO 114 | CAGGTCTCATTGGCATAGCA | |
| 60 | ADRB2 | SEQ ID NO 115 | ACAAGCTGAGTGTGCAGGAC | |
| | | SEQ ID NO 116 | CACACCTCGTCCCTTTCCT | |
| 61 | ADRB1 | SEQ ID NO 117 | AGCCCGGTAACCTGTCGT | |
| | | SEQ ID NO 118 | CACGATCACCAGCACATTG | |
| 62 | ADRB3 | SEQ ID NO 119 | CAATACCGCCAACACCAGT | |
| | | SEQ ID NO 120 | AACACGTTGGTCATGGTCTG | |
| 63 | RANK (TNFRSF11A) | SEQ ID NO 121 | CCAAAGCACTGAACCACCTT | |
| | | SEQ ID NO 122 | CTGGGGCACATCTATCAACC | |
| 64 | ALOX5 | SEQ ID NO 123 | aagaacagcgttggtggatt | |
| | | SEQ ID NO 124 | attcttttcccattgcgttg | |
| 65 | ALOX5 | SEQ ID NO 125 | aagaacagcgttggtggatt | |
| | | SEQ ID NO 126 | cttttcccattgcgttgtct | |
| 66 | ALOX5AP | SEQ ID NO 127 | TCATGAATCACTGGCAGGAA | |
| | | SEQ ID NO 128 | GACTGTGACCTTGGCCACTT | |
| 67 | ALOX12 | SEQ ID NO 129 | AGTTCCTCAATGGTGCCAAC | |
| | | SEQ ID NO 130 | CTGCAGCCTTCCTCTGACTC | |
| 68 | ALOX12 | SEQ ID NO 131 | CTCTGTTTCCCCAAGAATGC | |
| | | SEQ ID NO 132 | GTGCGTGTTCAGCAAGTGAT | |
| 69 | COX1 (PTGS1) | SEQ ID NO 133 | GTACCTAGGAGGGGCTCAGG | |
| | | SEQ ID NO 134 | TCCTTAAAGAGCCGCAGTTG | |
| 70 | COX1 (PTGS1) | SEQ ID NO 135 | TGGCATGAAACCCTACACCT | |
| | | SEQ ID NO 136 | CTCCAAACCCAGCTGAAAAG | |
| 71 | COX2 (PTGS2) | SEQ ID NO 137 | tgaaggtagctatttcattccaca | |
| | | SEQ ID NO 138 | ccgtgtctggtctgtacgtc | |
| 72 | COX2 (PTGS2) | SEQ ID NO 139 | TGCTGTGGAGCTGTATCCTG | |
| | | SEQ ID NO 140 | GAAAACCCACTTCTCCACCA | |
| 73 | LRP6 | SEQ ID NO 141 | GCTGGAGCACAGGACACTTA | |
| | | SEQ ID NO 142 | CAGTTGGAGTGGTGCTGAAA | |
| 74 | ITGB3 | SEQ ID NO 143 | GCTCTGATTGCTGGACTTCTC | |
| | | SEQ ID NO 144 | CCTCTAGTACTCGGGCCTCA | |
| 75 | CLCN7 | SEQ ID NO 145 | ATGTGCTAGGGGAAGACCTG | |
| | | SEQ ID NO 146 | CCCTGTGCTGTGATGTTGAG | |
| 76 | CLCN7 | SEQ ID NO 147 | AGATCAGCACGAAGGCAACT | |
| | | SEQ ID NO 148 | ggcaacaagagcaaaactcc | |

Figure 3A (cont.)

| | | | | |
|---|---|---|---|---|
| 77 | CLCN7 | SEQ ID NO 149 | CGAAACATGGTCAGCCAGTA | |
| | | SEQ ID NO 150 | CAGGGTGTGATGATGTGGAG | |
| 78 | CLCN7 | SEQ ID NO 151 | ATGCTGTCACTGCTGTCCTG | |
| | | SEQ ID NO 152 | TGCATCTTAGCAGAGGGTGA | |
| 79 | CLCN7 | SEQ ID NO 153 | GCACGAGGGCTCAGTTTC | |
| | | SEQ ID NO 154 | CCATGGCCAACGTCTCTAAG | |
| 80 | RANK (TNFRSF11A) | SEQ ID NO 155 | CCCATCGCAGGACTAACTGT | |
| | | SEQ ID NO 156 | GGATCCATCTGAGGAGGAGA | |
| 81 | PPARG | SEQ ID NO 157 | GAGCGCCCAGATGAGATTAC | |
| | | SEQ ID NO 158 | TCAAAGGAGTGGGAGTGGTC | |
| 82 | KL | SEQ ID NO 159 | GGACGCTCAGGTTCATTCTC | |
| | | SEQ ID NO 160 | CCGAGTGGGAGAAAAGTGAG | |
| 83 | KL | SEQ ID NO 161 | ATGGGGTTGTGACCAAGAAG | |
| | | SEQ ID NO 162 | CACTGGGGTGATGTTGACAC | |
| 84 | PTHR1 | SEQ ID NO 163 | TCTGGGCCTCTTCAGTTGAT | |
| | | SEQ ID NO 164 | GGCCAAAGTGAGAACCAAAG | |
| 85 | PTHR1 | SEQ ID NO 165 | CTGAATCTTGGCCTGATGGT | |
| | | SEQ ID NO 166 | GTGGAACAGCAGGAGAGAGG | |
| 86 | PTHR1 | SEQ ID NO 167 | GCCTCCTAGGTCCCTGTCA | |
| | | SEQ ID NO 168 | GATGGGAGCTAATGCCTCAA | |
| 87 | PTHR1 | SEQ ID NO 169 | TTCGAGACACCCCTCTTCAC | |
| | | SEQ ID NO 170 | CCCACATCCTAGCACATCCT | |
| 88 | BMP 2 | SEQ ID NO 171 | CTTCTAGCGTTGCTGCTTCC | |
| | | SEQ ID NO 172 | AGTGCCTGCGATACAGGTCT | |
| 89 | CYP1B1 | SEQ ID NO 173 | ACCTCTGTCTTGGGCTACCA | |
| | | SEQ ID NO 174 | TCATCACTCTGCTGGTCAGG | |
| 90 | IGF-II | SEQ ID NO 175 | TTGCTCTACCCACCCAAGAC | |
| | | SEQ ID NO 176 | AGATTTTCGGGATGGAACCT | |
| 91 | SOST | SEQ ID NO 177 | GTACCATGCAGCTCCCACTG | |
| | | SEQ ID NO 178 | CCGTGGCATCATTCTTGAAC | |
| 92 | NPPB | SEQ ID NO 179 | tattgctgcccttctctgct | |
| | | SEQ ID NO 180 | aggtggcctggtgattagaa | |
| 93 | ADRB2 | SEQ ID NO 181 | ACCTCCAGCTTTAGCCCTCT | |
| | | SEQ ID NO 182 | GTGACGTACGGGAACTTTCG | |
| 94 | TNSALP (ALPL) | SEQ ID NO 183 | ACCTCGTTGACACCTGGAAG | |
| | | SEQ ID NO 184 | TGGAGGAAAGATTTCCGATG | |
| 95 | ALOX5AP | SEQ ID NO 185 | CTGGCTGTGGTTCAGTGTGT | |
| | | SEQ ID NO 186 | TGGCAGCTTCCAGATTCTCT | |
| 96 | FDPS | SEQ ID NO 187 | GAAGACCCCACAGATCTCA | |
| | | SEQ ID NO 188 | TTTTTGTTCCCTGCGTATCC | |
| 97 | ALOX15 | SEQ ID NO 189 | AAGAAGAGGCATCCACCTGA | |
| | | SEQ ID NO 190 | TCCAGGGTCTTCTCTGCACT | |
| 98 | BMP 4 | SEQ ID NO 191 | GGGCCACAGAAGAAAGAACA | |
| | | SEQ ID NO 192 | AAGCCAAGGAAGGAAAGAGC | |
| 99 | BMP 4 | SEQ ID NO 193 | TGAGCCTTTCCAGCAAGTTT | |
| | | SEQ ID NO 194 | CAGGGAGCAGAGTGTGGATA | |
| 100 | BMP 4 | SEQ ID NO 195 | CCAGGGACCAGTGAAAACTC | |
| | | SEQ ID NO 196 | TCACATTGTGGTGGACCAGT | |
| 101 | CYP19 | SEQ ID NO 197 | TCATCTGCCACTGAAAATGC | |
| | | SEQ ID NO 198 | GCAGCTAACATCCTGTGCAA | |

Figure 3A (cont.)

| 102 | MKP1 | SEQ ID NO 199 | GAGGGAGAGAGGGAGGAG | |
| | | SEQ ID NO 200 | AGAGGGGGAGACGTCATCAG | |
| 103 | MKP1 | SEQ ID NO 201 | GAGGGAGAGAGGGAGGAG | |
| | | SEQ ID NO 202 | AGAGGGGGAGACGTCATCAG | |
| 104 | MKP1 | SEQ ID NO 203 | GGGTCTAGCTTTTCCTCGAA | |
| | | SEQ ID NO 204 | CGTTGAAAGCGAAGAAGGAG | |
| 105 | MKP1 | SEQ ID NO 205 | TATAACGGAGGGGACACAGG | |
| | | SEQ ID NO 206 | GTGCCCATACCCACAAAAAC | |
| 106 | MKP1 | SEQ ID NO 207 | TTTTTGTGGGTATGGGCACT | |
| | | SEQ ID NO 208 | GGACAATTGGCTGAGACGTT | |
| 107 | ESRRAL | SEQ ID NO 209 | TGACCGAATGAAGGTCACTG | |
| | | SEQ ID NO 210 | CGTGAGTCAGTGCAGGACAG | |
| 108 | PPARG | SEQ ID NO 211 | AACCACCCTGAGTCCTCACA | |
| | | SEQ ID NO 212 | CTCCGTCTTCTTGATCACCTG | |
| 109 | PPARG | SEQ ID NO 213 | AACCACCCTGAGTCCTCACA | |
| | | SEQ ID NO 214 | CTCCGTCTTCTTGATCACCTG | |
| 110 | POMC | SEQ ID NO 215 | GTGGCTGAGGCAGGAGAAT | |
| | | SEQ ID NO 216 | GATGGAGTCTTGCTGTGTCG | |
| 111 | BMP6 | SEQ ID NO 217 | TTGGTTTGTCGCCTCTCTCT | |
| | | SEQ ID NO 218 | ACTTTCCCCTCACTCCCACT | |
| 112 | BMP6 | SEQ ID NO 219 | TTGATGGGTGCATCTTTTGA | |
| | | SEQ ID NO 220 | ATCAAGCTCTGGGTGTTTGG | |

Figure 3B: Table 3B

| # SNP | Gene Symbol | ID Number | Sequence |
|---|---|---|---|
| 2 | VDR | SEQ ID NO 674 | GCAACCTGAAGGGAGACGTA |
|  |  | SEQ ID NO 675 | CAGTTCACGCAAGAGCAGAG |
| 15 | PTH | SEQ ID NO 676 | GCTTCTCGTGAAAACCAACC |
|  |  | SEQ ID NO 677 | AATCCAATTCCAAGGCAAAA |
| 16 | PTH | SEQ ID NO 678 | TGTCATGTTGGCAATTTGTTTT |
|  |  | SEQ ID NO 679 | CCTGGGAAGAAGAGAAACAGAG |
| 34 | IL-10 | SEQ ID NO 680 | CACACACAAATCCAAGACAACA |
|  |  | SEQ ID NO 681 | AAGCTTCTGTGGCTGGAGTC |
| 42 | OPG | SEQ ID NO 682 | CACTGTTCCCTTCACCAACC |
|  |  | SEQ ID NO 683 | ACAGCGAACCCTAGAGCAAA |
| 48 | COMT | SEQ ID NO 684 | GGGCCTACTGTGGCTACTCA |
|  |  | SEQ ID NO 685 | GGGTTTTCAGTGAACGTGGT |
| 58 | ADRB1 | SEQ ID NO 686 | GGCCTTCAACCCCATCATCTA |
|  |  | SEQ ID NO 687 | CCGGTCTCCGTGGGTCGCGT3 |
| 61 | ADRB1 | SEQ ID NO 688 | GTCGCCGCCCGCCTCGTT |
|  |  | SEQ ID NO 689 | CCATGCCCGCTGTCCACTGCT |
| 108 | PPARG | SEQ ID NO 690 | gtctcgatgttggcgctatt |
|  |  | SEQ ID NO 691 | tctcttatgaaaggctcaagga |
| 82 | KL (only reverse) | SEQ ID NO 692 | CCTCTAGGATTTCGGCCAGT |

Figure 3C: Table 3C

| # SNP | Gene Symbol | ID number | Sequence |
|---|---|---|---|
| 1 | VDR | SEQ ID NO 1 | AGGGCGAATCATGTATGAGG |
|  |  | SEQ ID NO 2 | TCAAAGTCTCCAGGGTCAGG |
| 2 | VDR | SEQ ID NO 674 | GCAACCTGAAGGGAGACGTA |
|  |  | SEQ ID NO 675 | CAGTTCACGCAAGAGCAGAG |
| 3 | VDR | SEQ ID NO 5 | AGCTCCTGTGCCTTCTTCTCT |
|  |  | SEQ ID NO 6 | TCGGCTAGCTTCTGGATCAT |
| 4 | ESR1 | SEQ ID NO 7 | AGGGTTATGTGGCAATGACG |
|  |  | SEQ ID NO 8 | ACCAATGCTCATCCCAACTC |
| 5 | ESR2 | SEQ ID NO 9 | CCAAATGTCCCAGCTGTTTT |
|  |  | SEQ ID NO 10 | CCTGCACCAGAATATGTTACCT |
| 6 | ESR2 | SEQ ID NO 11 | ACACACAGGGAGCTGAGGAG |
|  |  | SEQ ID NO 12 | CCAGAACAAGATCTGGAGCA |
| 7 | CYP19 | SEQ ID NO 13 | GGGCCATCATTTTCAGGATA |
|  |  | SEQ ID NO 14 | AGCTGTTATCAGCGGTCCTG |
| 8 + 9 | CYP19 | SEQ ID NO 15 | CAGCAAGGATTTGAAAGATGC |
|  |  | SEQ ID NO 16 | TGTGGCATGGGAATTACAGT |
| 10 | CYP19 | SEQ ID NO 17 | GTGAGGCGGTAGAGTTGGAG |
|  |  | SEQ ID NO 18 | TGGCAGAAGGAAGAGGAGAG |
| 11 | CYP19 | SEQ ID NO 19 | CCTTGCACCCAGATGAGACT |
|  |  | SEQ ID NO 20 | GGCAAGGATGGATGATTTGT |
| 12 | Coll1A1 | SEQ ID NO 21 | AGCCGCTCCCATTCTCTTAG |
|  |  | SEQ ID NO 22 | GCGTGGTAGAGACAGGAGGA |
| 13 | Coll1A2 | SEQ ID NO 23 | ATCCGTGGCAGCATCATAAG |
|  |  | SEQ ID NO 24 | TTCTTACAGTGGGGCCTTTG |
| 14 | Coll1A2 | SEQ ID NO 25 | TCACACATCTAGAGGTTAGAAAGTCA |
|  |  | SEQ ID NO 26 | TCTGATTTAGATATAGGGGAAATATGG |
| 15 | PTH | SEQ ID NO 676 | GCTTCTCGTGAAAACCAACC |
|  |  | SEQ ID NO 677 | AATCCAATTCCAAGGCAAAA |
| 16 | PTH | SEQ ID NO 678 | TGTCATGTTGGCAATTTGTTTT |
|  |  | SEQ ID NO 679 | CCTGGGAAGAAGAGAAACAGAG |
| 17 | PTH | SEQ ID NO 31 | ACAATTTTGTTGCCCTTGGA |
|  |  | SEQ ID NO 32 | TGTTTTCATTTTCACTGGGATTT |
| 18 | LRP-5 | SEQ ID NO 33 | GACACACTGGAGGCTGTCAC |
|  |  | SEQ ID NO 34 | GTGTAGAAAGGCTCGCTTGG |
| 19 | LRP-5 | SEQ ID NO 35 | ATGGCCACGTCGTTGTTATT |
|  |  | SEQ ID NO 36 | AGCCACCTGTGCTTCTTCAC |
| 20 | LRP-5 | SEQ ID NO 37 | ACATGAAGACCTGCATCGTG |
|  |  | SEQ ID NO 38 | TGTGGTTGTTGGACACATCA |
| 21 | LRP-5 | SEQ ID NO 39 | GAGCACGTGGTGGAGTTTG |
|  |  | SEQ ID NO 40 | TTGTCCAAGTCCCTCCACAC |
| 22 | LRP-5 | SEQ ID NO 41 | ACTTCACCAACATGCAGGAC |
|  |  | SEQ ID NO 42 | CAGGTCACAGCTCTCAATGC |
| 23 | LRP-5 | SEQ ID NO 43 | GGGTCAGTGTGTGGACCTG |
|  |  | SEQ ID NO 44 | GCAGCCCCAAGCTCGTAT |
| 24 | LCT | SEQ ID NO 45 | CTCCTGACCTCAGGTGATCC |
|  |  | SEQ ID NO 46 | AAGAAGTCAGAATACCCCTACCC |
| 25 | LCT | SEQ ID NO 47 | CTGCGCTGGCAATACAGATA |
|  |  | SEQ ID NO 48 | GCTTTGGTTGAAGCGAAGAT |

Figure 3C (cont.)

| | | | | |
|---|---|---|---|---|
| 26 | CYP17 | SEQ ID NO 49 | GGGCTCCAGGAGAATCTTTC | |
| | | SEQ ID NO 50 | AGGGTAAGCAGCAAGAGAGC | |
| 27 | CaSR | SEQ ID NO 51 | CAGATGCAAGCAGAAGGTCA | |
| | | SEQ ID NO 52 | GGTCCTTGCAGACCTGTTTC | |
| 28 | AR | SEQ ID NO 53 | CAACTCCTTCAGCAACAGCA | |
| | | SEQ ID NO 54 | GACACCGACACTGCCTTACA | |
| 29 | IL-6 | SEQ ID NO 55 | GCCTCAATGACGACCTAAGC | |
| | | SEQ ID NO 56 | GCCTCAGACATCTCCAGTCC | |
| 30 | IL-1b | SEQ ID NO 57 | AAACAGCGAGGGAGAAACTG | |
| | | SEQ ID NO 58 | AGGCAGAGAGGGAAGGAGAG | |
| 31 | IL-1b | SEQ ID NO 59 | TGTTCTTAGCCACCCCACTC | |
| | | SEQ ID NO 60 | GTGATCGTACAGGTGCATCG | |
| 32 | TGF-B1 | SEQ ID NO 61 | TGGGAGGTGCTCAGTAAAGG | |
| | | SEQ ID NO 62 | ACCCAGAACGGAAGGAGAGT | |
| 33 | TGF-B1 | SEQ ID NO 63 | TCGATAGTCTTGCAGGTGGA | |
| | | SEQ ID NO 64 | ACCACACCAGCCCTGTTC | |
| 34 | IL-10 | SEQ ID NO 680 | CACACACAAATCCAAGACAACA | |
| | | SEQ ID NO 681 | AAGCTTCTGTGGCTGGAGTC | |
| 35 | ESR2 | SEQ ID NO 67 | cggcagaggacagtaaaagc | |
| | | SEQ ID NO 68 | gtggagggaaggatggtaca | |
| 36 | LRP-5 | SEQ ID NO 69 | cgcagtggacttccagtttt | |
| | | SEQ ID NO 70 | gatgcggttggtctctgagt | |
| 37 | LRP-5 | SEQ ID NO 71 | cgctgagtccctctcaactt | |
| | | SEQ ID NO 72 | cggggatacagtcgatctc | |
| 38 | CYP1A1 | SEQ ID NO 73 | CTCACCCCTGATGGTGCTAT | |
| | | SEQ ID NO 74 | TTTGGAAGTGCTCACAGCAG | |
| 39 | CTR | SEQ ID NO 75 | CTGGCGACATCCCAATTTAC | |
| | | SEQ ID NO 76 | CATGGTCTTTCTCCCAGGAA | |
| 40 | OPG | SEQ ID NO 77 | GCACTTTGCTCTAGGGTTCG | |
| | | SEQ ID NO 78 | TCCTTCCCTTGAATCTGGTG | |
| 41 | OPG | SEQ ID NO 79 | ATAACCTTGCGGAGCACTGT | |
| | | SEQ ID NO 80 | AGACAGCGAACCCTAGAGCA | |
| 42 | OPG | SEQ ID NO 682 | CACTGTTCCCTTCACCAACC | |
| | | SEQ ID NO 683 | ACAGCGAACCCTAGAGCAAA | |
| 43 | OPG | SEQ ID NO 83 | AGGTGCAAAGTTTGGTCCAG | |
| | | SEQ ID NO 84 | CCCAGGGACTTACCACGAG | |
| 44 | OPG | SEQ ID NO 85 | CCAACAGGGAAACAAGATCC | |
| | | SEQ ID NO 86 | GGCAACACAGCTCACAAGAA | |
| 45 | TNFa | SEQ ID NO 87 | ACCTGGTCCCCAAAAGAAAT | |
| | | SEQ ID NO 88 | AAAGTTGGGGACACACAAGC | |
| 46 | TNFa | SEQ ID NO 89 | CAGAGGGAAGAGGTGAGTGC | |
| | | SEQ ID NO 90 | GCCAGACATCCTGTCTCTCC | |
| 47 | MTHFR | SEQ ID NO 91 | GCCTCTCCTGACTGTCATCC | |
| | | SEQ ID NO 92 | TCACAAAGCGGAAGAATGTG | |
| 48 | COMT | SEQ ID NO 684 | GGGCCTACTGTGGCTACTCA | |
| | | SEQ ID NO 685 | GGGTTTTCAGTGAACGTGGT | |
| 49 | IL-1RA | SEQ ID NO 95 | GGAATCCATGGAGGGAAGAT | |
| | | SEQ ID NO 96 | tgaatgcagcttccaaagtg | |
| 50 | TNFR2 (TNFRSF1B) | SEQ ID NO 97 | CTCTCCTATCCTGCCTGCTG | |
| | | SEQ ID NO 98 | GGCTGGGGTAAGTGTACTGC | |

Figure 3C (cont.)

| | | | | |
|---|---|---|---|---|
| 51 + 52 | SRD5A2 | SEQ ID NO 99 | AGCACACGGAGAGCCTGA | |
| | | SEQ ID NO 100 | AGGGGAAAAACGCTACCTGT | |
| 53 | RUNX 2 | SEQ ID NO 101 | acagcagcagcaacagca | |
| | | SEQ ID NO 102 | ACAGGAAGTTGGGGCTGTC | |
| 54 | PPARA | SEQ ID NO 103 | AGTAAAGCAAGTGCGCTGGT | |
| | | SEQ ID NO 104 | AACGAACTGGGAAAATGTGC | |
| 55 | P2X7Receptor | SEQ ID NO 105 | TCCTGGTAGAGCAGGAGGAA | |
| | | SEQ ID NO 106 | TTCCTGGACAACCAGAGGAG | |
| 56 | ADRB2 | SEQ ID NO 107 | GCTCACCTGCCAGACTGC | |
| | | SEQ ID NO 108 | GCCAGGACGATGAGAGACAT | |
| 57 | ADRB2 | SEQ ID NO 109 | GCTCACCTGCCAGACTGC | |
| | | SEQ ID NO 110 | GCCAGGACGATGAGAGACAT | |
| 58 | ADRB1 | SEQ ID NO 686 | GGCCTTCAACCCCATCATCTA | |
| | | SEQ ID NO 687 | CCGGTCTCCGTGGGTCGCGT3 | |
| 59 | ADRB2 | SEQ ID NO 113 | ATCGCAGTGGATCGCTACTT | |
| | | SEQ ID NO 114 | CAGGTCTCATTGGCATAGCA | |
| 60 | ADRB2 | SEQ ID NO 115 | ACAAGCTGAGTGTGCAGGAC | |
| | | SEQ ID NO 116 | CACACCTCGTCCCTTTCCT | |
| 61 | ADRB1 | SEQ ID NO 688 | GTCGCCGCCCGCCTCGTT | |
| | | SEQ ID NO 689 | CCATGCCCGCTGTCCACTGCT | |
| 62 | ADRB3 | SEQ ID NO 119 | CAATACCGCCAACACCAGT | |
| | | SEQ ID NO 120 | AACACGTTGGTCATGGTCTG | |
| 63 | RANK (TNFRSF11A) | SEQ ID NO 121 | CCAAAGCACTGAACCACCTT | . |
| | | SEQ ID NO 122 | CTGGGGCACATCTATCAACC | |
| 64 | ALOX5 | SEQ ID NO 123 | aagaacagcgttggtggatt | |
| | | SEQ ID NO 124 | attcttttcccattgcgttg | |
| 65 | ALOX5 | SEQ ID NO 125 | aagaacagcgttggtggatt | |
| | | SEQ ID NO 126 | cttttcccattgcgttgtct | |
| 66 | ALOX5AP | SEQ ID NO 127 | TCATGAATCACTGGCAGGAA | |
| | | SEQ ID NO 128 | GACTGTGACCTTGGCCACTT | |
| 67 | ALOX12 | SEQ ID NO 129 | AGTTCCTCAATGGTGCCAAC | |
| | | SEQ ID NO 130 | CTGCAGCCTTCCTCTGACTC | |
| 68 | ALOX12 | SEQ ID NO 131 | CTCTGTTTCCCCAAGAATGC | |
| | | SEQ ID NO 132 | GTGCGTGTTCAGCAAGTGAT | |
| 69 | COX1 (PTGS1) | SEQ ID NO 133 | GTACCTAGGAGGGGCTCAGG | |
| | | SEQ ID NO 134 | TCCTTAAAGAGCCGCAGTTG | |
| 70 | COX1 (PTGS1) | SEQ ID NO 135 | TGGCATGAAACCCTACACCT | |
| | | SEQ ID NO 136 | CTCCAAACCCAGCTGAAAAG | |
| 71 | COX2 (PTGS2) | SEQ ID NO 137 | tgaaggtagctatttcattccaca | |
| | | SEQ ID NO 138 | ccgtgtctggtctgtacgtc | |
| 72 | COX2 (PTGS2) | SEQ ID NO 139 | TGCTGTGGAGCTGTATCCTG | |
| | | SEQ ID NO 140 | GAAAACCCACTTCTCCACCA | |
| 73 | LRP6 | SEQ ID NO 141 | GCTGGAGCACAGGACACTTA | |
| | | SEQ ID NO 142 | CAGTTGGAGTGGTGCTGAAA | |
| 74 | ITGB3 | SEQ ID NO 143 | GCTCTGATTGCTGGACTTCTC | |
| | | SEQ ID NO 144 | CCTCTAGTACTCGGGCCTCA | |
| 75 | CLCN7 | SEQ ID NO 145 | ATGTGCTAGGGGAAGACCTG | |
| | | SEQ ID NO 146 | CCCTGTGCTGTGATGTTGAG | |
| 76 | CLCN7 | SEQ ID NO 147 | AGATCAGCACGAAGGCAACT | |
| | | SEQ ID NO 148 | ggcaacaagagcaaaactcc | |

Figure 3C (cont.)

| | | | | |
|---|---|---|---|---|
| 77 | CLCN7 | SEQ ID NO 149 | CGAAACATGGTCAGCCAGTA | |
| | | SEQ ID NO 150 | CAGGGTGTGATGATGTGGAG | |
| 78 | CLCN7 | SEQ ID NO 151 | ATGCTGTCACTGCTGTCCTG | |
| | | SEQ ID NO 152 | TGCATCTTAGCAGAGGGTGA | |
| 79 | CLCN7 | SEQ ID NO 153 | GCACGAGGGCTCAGTTTC | |
| | | SEQ ID NO 154 | CCATGGCCAACGTCTCTAAG | |
| 80 | RANK (TNFRSF11A) | SEQ ID NO 155 | CCCATCGCAGGACTAACTGT | |
| | | SEQ ID NO 156 | GGATCCATCTGAGGAGGAGA | |
| 81 | PPARG | SEQ ID NO 157 | GAGCGCCCAGATGAGATTAC | |
| | | SEQ ID NO 158 | TCAAAGGAGTGGGAGTGGTC | |
| 82 | KL | SEQ ID NO 159 | GGACGCTCAGGTTCATTCTC | |
| | | SEQ ID NO 692 | CCTCTAGGATTTCGGCCAGT | |
| 83 | KL | SEQ ID NO 161 | ATGGGGTTGTGACCAAGAAG | |
| | | SEQ ID NO 162 | CACTGGGGTGATGTTGACAC | |
| 84 | PTHR1 | SEQ ID NO 163 | TCTGGGCCTCTTCAGTTGAT | |
| | | SEQ ID NO 164 | GGCCAAAGTGAGAACCAAAG | |
| 85 | PTHR1 | SEQ ID NO 165 | CTGAATCTTGGCCTGATGGT | |
| | | SEQ ID NO 166 | GTGGAACAGCAGGAGAGAGG | |
| 86 | PTHR1 | SEQ ID NO 167 | GCCTCCTAGGTCCCTGTCA | |
| | | SEQ ID NO 168 | GATGGGAGCTAATGCCTCAA | |
| 87 | PTHR1 | SEQ ID NO 169 | TTCGAGACACCCCTCTTCAC | |
| | | SEQ ID NO 170 | CCCACATCCTAGCACATCCT | |
| 88 | BMP 2 | SEQ ID NO 171 | CTTCTAGCGTTGCTGCTTCC | |
| | | SEQ ID NO 172 | AGTGCCTGCGATACAGGTCT | |
| 89 | CYP1B1 | SEQ ID NO 173 | ACCTCTGTCTTGGGCTACCA | |
| | | SEQ ID NO 174 | TCATCACTCTGCTGGTCAGG | |
| 90 | IGF-II | SEQ ID NO 175 | TTGCTCTACCCACCCAAGAC | |
| | | SEQ ID NO 176 | AGATTTTCGGGATGGAACCT | |
| 91 | SOST | SEQ ID NO 177 | GTACCATGCAGCTCCCACTG | |
| | | SEQ ID NO 178 | CCGTGGCATCATTCTTGAAC | |
| 92 | NPPB | SEQ ID NO 179 | tattgctgcccttctctgct | |
| | | SEQ ID NO 180 | aggtggcctggtgattagaa | |
| 93 | ADRB2 | SEQ ID NO 181 | ACCTCCAGCTTTAGCCCTCT | |
| | | SEQ ID NO 182 | GTGACGTACGGGAACTTTCG | |
| 94 | TNSALP (ALPL) | SEQ ID NO 183 | ACCTCGTTGACACCTGGAAG | |
| | | SEQ ID NO 184 | TGGAGGAAAGATTTCCGATG | |
| 95 | ALOX5AP | SEQ ID NO 185 | CTGGCTGTGGTTCAGTGTGT | |
| | | SEQ ID NO 186 | TGGCAGCTTCCAGATTCTCT | |
| 96 | FDPS | SEQ ID NO 187 | GAAGACCCCCACAGATCTCA | |
| | | SEQ ID NO 188 | TTTTTGTTCCCTGCGTATCC | |
| 97 | ALOX15 | SEQ ID NO 189 | AAGAAGAGGCATCCACCTGA | |
| | | SEQ ID NO 190 | TCCAGGGTCTTCTCTGCACT | |
| 98 | BMP 4 | SEQ ID NO 191 | GGGCCACAGAAGAAAGAACA | |
| | | SEQ ID NO 192 | AAGCCAAGGAAGGAAAGAGC | |
| 99 | BMP 4 | SEQ ID NO 193 | TGAGCCTTTCCAGCAAGTTT | |
| | | SEQ ID NO 194 | CAGGGAGCAGAGTGTGGATA | |
| 100 | BMP 4 | SEQ ID NO 195 | CCAGGGACCAGTGAAAACTC | |
| | | SEQ ID NO 196 | TCACATTGTGGTGGACCAGT | |
| 101 | CYP19 | SEQ ID NO 197 | TCATCTGCCACTGAAAATGC | |
| | | SEQ ID NO 198 | GCAGCTAACATCCTGTGCAA | |

Figure 3C (cont.)

| 102 | MKP1 | SEQ ID NO 199 | GAGGGAGAGAGGGAGGAG | |
| --- | --- | --- | --- | --- |
| | | SEQ ID NO 200 | AGAGGGGGAGACGTCATCAG | |
| 103 | MKP1 | SEQ ID NO 201 | GAGGGAGAGAGGGAGGAG | |
| | | SEQ ID NO 202 | AGAGGGGGAGACGTCATCAG | |
| 104 | MKP1 | SEQ ID NO 203 | GGGTCTAGCTTTTCCTCGAA | |
| | | SEQ ID NO 204 | CGTTGAAAGCGAAGAAGGAG | |
| 105 | MKP1 | SEQ ID NO 205 | TATAACGGAGGGGACACAGG | |
| | | SEQ ID NO 206 | GTGCCCATACCCACAAAAAC | |
| 106 | MKP1 | SEQ ID NO 207 | TTTTTGTGGGTATGGGCACT | |
| | | SEQ ID NO 208 | GGACAATTGGCTGAGACGTT | |
| 107 | ESRRAL | SEQ ID NO 209 | TGACCGAATGAAGGTCACTG | |
| | | SEQ ID NO 210 | CGTGAGTCAGTGCAGGACAG | |
| 108 | PPARG | SEQ ID NO 690 | gtctcgatgttggcgctatt | |
| | | SEQ ID NO 691 | tctcttatgaaaggctcaagga | |
| 109 | PPARG | SEQ ID NO 213 | AACCACCCTGAGTCCTCACA | |
| | | SEQ ID NO 214 | CTCCGTCTTCTTGATCACCTG | |
| 110 | POMC | SEQ ID NO 215 | GTGGCTGAGGCAGGAGAAT | |
| | | SEQ ID NO 216 | GATGGAGTCTTGCTGTGTCG | |
| 111 | BMP6 | SEQ ID NO 217 | TTGGTTTGTCGCCTCTCTCT | |
| | | SEQ ID NO 218 | ACTTTCCCCTCACTCCCACT | |
| 112 | BMP6 | SEQ ID NO 219 | TTGATGGGTGCATCTTTTGA | |
| | | SEQ ID NO 220 | ATCAAGCTCTGGGTGTTTGG | |

Figure 4

| | MALES (N=429) | | | FEMALES (N=600) | | |
|---|---|---|---|---|---|---|
| | NORMAL LSBMD | OSTEOPENIC LSBMD | OSTEOPOROTIC LSBMD | NORMAL LSBMD | OSTEOPENIC LSBMD | OSTEOPOROTIC LSBMD |
| LSBMD DIAGNOSIS | 40 | 36 | 24 | 25 | 44 | 30 |
| FRACTURES (%) | 30 | 30 | 45 | 31 | 41 | 60 |
| VERTEBRAL FRACTURES (%) | 8 | 16 | 37 | 5 | 15 | 27 |
| LSBMD | 1,19(0,17) | 0,92 (0,08) | 0,75(0,09) | 1,19 (0,11) | 0,96 (0,05) | 0,77 (0,09) |
| BMI | 27,44(3,38) | 25,96(3,75) | 23,4(2,7) | 26,4 (3,88) | 25,5 (4,14) | 23,9 (3,71) |
| AGE (years) | 66,5(6,7) | 66,3 (8,3) | 65,4 (9,22) | 61,7 (7,8) | 63,35 (7,7) | 66,5 (8,1) |
| MENARCHE AGE (years) | | | | 12,63 (1,56) | 12,68 (1,42) | 13 (1,55) |
| MENOPAUSE AGE (years) | | | | 49 (7,5) | 48,75 (5,7) | 47 (7) |

Table 4. Clinical parameters of 1029 individuals included in the study.
Note: (SD)

Figure 5: Table 5

| Gene Name | Locus | MIM | SNP n° | Restriction Enzyme | rs n° | Location | FEMALES FRACTURES | FEMALES VERTEBRAL FRACTURES | MALES FRACTURES | MALES VERTEBRAL FRACTURES | FEMALES LSBMD | FEMALES FNBMD | MALES LSBMD | MALES FNBMD |
|---|---|---|---|---|---|---|---|---|---|---|---|---|---|---|
| Vitamin D Receptor | 12q13.11 | 601769 | 1 | FokI | rs10735810 | Exon 3 2 T/C | x | x | x | | | | | |
| Vitamin D Receptor | 12q13.11 | | 2 | BsmI | rs1544410 | intr. 9 | x | | | | | | | |
| Vitamin D Receptor | 12q13.11 | | 3 | TaqI | rs731236 | Exon 10 C/T codon 352 | x | | | x | | | | |
| Estrogen Receptor A | 6q25.1 | 133430 | 4 | PvuII | rs2234693 | IVS1-397 T/C | x | x | x | | | | | |
| Estrogen Receptor A | 6q25.1 | | 5 | XbaI | rs9340799 | IVS1-351G/A | x | | | | | | | |
| Estrogen Receptor B | 14q23.2 | 601663 | 6 | RsaI | rs1256049 | ex. 5 (1082 A/G) | | | | | x | | | |
| Aromatase (CYP19) | 15q21.1 | | 10 | | rs3764307 | A/G (int. 8) | | | | | | | | |
| Aromatase (CYP19) | 15q21.1 | | 11 | | rs10046 | A/G (3' UTR) | x | | | | | | x | |
| Collagen type 1 A1 | 17q21.33 | 120150 | 12 | MscI (mut. P) | rs1800012 | G/T (int. 1 Sp1bind.) | x | x | x | | | | | |
| Collagen type 1 A2 | 7q22.1 | 120160 | 13 | PvuII | rs412777 | | x | | | | | | | |
| Collagen type 1 A2 | 7q22.1 | | 14 | EcoRI | rs17166249 | | | | | | | | | |
| PTH | 11p15.3-p15.1 | 168450 | 15 | | rs694 | A/G (int. 1) | | | x | | x | x | | x |
| PTH | 11p15.3-p15.1 | | 16 | BstBI | rs6254 | C/A (ex.3 codon52) | | | | | x | x | | x |
| PTH | 11p15.3-p15.1 | | 17 | DraII | rs6256 | G/A (int.2) | | | | | | | | |
| LRP-5 | 11q13.4 | 600536 | 18 | | rs314776 | IVS4-T/C | x | | x | | | | x | x |
| LRP-5 | 11q13.4 | | 19 | | rs2277268 | G/A (ex9 codon1980) | | x | | | | | | |
| LRP-5 | 11q13.4 | | 20 | | rs4988321 | G/A (ex9 codon2047) | | | | | | x | | |
| LRP-5 | 11q13.4 | | 21 | | rs2306862 | C/T (ex.10 codon2268) | | | | | | | | |
| LRP-5 | 11q13.4 | | 22 | | rs556442 | A/G (ex.15 codon3405) | | x | | | | | x | x |
| LRP-5 | 11q13.4 | | 23 | | rs3736228 | C/T (ex.18 codon4037) | | x | | x | | | | |
| LCT gene (lactose...) | 2q21 | 603202 | 24 | | rs182549 | -22018 G/A | | | | | | | | |
| LCT gene (lactose...) | 2q21 | | 25 | | rs4988236 | -13910 T/C | | | | | | | | |
| CYP17 | 10q24.3 | 608330 | 26 | MspAI | rs743572 | T/C (promoter -34bp) | x | | | | | | | |
| GcSR | 3q13.3-q21 | 601199 | 27 | | rs1801725 | A986S T/G | | x | x | | | | | |
| Androgen Receptor | Xq11-q12 | 313700 | 28 | StuI S1 | rs6152 | G173A (codon211) | | x | | | | | | |
| IL-1b | 7q21 | 147720 | 29 | | rs1800795 | G-174C (promoter) | x | | | | | | | |
| IL-8 | 2q14 | 147620 | 30 | AvaI | rs1799916 | C-511T (promoter) | | | | | | | | |
| IL-1b | 2q14 | 147720 | 31 | TaqI | rs1143634 | C3954T (ex. 5) | | x | | | | | x | x |
| TGF-β1 | 19q13.1 | 190180 | 32 | Bsu36I | rs1800469 | -509 | | | | | | | | |
| TGF-β1 | 19q13.1 | | 33 | | rs17849267 | C/T codon 10 | | x | x | | | | | |
| IL-10 | 1q31-q32 | 124092 | 34 | BclI | rs1800896 | A-1082G | | | | | | | | |
| LRP-5 | 11q13.4 | | 35 | | | A/G (ex2 codon 266) | | | | | | | | |
| LRP-5 | 15q22-q24 | | 36 | | | IVS17-30G/A | | x | x | x | | | x | x |
| LRP-5 | | | 37 | | | C4887A | | x | x | x | | | x | x |
| CYP1A1 | 7q21.3 | 108330 | 38 | | rs1799814 | 1340 T/C (Leu447Pro) | x | x | | | | | | |
| CTR | 8q24.1 | 602643 | 39 | | Rs3102735 | A163G | x | x | | | | | | |
| OPG | 8q24.2 | | 40 | AseI | Rs3134069 | T245G | | x | | | | | x | x |
| OPG | 8q24.3 | | 41 | HindI | Rs2073617 | T950C | | | | | | | | |
| OPG | 8q24.3 | | 42 | HpaI | Rs2073618 | G1181C (ex.1) | | | | | | | | |
| OPG | 8q24.4 | | 43 | SmII | Rs7844539 | A6890C (int.4,-6 ex4) | | x | x | | | | x | x |
| OPG | 8q24.5 | | 44 | BclI | rs1800629 | G-308A (5'UTR) | | x | | | | | x | x |
| TNFalfa | 6p21.3 | 191160 | 45 | | rs1800610 | G489A | | x | x | | | | | |
| TNFalfa | 6p21.3 | | 46 | | Rs1801133 | C677T (ex 4) | | x | x | | | | | |
| MTHFR | 1p36.3 | 607093 | 47 | HinfI | Rs4680 | G158A (Val106Met) | | x | x | | | | | |
| COMT | 22q11.2 | 116790 | 48 | | Rs454078 | A958T | | | | | | | | |
| IL-1RA | 2q14.2 | 147679 | 49 | | Rs1061622 | T676G ex.6 (Met196Arg) | x | | x | | | | x | x |
| TNFR2 (TNFRSF1B) | 1p36.3-p36.2 | 191191 | 50 | | Rs3134069 | G/A Ala49Thr | x | | | | | | | |
| SRD5A2 | 2p23 | 607306 | 51 | | Rs5223349 | G298C (Val89Leu) | x | | | | | | | |
| SRD5A2 | 2p23 | | 52 | RsaI | Rs6921145 | A147G (ex. 1) | | | | | | x | | x |
| RUNX2 | 6p21 | 600211 | 53 | MspA1I | Rs1800206 | C/G ex.5 (Leu162val) | x | x | x | | | x | | |
| PPARalpha | 22q13.31 | 170998 | 54 | | Rs3751143 | Glu499Ala | x | | | | | | | |
| P2X7Receptor | 12q24 | 602566 | 55 | | Rs1042713 | arg19gly | | | | | | | | |
| ADRB2 | 5q31-q32 | | 56 | | Rs1042714 | gln27glu | | | | | | | | |
| ADRB2 | 5q31-q32 | 607093 | 57 | | Rs1801253 | 1158 G/C (gly389arg) | x | | | | | | | |
| ADRB1 | 10q24-q26 | 116790 | 58 | | Rs1800888 | thr164ile | | | | | | | | |
| ADRB2 | 5q31-q32 | | 59 | | Rs1042711 | -42 T/C | | | | | | | | |
| ADRB1 | 10q24-q26 | 109630 | 61 | | Rs1042252 | (Trp64Arg) | | x | | | | | | |
| ADRB3 | 8p12-p11.2 | 109691 | 62 | BstNI | Rs4994 | (ser49gly) | | | | | | | | |

Figure 5 (cont.)

| Gene | Locus | | | rs# | Change | | | | | | |
|---|---|---|---|---|---|---|---|---|---|---|---|
| RANK (TNFRSF11A) | 18q22.1 | | 63 | | C421T (H141I) | | | | | | |
| RANK (TNFRSF11A) | 10q11.2 | 152390 | 64 | Cfol (mod prim) | Rs 1805034 | C575T (V192A ex.6) | | | | | |
| ALOX5 | 10q11.2 | | 65 | | rs6413416 | -1752 G/A | | | | | x |
| ALOX5AP | 13q12 | | 66 | | rs4986832 | -1699 G/A | | | | | |
| ALOX12 | 17p13.1 | 152391 | 67 | | rs2236065 | Glu254Lys | | | | | |
| ALOX12 | 17p13.1 | | 68 | | rs1126667 | Gln261Arg | | | x | | |
| COX1 (PTGS1) | 9q32-q33.3 | 176805 | 69 | | rs434473 | Ser322Asn | | x | | | |
| COX1 (PTGS1) | 9q32-q33.3 | | 70 | | rs5789 | Leu237Met | x | | | | |
| COX2 (PTGS2) | 1q25.2-q25.3 | 600262 | 71 | | rs5794 | Val461Ile | | x | | | |
| COX2 (PTGS2) | 1q25.2-q25.3 | | 72 | | rs20420 | -645 C/T | | | | | |
| LRP6 | 12p11-p13 | 603507 | 73 | | rs5273 | Val61Ala | | | | | |
| INTEGRIN B3 | 17q21.32 | | 74 | | Rs 2302685 | Ile1062Val | | | | | |
| CLCN7 | 16p13 | 602727 | 75 | | Rs 5918 | Leu39Pro | x | | | | x |
| CLCN7 | 16p13 | | 76 | | rs4294542 | A>G UTR | x | x | | | x |
| CLCN7 | 16p13 | | 77 | | rs12926069 | V416M C>T | x | | | | x |
| CLCN7 | 16p13 | | 78 | | rs2235579 | Silent A390A | x | | | | x |
| RANKL (TNFRSF11) | 13q14 | 603499 | 79 | | rs2235580 | intron C>T | | | | | |
| PPARG | 3p25 | 601487 | 80 | | rs3751884 | A>G Silent P42P | | | | | |
| KL (Klotho Gene) | 13q12 | 604824 | 81 | Rsal | Rs2277438 | C421T (H141I ex.4) | x | | | | |
| KL (Klotho Gene) | 13q12 | | 82 | | rs1805192 | C/G ex 2 (Pro12Ala) | | | | | |
| PTHR1 | 3p22-p21.1 | 168468 | 83 | | rs1207568 | G395A promoter | | | | | |
| PTHR1 | 3p22-p21.1 | | 84 | | rs564481 | C1818T end | x | | | | |
| PTHR1 | 3p22-p21.1 | | 85 | | rs724449 | C52813T (nt2 + 182bp ex2) | | x | | | |
| BMP 2 | 2p12.3 | 112261 | 86 | | rs2247116 | A56250G (nt8 + 170bp ex6) | | | | x | |
| CYP1B1 | 2p22-p21 | 601771 | 87 | | rs1531137 | T60182C (nt10 + 58bp ex10) | | | | | |
| IGF-II | 11p15.5 | 147470 | 88 | | rs1899072 | T61407C (nt13 + 36bp ex13) | x | | | x | |
| SOST | 17q12-q21 | 605740 | 89 | | Rs 2273073 | Ser37Ala (ex.2 A/T) | | | | x x | |
| NPPB (BNP gene) | 1p36.2 | 600295 | 90 | | Rs 1056836 | G1294C | | | x | | |
| AD1B2 | 5q31-q32 | 109690 | 91 | | Rs 2230949 | C266T (3'-UTR) | x | | x | | |
| TNSALP (ALPL) | 1p36.1-p34 | 171760 | 92 | | Rs 17782143 | G11988A (Val to Ile) | x | | | | |
| ALOX15 | 17p13.3 | | 93 | | | C-1583T | | | | | |
| ALOX5AP | 13q12 | | 94 | | Rs 11969427 | -367 T/C | | | | x | |
| FDPS | 3 | | 95 | | rs3200254 | 787T/C (Tyr246Mfs) | x | | | | |
| BMP 4 | 14q22-q23 | 112262 | 96 | | Rs 748694 | -5229 G>A | x | | | x | |
| BMP 4 | 14q22-q23 | | 97 | | rs9550373 | -336 G/A | x | | | x | |
| Aromatase (CYP19) | 15q21.1 | | 98 | | rs2297480 | CT | | | | x | |
| MKP1 | 5q34 | | 99 | | Rs 1957860 | -5026 G>A | | | | x | |
| MKP1 | 5q34 | | 100 | | Rs 2855532 | 3564 C>T | x | | | | |
| ESRRA7KCNK4 | 14q22-q23 | | 101 | | rs4775936 | C/T (5'UTR ex 1,2) | | | | | |
| BMP 4 | 14q22-q23 | | 102 | | rs61152 | CT | | | | | |
| MKP1 | 5q34 | | 103 | | rs2070996 | CT | | | | | |
| MKP1 | 5q34 | | 104 | | Rs3217060 | BCGGTGACCGAATGAAGGTCAC | | | | | |
| PPARG | 3p25 | | 105 | | Rs 17563 | 6007 C>T | x | | | x | |
| PPARG | 3p25 | | 106 | | rs12521930 | Ala56Thr (ex1) G/A | x | | | | |
| POMC | 2p23.3 | | 107 | | rs7702178 | (A/G int2) | x | | | | |
| BMP6 | 6p24-p23 | | 108 | | rs10865710 | Tyr107His (ex3) | x | | | x | |
| BMP6 | 6p24-p23 | | 109 | | rs3856806 | 681C/G promoter | x | | | x | |
| Estrogen Receptor B | 14q23.2 | | 110 | | rs3754863 | CT ex.7 | | | | x x | |
| Aromatase (CYP19) | 15q21.1 | 107910 | 111 | | | 5-2353A (promoter) | | | | | |
| Aromatase (CYP19) | 15q21.1 | | 35 | Alu I | rs1062033 | IVS4-6835 A/G | x | | x | | x |
| CLINICAL VARIABLES | | | 7 | | rs700519 | ex 8 (1730 G/A) | | | | | |
| AGE | | | 8 | StaNI | | C/G (5'UTR ex 1,2) | | | | | |
| MENARCA AGE | | | 9 | StaNI | rs700519 | CT ex.7 | x x | | x | x | x |
| MENOPAUSIA AGE | | | | | | | x | | x | | x |
| BMI | | | | | | | x | | | | x |

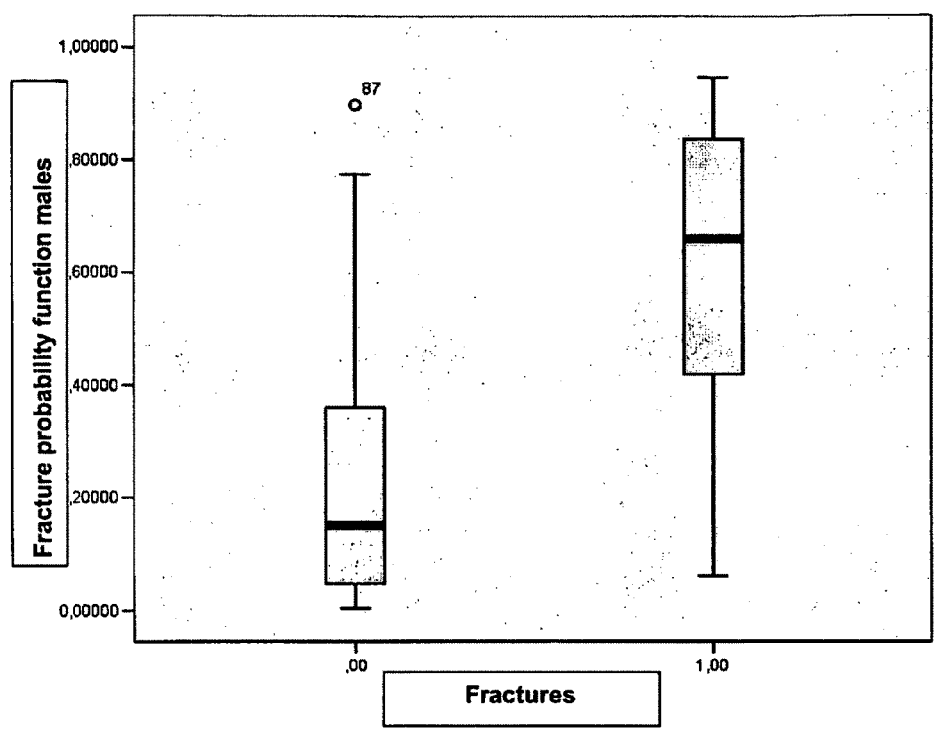
Figure 6.1

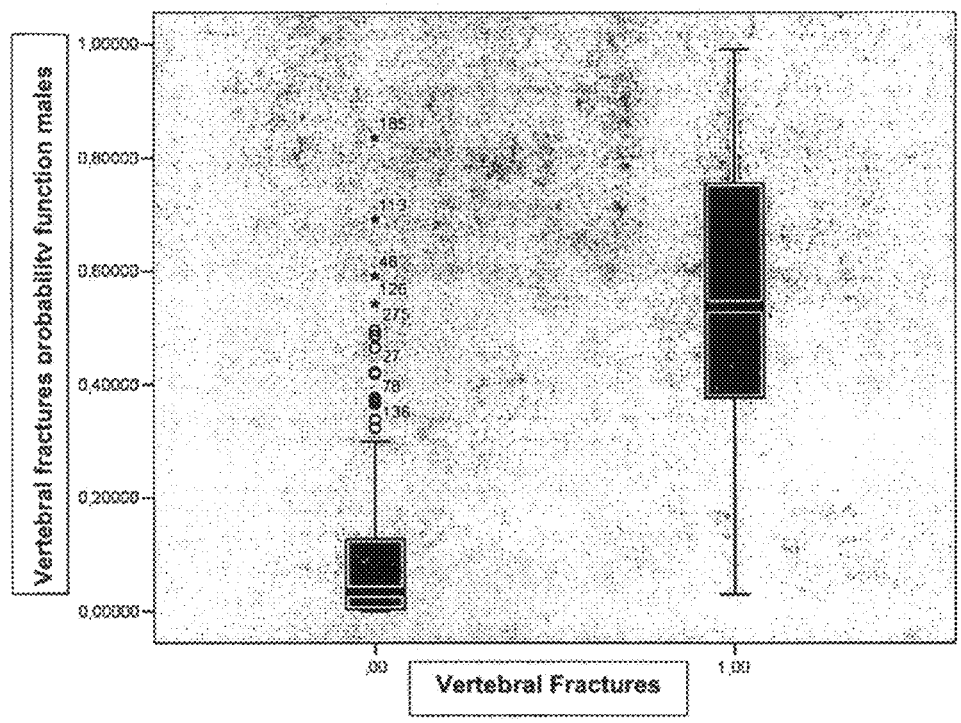
Figure 6.2

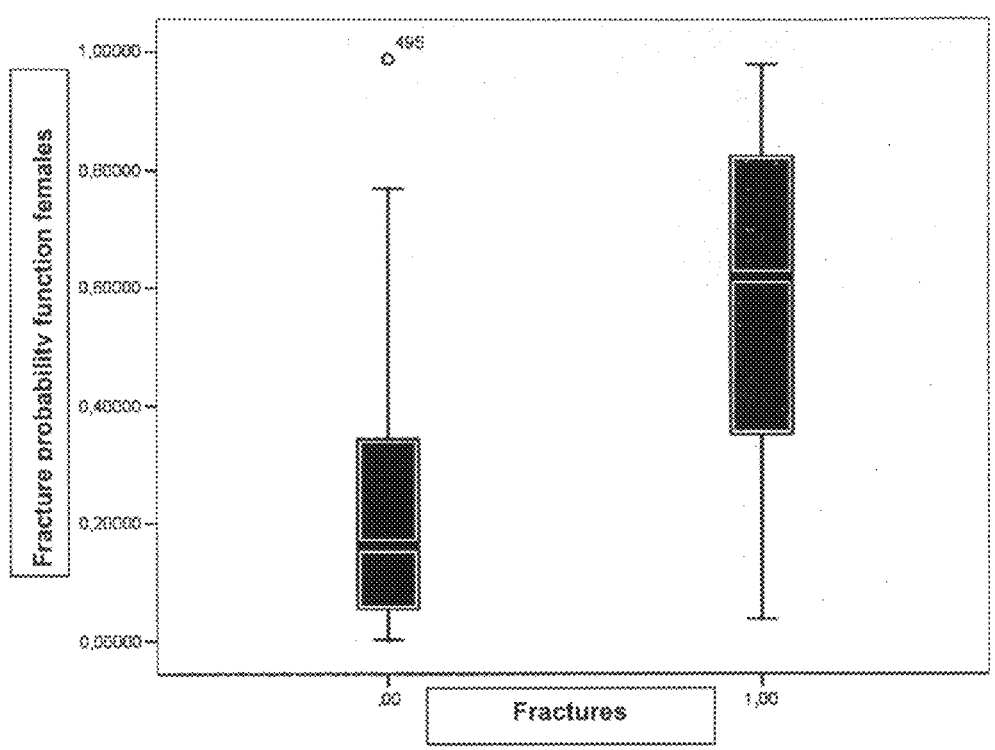
Figure 7.1

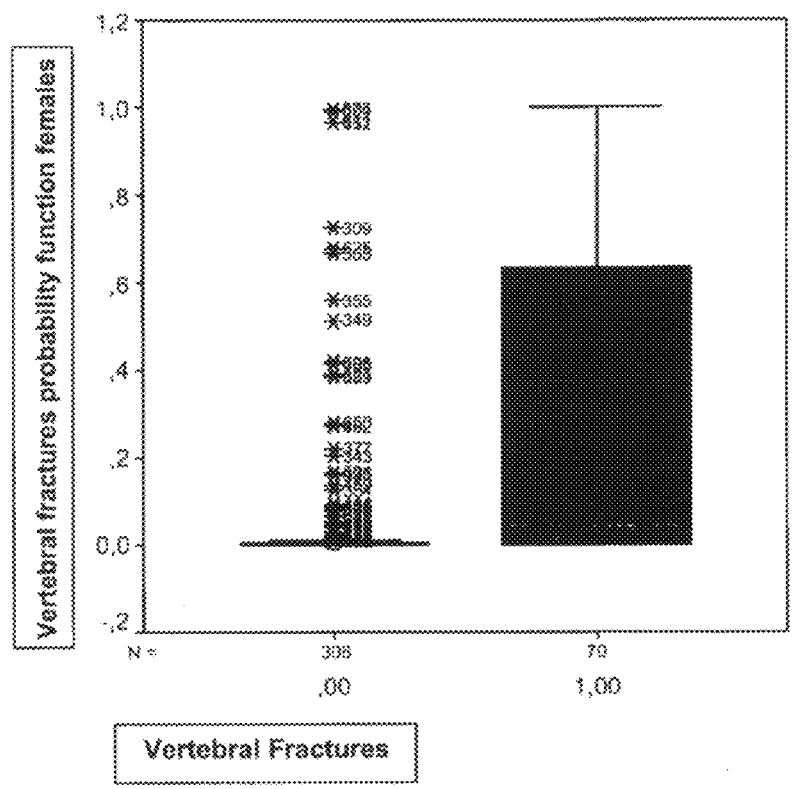
Figure 7.2

Figure 8

|  | LSBMD-FEMALES | FNBMD-FEMALES | LSBMD-MALES | FNBMD-MALES |
|---|---|---|---|---|
| $R^2$ | 0.3 | 0.32 | 0.38 | 0.35 |

$R^2$ for quantitative models.

| VARIABLES | General Model | | Male Model | | Female Model | |
|---|---|---|---|---|---|---|
| | FSTEP | BSTEP | FSTEP | BSTEP | FSTEP | BSTEP |
| | rs2234693 | rs2234693 | rs3736228 | rs9550373 | rs412777 | rs2234693 |
| | rs412777 | rs412777 | | rs9340799 | rs592849 | rs12926089 |
| | rs4680 | rs4680 | | rs523349 | rs1805034 | rs592849 |
| | rs12926089 | rs7702178 | | rs4680 | rs523349 | rs9550373 |
| | rs523349 | rs724449 | | rs5918 | rs6256 | rs1805034 |
| | | rs12926089 | | rs2073618 | rs1800012 | rs523349 |
| | | rs592849 | | rs724449 | | rs2230949 |
| | | rs523349 | | rs3736228 | | rs6256 |
| | | rs1869872 | | rs6152 | | rs1800012 |
| | | | | | | rs1061622 |
| | | | | | | rs7702178 |
| CLINICAL | AGE | AGE | AGE | AGE | AGE | AGE |

Figure 9

ROC curve for General model, FSTEP selection

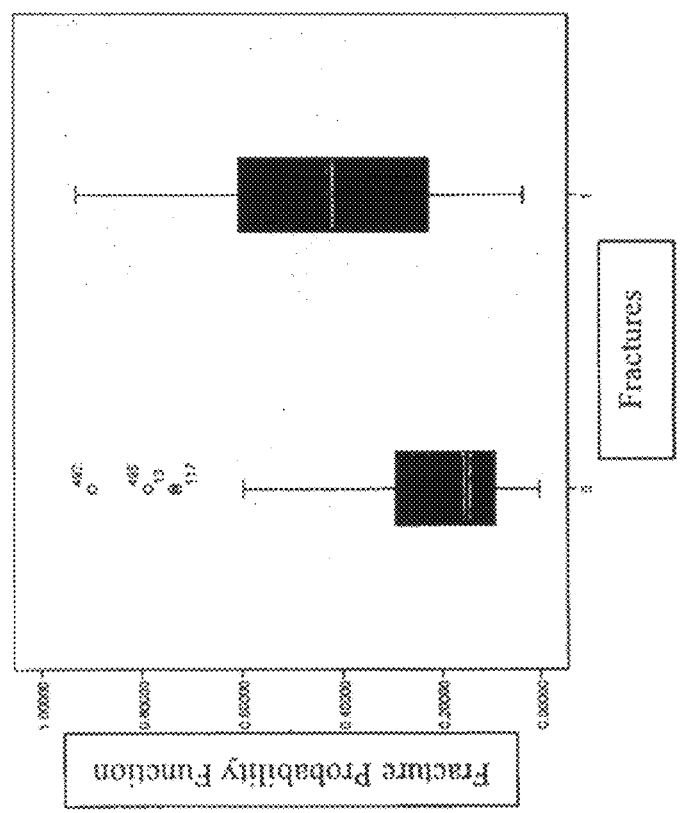

ROC curve for Male model, BSTEP selection

ROC curve for Female model, FSTEP selection

Sensitivity, specificity, and positive likelihood ratio (LR+ =sensitivity/(1-specificity)) for the Fracture model computed by means of Receiver Operating Characteristic curves.

| Variable selection method | Sensitivity | Specificity | LR+ | ROC-AUCs |
|---|---|---|---|---|
| *Vertebral, Femoral or Wrist Fractures (N = 553)* | | | | |
| Fractures in any of the three places or otherwise | | | | |
| Forward selection | 37.7% | 95.1% | 7.7 | 0.783 |
| Backstep selection | 38.4% | 95.1% | 7.8 | 0.81 |
| *Vertebral, Femoral or Wrist Fractures for males only (N = 174)* | | | | |
| Fractures in any of the three places or otherwise | | | | |
| Forward selection | 27.80% | 94.90% | 5.5 | 0.686 |
| Backstep selection | 44.40% | 94.90% | 8.7 | 0.868 |
| *Vertebral, Femoral or Wrist Fractures for females only (N = 379)* | | | | |
| Fractures in any of the three places or otherwise | | | | |
| Forward selection | 49.1% | 94.8% | 9.4 | 0.832 |
| Backstep selection | 50.0% | 95.2% | 10.4 | 0.861 |

Figure 16

Figure 17A: General model FSTEP

| | B | E.T. | Wald | gl | Sig. | Exp(B) | CI 95.0% EXP(B) Lower | Upper |
|---|---|---|---|---|---|---|---|---|
| rs2234693 | | | 10,07507 | 2 | 0,00649 | | | |
| rs2234693 CT vs CC | -0,80463 | 0,283769 | 8,040098 | 1 | 0,004575 | 0,447254 | 0,256454 | 0,780007 |
| rs2234693 TT vs CC | -0,8946 | 0,309055 | 8,378904 | 1 | 0,003796 | 0,408771 | 0,223055 | 0,749114 |
| rs412777 | | | 6,121831 | 2 | 0,046845 | | | |
| rs412777 AC vs AA | -0,56667 | 0,245175 | 5,342025 | 1 | 0,020817 | 0,567412 | 0,350918 | 0,917471 |
| rs412777 CC vs AA | -0,50917 | 0,31779 | 2,567106 | 1 | 0,109107 | 0,600995 | 0,32238 | 1,120402 |
| rs4680 | | | 7,141413 | 2 | 0,028136 | | | |
| rs4680 GA vs AA | -0,02072 | 0,274869 | 0,005683 | 1 | 0,93991 | 0,979493 | 0,571521 | 1,67869 |
| rs4680 GG vs AA | -0,68215 | 0,31071 | 4,820091 | 1 | 0,02813 | 0,505527 | 0,274959 | 0,929439 |
| rs12926089 | | | 8,24132 | 2 | 0,016234 | | | |
| rs12926089 CT vs CC | -0,39807 | 0,259037 | 2,361529 | 1 | 0,124436 | 0,671616 | 0,40423 | 1,11587 |
| rs12926089 TT vs CC | -0,92607 | 0,322598 | 8,240738 | 1 | 0,004096 | 0,396106 | 0,210482 | 0,745432 |
| rs523349 | | | 7,199293 | 2 | 0,027333 | | | |
| rs523349 GC vs CC | -0,88952 | 0,349856 | 6,464421 | 1 | 0,011006 | 0,410854 | 0,206962 | 0,815616 |
| rs523349 GG vs CC | -0,87599 | 0,349752 | 6,27309 | 1 | 0,012259 | 0,416448 | 0,209822 | 0,826552 |
| AGE | 0,128311 | 0,015821 | 65,77553 | 1 | 5,05E-16 | 1,136906 | 1,102194 | 1,172712 |
| Constant | -7,28214 | 1,128287 | 41,65606 | 1 | 1,09E-10 | 0,000688 | | |

Figure 17 B: General model BSTEP

| | B | E.T. | Wald | gl | Sig. | Exp(B) | CI 95.0% EXP(B) Lower | Upper |
|---|---|---|---|---|---|---|---|---|
| rs2234693 | | | 8,853427 | 2 | 0,011954 | | | |
| rs2234693 CT vs CC | -0,71453 | 0,296377 | 5,812263 | 1 | 0,015915 | 0,489424 | 0,273784 | 0,874908 |
| rs2234693 TT vs CC | -0,93356 | 0,324086 | 8,297713 | 1 | 0,00397 | 0,393154 | 0,208305 | 0,742036 |
| rs412777 | | | 4,654741 | 2 | 0,097552 | | | |
| rs412777 AC vs AA | -0,48857 | 0,252205 | 3,75267 | 1 | 0,052723 | 0,613505 | 0,374232 | 1,005763 |
| rs412777 CC vs AA | -0,51306 | 0,335862 | 2,333524 | 1 | 0,126615 | 0,598661 | 0,309952 | 1,156293 |
| rs4680 | | | 6,013958 | 2 | 0,049441 | | | |
| rs4680 GA vs AA | 0,000317 | 0,288087 | 1,21E-06 | 1 | 0,999121 | 1,000317 | 0,568745 | 1,759374 |
| rs4680 GG vs AA | -0,63165 | 0,322909 | 3,826399 | 1 | 0,050451 | 0,531714 | 0,282369 | 1,001243 |
| rs7702178 | | | 5,611995 | 2 | 0,060446 | | | |
| rs7702178 AG vs AA | 0,565835 | 0,249252 | 5,153484 | 1 | 0,0232 | 1,760917 | 1,080376 | 2,870138 |
| rs7702178 GG vs AA | 0,573392 | 0,595519 | 0,927071 | 1 | 0,335625 | 1,774276 | 0,552223 | 5,70069 |
| rs724449 | | | 8,833677 | 2 | 0,012072 | | | |
| rs724449 GA vs AA | -1,45435 | 0,520859 | 7,796463 | 1 | 0,005235 | 0,233552 | 0,084145 | 0,648246 |
| rs724449 GG vs AA | -0,82689 | 0,752888 | 1,206237 | 1 | 0,272079 | 0,437408 | 0,100006 | 1,913139 |
| rs12926089 | | | 8,305824 | 2 | 0,015719 | | | |
| rs12926089 CT vs CC | -0,38268 | 0,267842 | 2,04136 | 1 | 0,153073 | 0,68203 | 0,403474 | 1,152897 |
| rs12926089 TT vs CC | -0,95788 | 0,332612 | 8,293629 | 1 | 0,003978 | 0,383706 | 0,19993 | 0,736408 |
| rs592849 | | | 5,782026 | 2 | 0,05552 | | | |
| rs592849 GA vs AA | 0,449147 | 0,455293 | 0,973183 | 1 | 0,323888 | 1,566975 | 0,641972 | 3,824797 |
| rs592849 GG vs AA | 0,887576 | 0,448253 | 3,920707 | 1 | 0,047695 | 2,429234 | 1,009057 | 5,848212 |
| rs523349 | | | 6,383547 | 2 | 0,041099 | | | |
| rs523349 GC vs CC | -0,86912 | 0,360652 | 5,807452 | 1 | 0,015958 | 0,419319 | 0,206803 | 0,850222 |
| rs523349 GG vs CC | -0,84468 | 0,361827 | 5,449831 | 1 | 0,01957 | 0,429695 | 0,211433 | 0,873268 |
| rs1869872 | | | 11,44502 | 2 | 0,003271 | | | |
| rs1869872 CT vs CC | 1,460101 | 0,518937 | 7,916567 | 1 | 0,004898 | 4,306392 | 1,557378 | 11,90785 |
| rs1869872 TT vs CC | 0,29728 | 0,798421 | 0,138634 | 1 | 0,709643 | 1,346193 | 0,281508 | 6,437603 |
| AGE | 0,13263 | 0,016693 | 63,12792 | 1 | 1,94E-15 | 1,141827 | 1,105074 | 1,179803 |
| Constant | -8,4241 | 1,308285 | 41,46127 | 1 | 1,2E-10 | 0,00022 | | |

Figure 18A: Male Model FSTEP

| | B | E.T. | Wald | gl | Sig. | Exp(B) | CI 95.0% EXP(B) Lower | Upper |
|---|---|---|---|---|---|---|---|---|
| rs3736228 (CT+TT) vs CC | -1,12778 | 0,578424 | 3,801492 | 1 | 0,051207 | 0,323752 | 0,104197 | 1,00593 |
| AGE | 0,092886 | 0,028383 | 10,7098 | 1 | 0,001066 | 1,097336 | 1,037959 | 1,160111 |
| Constant | -7,57805 | 2,007503 | 14,24958 | 1 | 0,00016 | 0,000512 | | |

Figure 18B: Male Model BSTEP

| | B | E.T. | Wald | gl | Sig. | Exp(B) | CI 95.0% EXP(B) Lower | Upper |
|---|---|---|---|---|---|---|---|---|
| rs9550373 | | | 6,665952 | 2 | 0,035687 | | | |
| rs9550373 CT vs CC | 1,931065 | 0,753262 | 6,572059 | 1 | 0,010359 | 6,896852 | 1,575698 | 30,18762 |
| rs9550373 TT vs CC | 1,727807 | 0,794517 | 4,729165 | 1 | 0,029655 | 5,628297 | 1,185996 | 26,70981 |
| rs9340799 | | | 6,850364 | 2 | 0,032543 | | | |
| rs9340799 GA vs AA | 1,410322 | 0,561371 | 6,311557 | 1 | 0,011995 | 4,097275 | 1,3635 | 12,31218 |
| rs9340799 GG vs AA | 1,35935 | 0,740985 | 3,365456 | 1 | 0,066577 | 3,893663 | 0,911236 | 16,63742 |
| rs523349 | | | 7,344304 | 2 | 0,025422 | | | |
| rs523349 GC vs CC | 1,438125 | 0,794885 | 3,273289 | 1 | 0,070416 | 4,21279 | 0,887079 | 20,0068 |
| rs523349 GG vs CC | 0,093585 | 0,783837 | 0,014255 | 1 | 0,904964 | 1,098104 | 0,236287 | 5,103248 |
| rs4680 | | | 4,943789 | 2 | 0,084425 | | | |
| rs4680 GA vs AA | -0,37378 | 0,611555 | 0,373556 | 1 | 0,541073 | 0,68813 | 0,207546 | 2,281536 |
| rs4680 GG vs AA | -1,51588 | 0,722233 | 4,40528 | 1 | 0,035828 | 0,219615 | 0,053321 | 0,904542 |
| rs5918 TT vs (CT+CC) | -1,15551 | 0,618793 | 3,487007 | 1 | 0,061852 | 0,314898 | 0,093638 | 1,058981 |
| rs2073618 | | | 4,573249 | 2 | 0,101609 | | | |
| rs2073618 GC vs CC | 0,922581 | 0,576728 | 2,558979 | 1 | 0,109669 | 2,515775 | 0,812381 | 7,790826 |
| rs2073618 GG vs CC | 1,468448 | 0,707932 | 4,302634 | 1 | 0,038053 | 4,34249 | 1,084292 | 17,39127 |
| rs724449 | | | 6,452773 | 2 | 0,039701 | | | |
| rs724449 GA vs AA | -0,6841 | 0,54525 | 1,574137 | 1 | 0,209607 | 0,504546 | 0,173294 | 1,46899 |
| rs724449 GG vs AA | -2,52963 | 0,999844 | 6,401003 | 1 | 0,011406 | 0,079689 | 0,011229 | 0,565544 |
| rs3736228 (CT+TT) vs CC | -1,60716 | 0,70866 | 5,143302 | 1 | 0,023336 | 0,200456 | 0,049981 | 0,803955 |
| rs6152 GG vs (GA+AA) | 1,78517 | 0,855867 | 4,350581 | 1 | 0,036996 | 5,960595 | 1,113717 | 31,90101 |
| AGE | 0,129465 | 0,033721 | 14,73975 | 1 | 0,000123 | 1,138219 | 1,065423 | 1,215988 |
| Constante | -14,1576 | 3,061165 | 21,38965 | 1 | 3,75E-06 | 7,1E-07 | | |

Figure 19A: Female Model FSTEP

| | B | E.T. | Wald | gl | Sig. | Exp(B) | CI 95.0% EXP(B) Lower | Upper |
|---|---|---|---|---|---|---|---|---|
| rs412777 CC vs (AC+CC) | -0,60966 | 0,291709 | 4,367991 | 1 | 0,03662 | 0,543533 | 0,306847 | 0,962785 |
| rs592849 | | | 8,403727 | 2 | 0,014968 | | | |
| rs592849 GA vs AA | 0,830613 | 0,586847 | 2,003306 | 1 | 0,156957 | 2,294724 | 0,72645 | 7,248623 |
| rs592849 GG vs AA | 1,433162 | 0,577972 | 6,148599 | 1 | 0,013152 | 4,191931 | 1,35034 | 13,01323 |
| rs1805034 (CT+TT) vs CC | -0,70206 | 0,329886 | 4,529223 | 1 | 0,033321 | 0,495562 | 0,259596 | 0,946014 |
| rs523349 | | | 15,40484 | 2 | 0,000452 | | | |
| rs523349 GC vs CC | -1,78269 | 0,454386 | 15,39226 | 1 | 8,73E-05 | 0,168185 | 0,069026 | 0,40979 |
| rs523349 GG vs CC | -1,32076 | 0,442891 | 8,893178 | 1 | 0,002862 | 0,266931 | 0,112049 | 0,6359 |
| rs6256 CC vs (AC+AA) | -0,57697 | 0,289133 | 3,982116 | 1 | 0,045986 | 0,561596 | 0,318649 | 0,989771 |
| rs1800012 (GT+TT) vs GG | -0,66756 | 0,295537 | 5,10219 | 1 | 0,023896 | 0,512959 | 0,287423 | 0,91547 |
| AGE | 0,1807 | 0,022071 | 67,03021 | 1 | 2,67E-16 | 1,198056 | 1,147335 | 1,251019 |
| Constante | -11,5428 | 1,555843 | 55,0419 | 1 | 1,18E-13 | 9,71E-06 | | |

Figure 19B: Female Model BSTEP

| | B Inferior | E.T. Superior | Wald Inferior | gl Superior | Sig. Inferior | Exp(B) Superior | CI 95.0% EXP(B) Inferior | Superior |
|---|---|---|---|---|---|---|---|---|
| rs2234693 | | | 6,454 | 2 | 0,039676 | | | |
| rs2234693 CT vs CC | -0,89724 | 0,394832 | 5,164142 | 1 | 0,023058 | 0,407691 | 0,18804 | 0,88392 |
| rs2234693 TT vs CC | -1,00197 | 0,424686 | 5,566335 | 1 | 0,018309 | 0,367157 | 0,15972 | 0,844006 |
| rs12926089 | | | 7,022861 | 2 | 0,029854 | | | |
| rs12926089 CT vs CC | -0,48155 | 0,333536 | 2,084496 | 1 | 0,148801 | 0,617824 | 0,321335 | 1,187875 |
| rs12926089 TT vs CC | -1,11531 | 0,422393 | 6,971949 | 1 | 0,00828 | 0,327815 | 0,143248 | 0,750189 |
| rs592849 | | | 9,981753 | 2 | 0,0068 | | | |
| rs592849 GA vs AA | 0,787225 | 0,617358 | 1,626011 | 1 | 0,202256 | 2,19729 | 0,655226 | 7,368576 |
| rs592849 GG vs AA | 1,543907 | 0,607721 | 6,454063 | 1 | 0,01107 | 4,682851 | 1,423039 | 15,41004 |
| rs9550373 | | | 5,690146 | 2 | 0,05813 | | | |
| rs9550373 CT vs CC | -0,81263 | 0,363483 | 4,998296 | 1 | 0,025372 | 0,443688 | 0,21761 | 0,904638 |
| rs9550373 TT vs CC | -0,8344 | 0,422464 | 3,900961 | 1 | 0,048258 | 0,434134 | 0,18968 | 0,993632 |
| rs1805034 (CT+TT) vs CC | -0,58472 | 0,348975 | 2,807409 | 1 | 0,09383 | 0,557262 | 0,281198 | 1,104353 |
| rs523349 | | | 14,99155 | 2 | 0,000555 | | | |
| rs523349 GC vs CC | -1,89316 | 0,491359 | 14,84487 | 1 | 0,000117 | 0,150595 | 0,057486 | 0,394509 |
| rs523349 GG vs CC | -1,57507 | 0,481179 | 10,71494 | 1 | 0,001063 | 0,206992 | 0,080607 | 0,531537 |
| rs2230949 (CT+TT) vs CC | -0,74416 | 0,428177 | 3,020531 | 1 | 0,082217 | 0,475134 | 0,205282 | 1,099718 |
| rs6256 CC vs (AC+AA) | -0,52929 | 0,30418 | 3,027766 | 1 | 0,081851 | 0,589024 | 0,3245 | 1,069182 |
| rs1800012 (GT+TT) vs GG | -0,62752 | 0,310724 | 4,078579 | 1 | 0,04343 | 0,533913 | 0,290391 | 0,981656 |
| rs1061622 (GT+TT) vs GG | -0,52896 | 0,311865 | 2,876848 | 1 | 0,089862 | 0,589216 | 0,319753 | 1,085761 |
| rs7702178 (GG+AG) vs AA | 0,628618 | 0,305096 | 4,245234 | 1 | 0,039361 | 1,875018 | 1,031116 | 3,4096 |
| AGE | 0,184704 | 0,023535 | 61,59392 | 1 | 4,22E-15 | 1,202862 | 1,148638 | 1,259646 |
| Constant | -9,89249 | 1,671511 | 35,02618 | 1 | 3,25E-09 | 5,06E-05 | | |

DIAGNOSTIC METHOD

RELATED APPLICATIONS

This application is a national stage filing under 35 U.S.C. §371 of PCT International application PCT/IB2007/002363 designating the United States of America, and filed Jul. 12, 2007, the entire contents of which are hereby incorporated herein by reference. This application claims the benefit of priority under 35 U.S.C. §119 from Application No. GB 0613843.2, filed in the United Kingdom on Jul. 12, 2006, and from Application No. GB 0623502.2, filed in the United Kingdom on Nov. 24, 2006, the entire contents of each of which are hereby incorporated herein by reference.

FIELD OF THE INVENTION

The invention relates to methods and products, in particular microarrays, for in vitro genotyping of osteoporosis associated genetic variations. The invention further relates to methods for predicting and treating low bone mineral density (BMD) and fractures in osteoporosis and to products for use therein.

BACKGROUND OF THE INVENTION

Osteoporosis, or porous bone, is a disease characterized by low bone mass and structural deterioration of bone tissue, leading to bone fragility and an increased risk of fractures of the hip, spine (vertebras), and wrist. Wrongly often thought of as an "old woman's disease", osteoporosis affects not only one in three postmenopausal women, but also one in five men over the age of 50, younger women and even children. Osteoporosis is known as the "silent epidemic" because there are often no symptoms until a fracture occurs. Once a fracture has occurred, the risk of a future fracture is at least doubled within one year.

People with broken bones suffer severe pain and disability, resulting in a loss of quality of life and independence. There is also an increased risk of death—24% of women and 33% of men die within one year after a hip fracture. Yet the sad reality in Europe is that osteoporosis is usually not diagnosed in time. Despite the availability of approved diagnostic and therapeutic options, people continue to suffer fractures, many of which, could have been prevented. However, this disease could be prevented and treated if an accurate method could properly prognose low Bone Mineral Density and fractures.

As Europe's population ages and becomes more sedentary, the number of people affected by osteoporosis will increase significantly—hip fractures alone are expected to double in the next 50 years. Unless osteoporosis prevention and treatment becomes a priority for government and health care providers, this growing number of osteoporotic fractures will have a serious impact on society, not just in terms of people's quality of life, but also in regard to increased expenditure for health care, rehabilitation and nursing care.

Hip fractures are a serious result of osteoporosis. These fractures almost invariably result in chronic pain, reduced mobility, disability, and loss of independence. Hip fractures also result in mortality rates of up to 20-24% in the first year after a hip fracture. Various studies have shown that loss of function and independence among survivors is profound, with ca. 40% unable to walk independently and ca. 60% requiring assistance a year later. Because of these losses, around a third of the patients are totally dependent or in a nursing home in the year following a hip fracture. The number and cost of hip fractures are commonly used to measure the burden of osteoporosis because, unlike other osteoporotic fractures, statistics for hip fracture are usually available through hospital records. Vertebral fractures and wrist fractures often go unrecorded and, in the case of vertebral fractures, often remain undiagnosed.

People with osteoporosis suffer from a reduction in their bone mass and bone quality—put simply, their bones become fragile, leading to an increased risk of fractures. Bone density loss is without noticeable symptoms. The most reliable way to determine loss of bone mass is to have a bone mineral density (BMD) test. DXA scans (Dual Energy X-Ray Absorptiometry) are the most accurate and most commonly used method of BMD measurement and are usually used to measure spine and hip bone densities. DXA scans are vital in order to properly diagnose and monitor osteoporosis. Yet access to bone mineral density measurement is sub-optimal in many European countries. Reasons include limited availability of densitometers, restrictions in personnel permitted to perform scans, low awareness of the usefulness of BMD testing, limited or non-existent reimbursement. Many of the DXA scanners are not available to the public health care system, or regional disparities mean that some parts of a country are under-serviced.

Therefore, there remains in the art, a need for reliable means of predicting fractures and/or low bone mineral density. Early diagnosis or prognosis could affect therapeutic decisions.

A comprehensive osteoporosis treatment program includes a focus on proper nutrition, exercise, and safety issues to prevent falls that may result in fractures. In addition, there are therapeutic medications to slow or stop bone loss, increase bone density, and reduce fracture risk. Currently treatments for Osteoporosis include alendronate, raloxifene, risedronate, and ibandronate and they are approved by the U.S. Food and Drug Administration (FDA) for preventing and treating postmenopausal osteoporosis. Teriparatide is approved for treating the disease in postmenopausal women and men at high risk for fracture. Estrogen/hormone therapy (ET/HT) is approved for preventing postmenopausal osteoporosis, and calcitonin is approved for treatment. In addition, alendronate is approved for treating osteoporosis in men, and both alendronate and risedronate are approved for use by men and women with glucocorticoid-induced osteoporosis.

Studies have identified a number of genes in which one or more genetic variations result in a higher or lower risk of contracting osteoporosis, a better or worse response to drugs and furthermore, a better or worse prognosis of the disease and the risk for suffering fractures.

However, there remains a need for a reliable means of characterising such genetic variations which can be used for clinical purposes.

DNA chips are often used to determine alleles at generic loci.

In 2001, the Consortium for the Human Genome Project and the private company Celera presented the first complete example of the human genome with 30,000 genes. From this moment on, the possibility of studying the complete genome or large scale (high-throughput) studies began. So-called "DNA-chips", also named "micro-arrays", "DNA-arrays" or "DNA bio-chips" are apparatus that functional genomics can use for large scale studies. Functional genomics studies changes in the expression of genes due to environmental factors and to genetic characteristics of an individual. Gene sequences present small interindividual variations at one unique nucleotide called an SNP ("single nucleotide polymorphism"), which in a small percentage are involved in changes in the expression and/or function of genes that cause certain pathologies. The majority of studies which apply DNA-chips study gene expression, although chips are also used in the detection of SNPs.

The first DNA-chip was the "Southern blot" where labelled nucleic acid molecules were used to examine nucleic acid molecules attached to a solid support. The support was typically a nylon membrane.

Two breakthroughs marked the definitive beginning of DNA-chip. The use of a solid non-porous support, such as glass, enabled miniaturisation of arrays thereby allowing a large number of individual probe features to be incorporated onto the surface of the support at a density of >1,000 probes per $cm^2$. The adaptation of semiconductor photolithographic techniques enabled the production of DNA-chips containing more than 400,000 different oligonucleotides in a region of approximately 20 $\mu m^2$, so-called high density DNA-chips.

In general, a DNA-chip comprises a solid support, which contains hundreds of fragments of sequences of different genes represented in the form of DNA, cDNA or fixed oligonucleotides, attached to the solid surface in fixed positions. The supports are generally glass slides for the microscope, nylon membranes or silicon "chips". It is important that the nucleotide sequences or probes are attached to the support in fixed positions as the robotized localisation of each probe determines the gene whose expression is being measured. DNA-chips can be classified as:

high density DNA-chips: the oligonucleotides found on the surface of the support, e.g. glass slides, have been synthesized "in situ", by a method called photolithography.

low density DNA-chips: the oligonucleotides, cDNA or PCR amplification fragments are deposited in the form of nanodrops on the surface of the support, e.g. glass, by means of a robot that prints those DNA sequences on the support. There are very few examples of low density DNA-chips which exist: a DNA-chip to detect 5 mutations in the tyrosinase gene; a DNA-chip to detect mutations in p53 and k-ras; a DNA-chip to detect 12 mutations which cause hypertrophic cardiomypathy; a DNA-chip for genotyping of *Escherichia coli* strains; or DNA-chips to detect pathogens such as *Cryptosporidium parvum* or rotavirus.

For genetic expression studies, probes deposited on the solid surface, e.g. glass, are hybridized to cDNAs synthesized from mRNAs extracted from a given sample. In general the cDNA has been labelled with a fluorophore. The larger the number of cDNA molecules joined to their complementary sequence in the DNA-chip, the greater the intensity of the fluorescent signal detected, typically measured with a laser. This measure is therefore a reflection of the number of mRNA molecules in the analyzed sample and consequently, a reflection of the level of expression of each gene represented in the DNA-chip.

Gene expression DNA-chips typically also contain probes for detection of expression of control genes, often referred to as "house-keeping genes", which allow experimental results to be standardized and multiple experiments to be compared in a quantitative manner. With the DNA-chip, the levels of expression of hundreds or thousands of genes in one cell can be determined in one single experiment. cDNA of a test sample and that of a control sample can be labelled with two different fluorophores so that the same DNA-chip can be used to study differences in gene expression.

DNA-chips for detection of genetic polymorphisms, changes or mutations (in general, genetic variations) in the DNA sequence, comprise a solid surface, typically glass, on which a high number of genetic sequences are deposited (the probes), complementary to the genetic variations to be studied. Using standard robotic printers to apply probes to the array a high density of individual probe features can be obtained, for example probe densities of 600 features per $cm^2$ or more can be typically achieved. The positioning of probes on an array is precisely controlled by the printing device (robot, inkjet printer, photolithographic mask etc) and probes are aligned in a grid. The organisation of probes on the array facilitates the subsequent identification of specific probe-target interactions. Additionally it is common, but not necessary to divide the array features into smaller sectors, also grid-shaped, that are subsequently referred to as sub-arrays. Sub-arrays typically comprise 32 individual probe features although lower (e.g. 16) or higher (e.g. 64 or more) features can comprise each subarray.

One strategy used to detect genetic variations involves hybridization to sequences which specifically recognize the normal and the mutant allele in a fragment of DNA derived from a test sample. Typically, the fragment has been amplified, e.g. by using the polymerase chain reaction (PCR), and labelled e.g. with a fluorescent molecule. A laser can be used to detect bound labelled fragments on the chip and thus an individual who is homozygous for the normal allele can be specifically distinguished from heterozygous individuals (in the case of autosomal dominant conditions then these individuals are referred to as carriers) or those who are homozygous for the mutant allele.

Another strategy to detect genetic variations comprises carrying out an amplification reaction or extension reaction on the DNA-chip itself.

For differential hybridisation based methods there are a number of methods for analysing hybridization data for genotyping:

Increase in hybridization level: The hybridization level of complementary probes to the normal and mutant alleles are compared.

Decrease in hybridization level: Differences in the sequence between a control sample and a test sample can be identified by a fall in the hybridization level of the totally complementary oligonucleotides with a reference sequence. A complete loss is produced in mutant homozygous individuals while there is only 50% loss in heterozygotes. In DNA-chips for examining all the bases of a sequence of "n" nucleotides ("oligonucleotide") of length in both strands, a minimum of "2n" oligonucleotides that overlap with the previous oligonucleotide in all the sequence except in the nucleotide are necessary. Typically the size of the oligonucleotides is about 25 nucleotides. The increased number of oligonucleotides used to reconstruct the sequence reduces errors derived from fluctuation of the hybridization level. However, the exact change in sequence cannot be identified with this method; sequencing is later necessary in order to identify the mutation.

Where amplification or extension is carried out on the DNA-chip itself, three methods are presented by way of example:

In the Minisequencing strategy, a mutation specific primer is fixed on the slide and after an extension reaction with fluorescent dideoxynucleotides, the image of the DNA-chip is captured with a scanner.

In the Primer extension strategy, two oligonucleotides are designed for detection of the wild type and mutant sequences respectively. The extension reaction is subsequently carried out with one fluorescently labelled nucleotide and the remaining nucleotides unlabelled. In either case the starting material can be either an RNA sample or a DNA product amplified by PCR.

In the Tag arrays strategy, an extension reaction is carried out in solution with specific primers, which carry a determined 5' sequence or "tag". The use of DNA-chips with oligonucleotides complementary to these sequences or "tags" allows the capture of the resultant products of the extension. Examples of this include the high density DNA-chip "Flex-flex" (Affymetrix).

For genetic diagnosis, simplicity must be taken into account. The need for amplification and purification reactions presents disadvantages for the on-chip extension/amplification methods compared to the differential hybridization based methods.

Typically, DNA-chip analysis is carried out using differential hybridization techniques. However, differential hybridization does not produce as high specificity or sensitivity as methods associated with amplification on glass slides. For this reason the development of mathematical algorithms, which increase specificity and sensitivity of the hybridization methodology, are needed (Cutler D J, Zwick M E, Carrasquillo M N, Yohn C T, Tobi K P, Kashuk C, Mathews D J, Shah N, Eichler E E, Warrington J A, Chakravarti A. Genome Research; 11:1913-1925 (2001).

Thus, despite advances in technology, the problems of existing methods is simultaneously analysing a large number of genetic variations in a sensitive, specific and reproducible way, has prevented the application of DNA-chips for routine use in clinical diagnosis

SUMMARY OF THE INVENTION

The inventors have identified new mean for determining osteoporosis phenotypes and osteoporosis quantitative traits based on combinations of informative SNP variables and clinical variables.

Accordingly in one aspect the invention provides a method of prognosing an osteoporosis phenotype in a subject, which comprises:
(I) obtaining outcomes for one or more single nucleotide polymorphism variables and one or more clinical variables for the subject; and
(II) using the outcomes obtained in (I) to prognose the phenotype;
wherein:
(a) the osteoporosis phenotype is a presence of one or more non-traumatic fractures in the wrist, hip or spine (WSHfractures) and the variables for which outcomes are obtained in step (I) comprise the general BSTEP model variables in FIG. 9; and/or
(b) the osteoporosis phenotype is a presence of one or more non-traumatic fractures in the wrist, hip or spine (WSHfractures) and the variables for which outcomes are obtained in step (I) comprise the general FSTEP model variables in FIG. 9; and/or
(c) the osteoporosis phenotype is a presence of one or more non-traumatic fractures in the wrist, hip or spine (WSHfractures) and the variables for which outcomes are obtained in step (I) comprise the male BSTEP model variables in FIG. 9; and/or
(d) the osteoporosis phenotype is a presence of one or more non-traumatic fractures in the wrist, hip or spine (WSHfractures) and the variables for which outcomes are obtained in step (I) comprise the male FSTEP model variables in FIG. 9; and/or
(e) the osteoporosis phenotype is a presence of one or more non-traumatic fractures in the wrist, hip or spine (WSHfractures) and the variables for which outcomes are obtained in step (I) comprise the female BSTEP model variables in FIG. 9; and/or
(f) the osteoporosis phenotype is a presence of one or more non-traumatic fractures in the wrist, hip or spine (WSHfractures) and the variables for which outcomes are obtained in step (I) comprise the female FSTEP model variables in FIG. 9; and/or
(g) the osteoporosis phenotype is presence of one or more non-traumatic vertebral factures and the variables for which outcomes are obtained in step (I) comprise the male vertebral factures variables or the female vertebral factures variables in Table 5;
and wherein
(i) an outcome for an SNP variable is the identity of the nucleotide in the genomic DNA of the subject at the position of the single nucleotide polymorphism;
(ii) an outcome for the clinical variable AGE is age of the subject in years;
(iii) an outcome for the clinical variable MENOPAUSE AGE is the age in years of the onset of menopause in a female subject;
(iv) an outcome for the clinical variable MENARCHE AGE is the age in years of the onset of menarche in a female subject;
(v) an outcome for the clinical variable BMI is the body mass index of the subject.

The invention additionally provides a method of estimating an osteoporosis quantitative trait in a subject, which comprises:
(I) obtaining outcomes for one or more single nucleotide polymorphism variables and one or more clinical variables for the subject; and
(II) using the outcomes obtained in (I) to estimate the trait;
wherein:
(a) the quantitative trait is lumbar spine bone mineral density (LSBMD) and the variables for which outcomes are obtained in step (I) comprise the male or female LSBMD variables in Table 5; and/or
(b) the quantitative trait is femoral neck bone mineral density (FNBMD) and the variables for which outcomes are obtained in step (I) comprise the male or female FNBMD variables in Table 5; and wherein
(i) an outcome for an SNP variable is the identity of the nucleotide in the genomic DNA of the subject at the position of the single nucleotide polymorphism;
(ii) an outcome for the clinical variable AGE is age of the subject in years;
(iii) an outcome for the clinical variable MENOPAUSE AGE is the age in years of the onset of menopause in a female subject;
(iv) an outcome for the clinical variable MENARCHE AGE is the age in years of the onset of menarche in a female subject;
(v) an outcome for the clinical variable BMI is the body mass index of the subject.

The invention also relates to a method of deriving a probability function for use in prognosing an osteoporosis phenotype in a subject and a computational method of deriving a probability function for use in prognosing an osteoporosis phenotype in a subject as set out in the present claims.

Also provided is a method of deriving a quantitative function for use in predicting an osteoporosis quantitative trait in a subject and a computational method of deriving a probability function for use in prognosing an osteoporosis quantitative trait in a subject as described in the present claims.

The invention further provides a method of selecting a suitable treatment for treating osteoporosis in a subject and a method of treating osteoporosis in a subject as described in the present claims.

The inventors have also developed a method for accurate genotyping of multiple genetic variations, using microarray technology. Accordingly the invention also provides an in vitro method for genotyping osteoporosis associated genetic variations in an individual, the method comprising:

(a) providing a sample containing nucleic acid which comprises the genetic variations to be genotyped (the target DNA);
(b) providing, for each genetic variation to be genotyped, at least 2 oligonucleotide probe pairs, wherein:
(i) one pair consists of probes 1 and 2, and the other pair consists of probes 3 and 4;
(ii) one probe in each pair is capable of hybridising to genetic variation A and the other probe in each pair is capable of hybridising to genetic variation B;
(iii) each probe is provided in replicates; and
(iv) the probe replicates are deposited at positions on a solid support according to a known uniform distribution;
(c) contacting the target DNA with the probes under conditions which allow hybridisation to occur, thereby forming nucleic acid-probe hybridisation complexes, wherein each complex is detectably labelled;
(d) determining the intensity of detectable label at each probe replica position, thereby obtaining a raw intensity value;
(e) optionally amending the raw intensity value to take account of background noise, thereby obtaining a clean intensity value for each replica; and
(e) applying a suitable algorithm to the intensity data from (d) or (e), thereby determining the genotype with respect to each genetic variation, wherein application of the algorithm comprises calculating an average intensity value from the intensity values for each of the replicas of each probe and wherein the algorithm uses three linear functions that characterise each of the three possible genotypes AA, AB or BB for the genetic variation.

Also provided is:
- a computational method for obtaining a genotype from DNA-chip hybridisation intensity data;
- a method of deriving linear functions for use in the present genotyping methods;
- a computational method of deriving linear functions for use in the present genotyping methods;
- a method of diagnosing osteoporosis or susceptibility to osteoporosis in an individual comprising genotyping an individual with respect to one or more genetic variations;
- a method of selecting a treatment for an individual having osteoporosis;
- a method of treating an individual having osteoporosis;
- a method of identifying genetic variations predictive of a particular osteoporosis phenotype;
- a method of predicting the likely development of the osteoporosis phenotype of an individual by determining the genotype of the individual with respect to one more genetic variations which have been identified by a method of the invention;
- a computer system comprising a processor and means for controlling the processor to carry out a computational method of the invention;
- a computer program comprising computer program code which when run on a computer or computer network causes the computer or computer network to carry out the computational method of the invention;
- a microarray comprising oligonucleotide probes suitable for determining the allele in a sample nucleic acid at SNPs selected from: the general BSTEP model SNPs in FIG. 9; and/or the general FSTEP model SNPs in FIG. 9; and/or the male BSTEP model SNPs in FIG. 9; and/or the male FSTEP model SNPs in FIG. 9; and/or the female BSTEP model SNPs in FIG. 9; and/or the female FSTEP model SNPs in FIG. 9;
- an oligonucleotide probe, probe pair, or 4-probe set listed in Table 2A, 2B or 2C (FIG. 2);
- an oligonucleotide primer or primer pair listed in Table 3A, 3B or 3C (FIG. 3);
- a PCR amplification kit comprising at least one pair of primers according to the invention;
- a diagnostic kit for detection of osteoporosis associated genetic variations; and
- a kit for prognosing an osteoporosis phenotype in a subject or estimating an osteoporosis quantitative trait in a subject;

as set out in the present claims.

BRIEF DESCRIPTION OF THE SEQUENCES

SEQ ID NOS: 1-220 and 674-692 are PCR primers suitable for amplifying target DNA regions comprising osteoporosis associated genetic variations listed in Tables 1A/1B, as listed in Tables 3A/B/C.

SEQ ID NOS: 221-668 and 693-829 are probes suitable for detection of the osteoporosis associated genetic variations in Table 1A & 1B, as listed in Tables 2A/B/C.

SEQ ID NO: 669 is an external control nucleic acid.

SEQ ID NOS: 670 & 571 are probes suitable for detection of the external control nucleic acid of SEQ ID NO: 669.

SEQ ID NO: 672 is a forward TAG sequence.

SEQ ID NO: 673 is a reverse TAG sequence.

TAG 672 is added to each forward primer and TAG 673 is added to each reverse primer in the Examples.

BRIEF DESCRIPTION OF THE FIGURES

FIG. 1

Figure 10A:
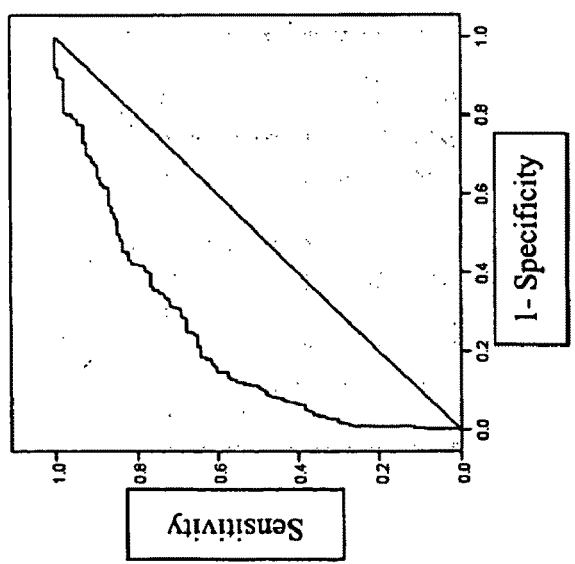

(A) Table 1A lists genetic variations (SNPs) associated with osteoporosis which may be analysed as described herein. The sequences of all the genes mentioned in Table 1A are known and recognized on the following websites: GeneBank (NCBI), GeneCard (Weizmann Institute of Sciences) and Snpper.chip.org (Innate Immunity PGA).

(B) Table 1B also shows the same SNPs as in Table 1A. RefSNP codes (rs#) for each SNP are taken from the Single Nucleotide Polymorphism Database (dbSNP) curated by the National Center for Biotechnology Information (NCBI) (available on the World Wide Web at www.ncbi.nlm.nih.gov/entrez/query.fcgi?CMD=search&DB=snp, as at 6 Jul. 2007).

FIG. 2:

(A) Table 2A lists oligonucleotide probes for discriminating between alleles at the SNPs listed in Table 1A/1B. The table lists two probe pairs for each SNP (a 4-probe set).

(B) Table 2B lists optimised probes for discriminating between alleles at some of the SNPs listed in Table 1A/1B.

(C) Table 2C lists oligonucleotide probes for discriminating between alleles at the SNPs listed in Table 1N1B. The table lists two probe pairs for each SNP (a 4-probe set). These probes are the same as the probes in Table 2A but include, for the relevant SNPs, the optimised probes of Table 2B.

FIG. 3

(A) Table 3A lists oligonucleotide primers for PCR amplification of nucleic acid regions containing the SNPs listed in Table 1A/1B.

(B) Table 3B lists optimised oligonucleotide primers for PCR amplification of nucleic acid regions containing some of the SNPs listed in Table 1N1B.

(C) Table 3C oligonucleotide primers for PCR amplification of nucleic acid regions containing the SNPs listed in Table 1A/1B. These primers are the same as the primers in Table 3A but include, for the relevant SNPs, the optimised primers of Table 3B.

FIG. 4

Table 4: Clinical characteristics of the 1029 individuals included in the present study (Examples 2 and 3).

FIG. 5

Table 5: Variables included in the probability functions and quantitative functions established in Example 2.

The SNP Nos given in Table 5 (Table 5, fourth column) are not consistent with the SNP Nos given in Table 1B. Where SNP Nos are used herein these refer to the SNP Nos in Table 1B (FIG. 1B).

FIG. 6.1

Probability function fractures in males (for predicting fracture risk in males).

Probability function is presented as box whisker plots in male individuals non suffering fractures (0) and male individuals suffering fractures (1) included in the study in Example 2. Boxes represent the interquartile range and whiskers are lines that extend from the box to the highest and lowest values. A line across the box indicates the median. Outliers and extreme values are represented as small circles.

FIG. 6.2

Probability function vertebral fractures in males (for predicting vertebral fracture risk in males).

Probability function is presented as box whisker plots in male individuals non suffering vertebral fractures (0) and male individuals suffering vertebral fractures (1) included in the study in Example 2. Boxes represent the interquartile range and whiskers are lines that extend from the box to the highest and lowest values. A line across the box indicates the median. Outliers and extreme values are represented as small circles.

FIG. 7.1

Probability function fractures in females (for predicting fracture risk in females).

Probability function is presented as box whisker plots in female individuals non suffering fractures (0) and female individuals suffering fractures (1) included in the study in Example 2. Boxes represent the interquartile range and whiskers are lines that extend from the box to the highest and lowest values. A line across the box indicates the median. Outliers and extreme values are represented as small circles.

FIG. 7.2

Probability function vertebral fractures in females (for predicting vertebral fracture risk in females). Probability function is presented as box whisker plots in female individuals non suffering vertebral fractures (0) and female individuals suffering vertebral fractures (1) included in the study in Example 2. Boxes represent the interquartile range and whiskers are lines that extend from the box to the highest and lowest values. A line across the box indicates the median. Outliers and extreme values are represented as small circles.

FIG. 8

R2 Values for quantitative functions in LSBMD and FNBMD for both genders (Example 2).

FIG. 9

Lists the variables included in each of the predictive models (probability functions) established in Example 3.

FIG. 10

(A) ROC (receiver operating characteristic) curve obtained for the General FSTEP model that allows the estimation of its discriminatory power. The ROC curve has been calculated in order to maximize the specificity, thus reducing at the same time the "false" positive rate. A specificity of 95.1% with a sensitivity of 37.7% is the cut-off for this model regarding the fractures phenotype. This model shows a likelihood ratio (LR) value of 7.7.

(B) Probability function for predicting Example 3 fractures phenotype according to the General FSTEP model Probability function is presented as box whisker plots in individuals not suffering fractures (0) and individuals suffering fractures (1) as defined in the study in Example 3. Boxes represent the interquartile range and whiskers are lines that extend from the box to the highest and lowest values. A line across the box indicates the median. Outliers and extreme values are represented as small circles.

FIG. 11

(A) ROC (receiver operating characteristic) curve obtained for the General BSTEP model that allows the estimation of its discriminatory power. The ROC curve has been calculated in order to maximize the specificity, thus reducing at the same time the "false" positive rate. A specificity of 95.1% with a sensitivity of 38.4% is the cut-off for this model regarding the fractures phenotype. This model shows a likelihood ratio (LR) value of 7.8.

(B) Probability function for predicting Example 3 fractures phenotype according to the General BSTEP model Probability function is presented as box whisker plots in individuals not suffering fractures (0) and individuals suffering fractures (1) as defined in the study in Example 3. Boxes represent the interquartile range and whiskers are lines that extend from the box to the highest and lowest values. A line across the box indicates the median. Outliers and extreme values are represented as small circles.

FIG. 12

(A) ROC (receiver operating characteristic) curve obtained for the male FSTEP model that allows the estimation of its discriminatory power. The ROC curve has been calculated in order to maximize the specificity, thus reducing at the same time the "false" positive rate. A specificity of 94.9% with a sensitivity of 27.8% is the cut-off for this model regarding the fractures phenotype. This model shows a likelihood ratio (LR) value of 5.5.

(B) Probability function for predicting Example 3 fractures phenotype according to the male FSTEP model Probability function is presented as box whisker plots in male individuals not suffering fractures (0) and male individuals suffering fractures (1) as defined in the study in Example 3. Boxes represent the interquartile range and whiskers are lines that extend from the box to the highest and lowest values. A line across the box indicates the median. Outliers and extreme values are represented as small circles.

FIG. 13

(A) ROC (receiver operating characteristic) curve obtained for the male BSTEP model that allows the estimation of its discriminatory power. The ROC curve has been calculated in order to maximize the specificity, thus reducing at the same time the "false" positive rate. A specificity of 94.9% with a sensitivity of 44.4% is the cut-off for this model regarding the fractures phenotype. This model shows a likelihood ratio (LR) value of 8.7.

(B) Probability function for predicting Example 3 fractures phenotype according to the male BSTEP model Probability function is presented as box whisker plots in male individuals not suffering fractures (0) and male individuals suffering fractures (1) as defined in the study in Example 3. Boxes represent the interquartile range and whiskers are lines that extend from the box to the highest and lowest values. A line across the box indicates the median. Outliers and extreme values are represented as small circles.

FIG. 14

(A) ROC (receiver operating characteristic) curve obtained for the female FSTEP model that allows the estimation of its discriminatory power. The ROC curve has been calculated in order to maximize the specificity, thus reducing at the same time the "false" positive rate. A specificity of 94.8% with a sensitivity of 49.1% is the cut-off for this model regarding the fractures phenotype. This model shows a likelihood ratio (LR) value of 9.4.

(B) Probability function for predicting Example 3 fractures phenotype according to the female FSTEP model Probability function is presented as box whisker plots in female individuals not suffering fractures (0) and female individuals suffering fractures (1) as defined in the study in Example 3. Boxes represent the interquartile range and whiskers are lines that extend from the box to the highest and lowest values. A line across the box indicates the median. Outliers and extreme values are represented as small circles.

FIG. 15

(A) ROC (receiver operating characteristic) curve obtained for the female BSTEP model that allows the estimation of its discriminatory power. The ROC curve has been calculated in order to maximize the specificity, thus, reducing at the same time the "false" positive rate. A specificity of 95.2% with a sensitivity of 50% is the cut-off for this model regarding the fractures phenotype. This model shows a likelihood ratio (LR) value of 10.4.

(B) Probability function for predicting Example 3 fractures phenotype according to the female BSTEP model Probability function is presented as box whisker plots in female individuals not suffering fractures (0) and female individuals suffering fractures (1) as defined in the study in Example 3. Boxes represent the interquartile range and whiskers are lines that extend from the box to the highest and lowest values. A line across the box indicates the median. Outliers and extreme values are represented as small circles.

FIG. 16

Figure 11A:
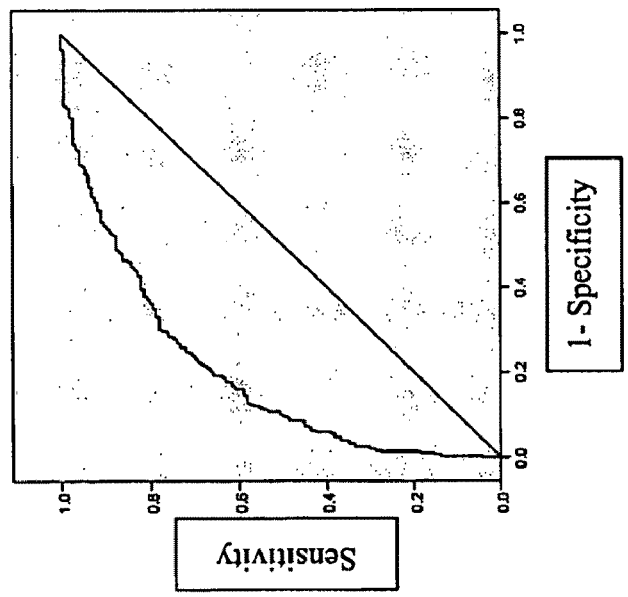
Figure 11B:
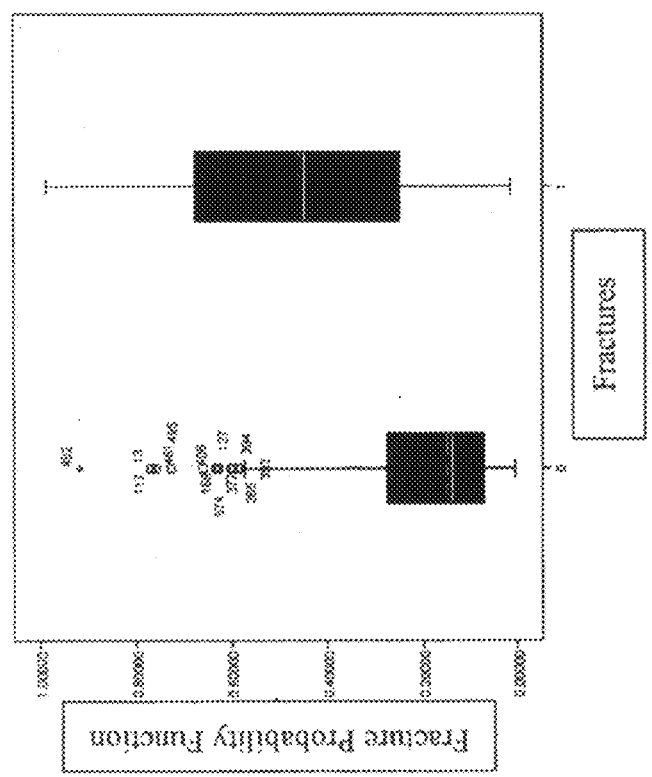
Figure 12A:
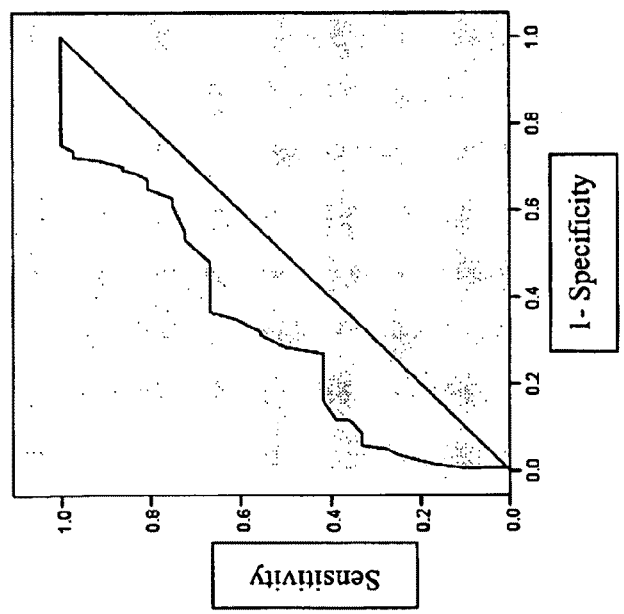
Figure 12B:
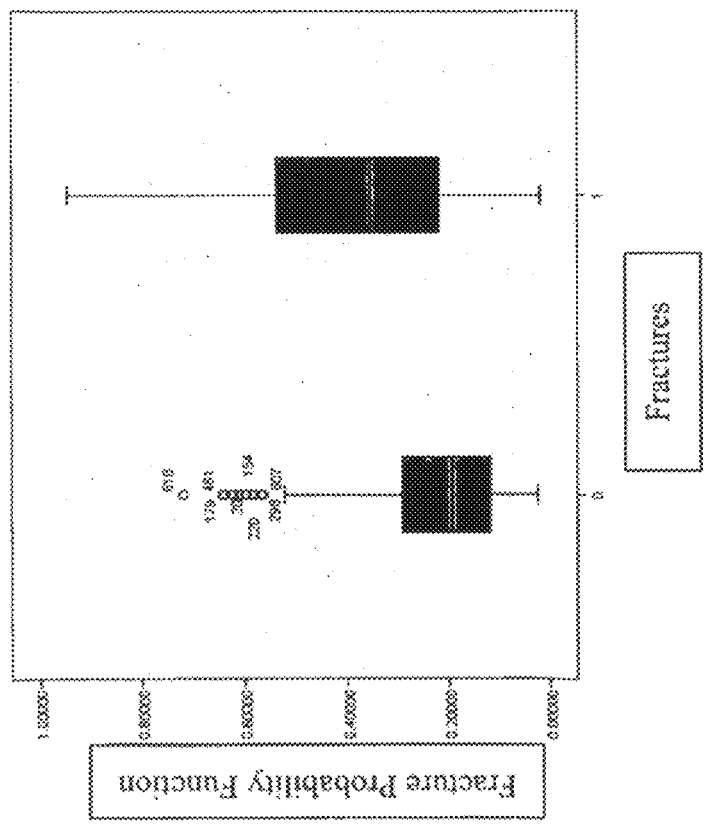
Figure 13A:
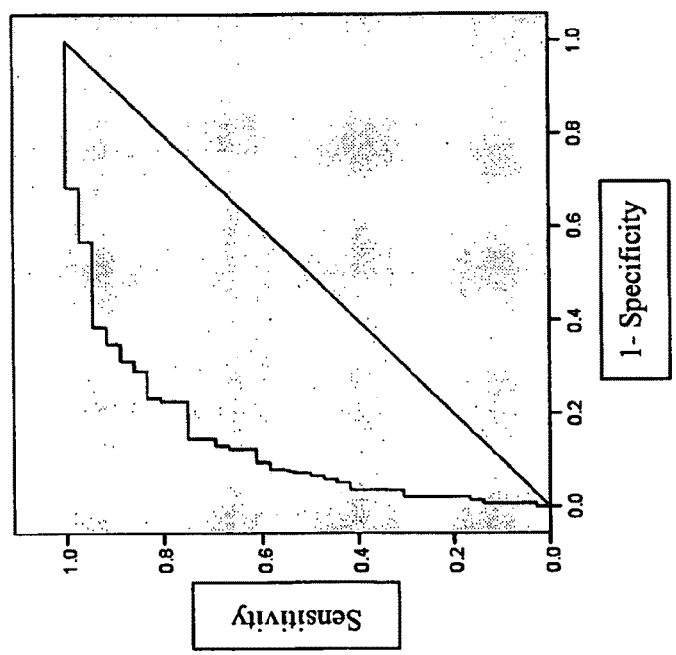
Figure 13B:
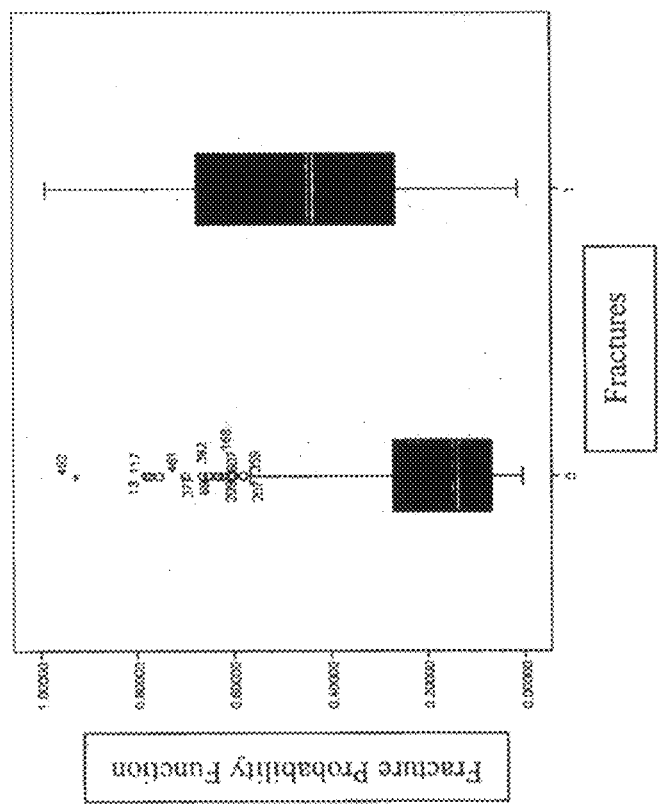
Figure 14A:
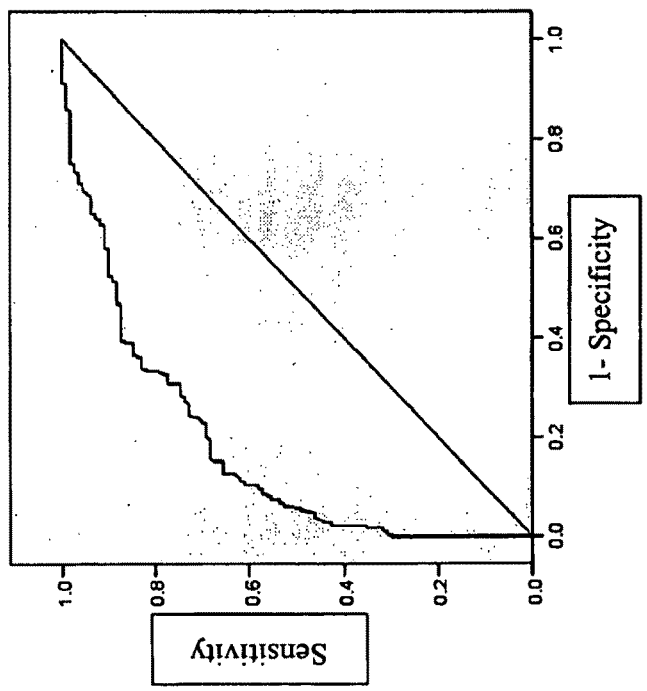
Figure 14B:
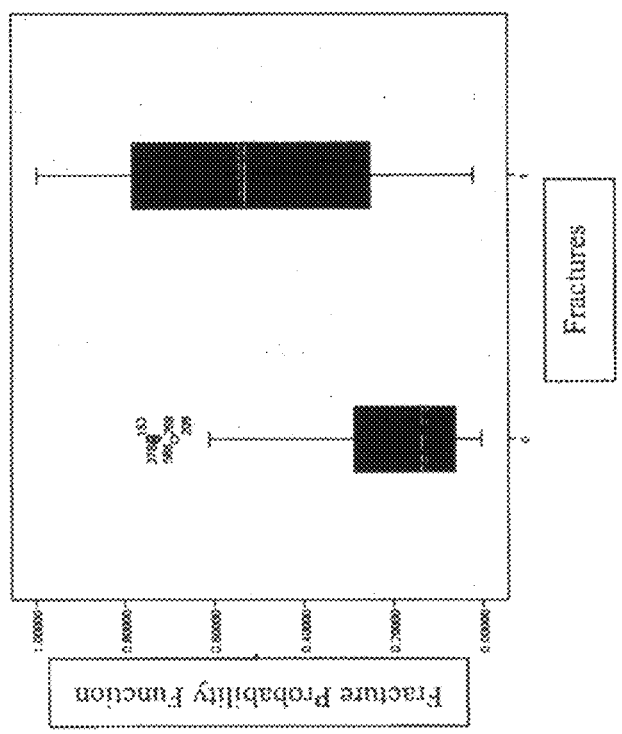
Figure 15A:
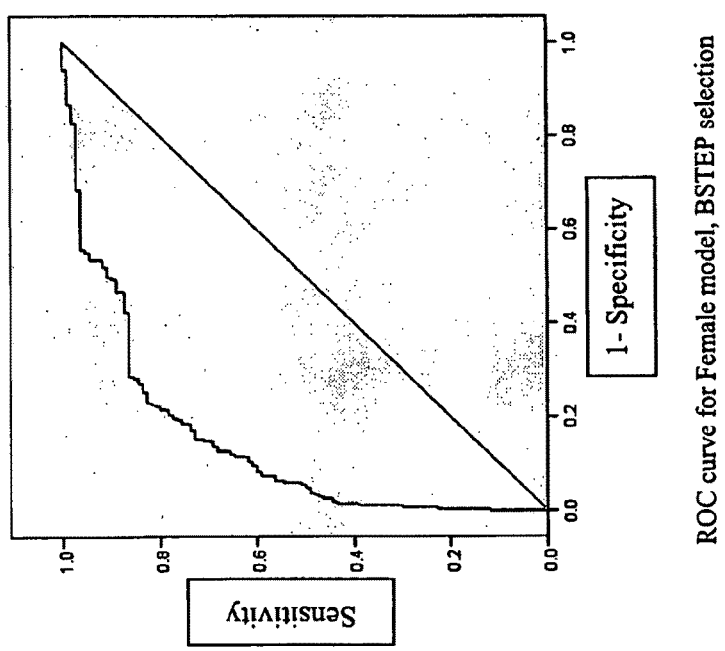
Figure 15B:
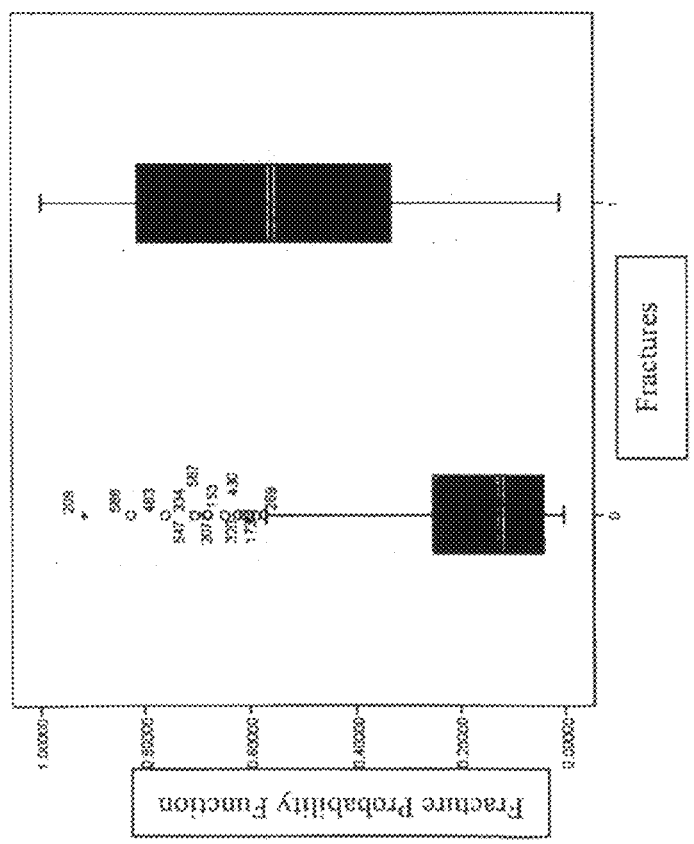

Lists the sensitivity, specificity, LR+ values for the models represented in FIGS. 10 to 15.

FIG. 17

(A) and (B) Tables showing data for calculation of probability function using the variables for the general FSTEP and BSTEP models.

FIG. 18

(A) and (B) Tables showing data for calculation of probability function using the variables for the male FSTEP and BSTEP models.

FIG. 19

(A) and (B) Tables showing data for calculation of probability function using the variables for the female FSTEP and BSTEP models.

In FIGS. 17 to 19, regression probability functions are built using the Statistical Package for the Social Sciences (SPSS Inc. Headquarters, Chicago, Ill., USA) version 14.0. SPSSv14. B is the coefficient associated to each genotype in the probability function. ET is the error in the calculation of B. Wald is the statistical test. gI is the degrees of freedom. Sig. Is the value of B for the Wald test. Exp (B) is Relative Risk.

DETAILED DESCRIPTION OF THE INVENTION

Osteoporosis is characterised by low bone mass (clinically determined by bone mineral density—BMD) and increased susceptibility to fractures, particularly of the hip (femoral), spine (vertebral) and wrist. Generally the disease is diagnosed by determining BMD—but often not until a fracture has occurred.

Using the Osteochip microarray of the present invention, and clinical investigation, the inventors have identified a number of profiles (based on informative SNPs and clinical variables) which can be used to predict low BMD and fractures. The inventors have thus developed means (in particular models) for accurately predicting low BMD values and fractures (e.g. fractures of the hip, spine and wrist) particularly in osteoporotic patients.

Accordingly, in one aspect the invention provides methods for prognosis of BMD and/or fractures. Thus the invention may provide methods for early prognosis or diagnosis of osteoporosis. For example, the invention provides methods for predicting the following phenotypes:
1. fractures (in any part of the body);
2. vertebral fractures; and
3. fractures of the wrist and/or hip and/or spine.

The fractures are in general non-traumatic.

The invention further provides methods for predicting the following quantitative traits:
3. lumbar spine bone mineral density (LSBMD); and
4. femoral neck bone mineral density (FNBMD).

Such accurate prediction facilitates selection of the most appropriate therapy for each patient, and may (particularly if used at an early stage in the disease) allow alteration of disease course from severe to more mild form. In some cases this could mean preventing the apparition of fractures.

In an initial study the inventors selected a population-based cohort of 904 postmenopausal Italian women and elderly men and 125 consecutive Italian patients with non traumatic fractures as in Example 2.

Each patient was assessed to determine the presence of the fracture phenotypes as in Example 2, and to determine the LSBMD and FNBMD. Each patient was also tested to determine outcomes for various clinical variables and genotyped at each of 112 single nucleotide polymorphisms (SNPs) (Table 5) in 57 genes, some of which have been previously associated with osteoporosis risk and/or physiopathology (Example 2 and Table 4).

The inventors used genetic analysis to select particular SNPs for further study (Example 2). Genotype-phenotype and genotype-quantitative trait associations were analysed using linear or logistic regression. As the incidence of the disease is different in men and women, the genotype-phenotype and genotype-quantitative trait associations were calculated separately for men and women.

In this way the inventors established probability functions (based on combinations of informative SNPs and clinical variables) that allow reliable discrimination between patients with alternative forms of each phenotype analysed (risk of fractures or vertebral fractures) with high specificity, sensitivity and accuracy. The inventors also established quantitative functions (based on combinations of informative SNPs and clinical variables) which allow reliable estimation of LSBMD and FNBMD.

The informative SNPs and clinical variables included in each probability or quantitative function for each phenotype or quantitative trait are shown in Table 5 (FIG. 5).

The fractures probability functions (for males or females) allow discrimination between patients having and not having the fractures phenotype in Example 2 (in Example 2 the fractures phenotype is having a non-traumatic fracture in any position of the body). The vertebral fractures probability functions (for males and females) allow discrimination between patients having and not having the vertebral fractures phenotype. The probability functions calculate the risk or probability of an individual developing fractures, based on the outcomes for the informative variables in Table 5. The graphs in FIGS. 6.1, 6.2, 7.1, 7.2 show probability function values for the individuals (of known, clinically determined phenotype) in the clinical validation (Example 2).

The LSBMD and FNBMD quantitative functions allow estimation of LSBMD and FNBMD respectively. The quantitative functions estimate BMD values of an individual, based on the outcomes for the informative variables in Table 5. FIG. 8 show $R^2$ values for the individuals (of known, clinically determined phenotype) in the clinical validation (Example 2).

Thus the fractures variables for men and women in Table 5 are those which are informative for predicting fractures. The vertebral variables in Table 5 are those which are informative for predicting vertebral fractures. The LSBMD variables in Table 5 are those which are informative for estimating LSBMD. The FNBMD variables in Table 5 are those which are informative for estimating FNBMD.

The inventors then carried out a further study of fractures. Using samples from the same study population as in Example 2, the inventors again genotyped the population at each of the SNPs in Table 1N1B but using optimised probes and primers (Example 3 and Table 2C and 3C).

The inventors again studied genotype-phenotype associations, but in this study the factures phenotype was considered to be having a (non-traumatic) fracture in the spine (vertebral), hip (femoral) or wrist. The inventors carried out their investigation for the male population, the female population, and for the whole population (male and female).

In each case the inventors established 2 probability functions (FSTEP and BSTEP) each based on combinations of informative SNPs and clinical variables, and each of which allows reliable discrimination between patients with alternative forms of the Example 3 fractures phenotype (WSHfractures) with high specificity, sensitivity and accuracy.

The variables (SNPs and clinical variables) included in each function are shown in FIG. 9.

These new fractures probability functions (for males or females or both) allow discrimination between patients having the fractures phenotype (as defined in Example 3) and those not. The probability functions can be used to calculate the risk or probability of an individual developing wrist, hip or spine fractures, based on the outcomes for the informative variables in FIG. 9. FIG. 10A-15A show the ROC curves for each of the models developed by the inventors. Sensitivity, specificity and positive likelihood ratios (LR+) for each of the models are in FIG. 16. The graphs in FIGS. 10B-15B show probability function values for the individuals (of known, clinically determined phenotype) in the clinical validation (Example 3).

The inventors realised that by determining the outcomes of the informative variables for a particular phenotype or quantitative trait, it was possible to determine the corresponding phenotype or the corresponding quantitative value in the subject with a new accuracy and reliability, and without the need to analyse a large number of variables.

Thus the clinical and SNP variables identified, and the models constructed using them, provide new means for predicting the development of each of the corresponding phenotypes, and the quantitative traits, in a subject. Thus the invention provides methods for the prognosis of osteoporosis and in particular for predicting the risk of fractures (for example, vertebral fractures, or any of wrist/spine/vertebral fractures) and for estimating LSBMD and FNBMD as described herein.

Osteoporosis is a complex disorder. The course of disease progression is highly variable, with highly heterogeneous disease behaviour. A clinical diagnosis of osteoporosis may be made based on WHO criteria on the basis of BMD (Tscore+Zscore).

Osteoporosis phenotype as referred to herein may refer to the fractures phenotype as defined in Example 2 or Example 2 or to the vertebral fractures phenotype in Example 2. Existence of fractures can be determined on the basis of clinical data.

The "fractures phenotype in Example 2" refers to the existence of one or more non-traumatic factures in any part of the body. This is referred to hereafter as the fractures phenotype. A patient is typically considered to display the fractures phenotype if he or she is clinically determined to have one or more non-traumatic fractures in any part of the body.

The "fractures phenotype in Example 3" refers to the existence of one or more non-traumatic fractures in any of the wrist, spine (vertebral) or hip (femoral). This is referred to hereafter as the WSHfractures phenotype. A patient is typically considered to display the WSHfractures phenotype if he or she is clinically determined to have one or more non-traumatic fractures in any of the wrist, hip or spine.

Fractures may be clinically diagnosed by for example X-ray.

Vertebral fractures refer to fractures occurring in the spine. Such fractures may be clinically diagnosed by for example by X-RAY. A patient is typically considered to display the vertebral fractures phenotype if he or she is clinically determined to have one or more non-traumatic fractures in the spine.

Osteoporosis quantitative trait may refer to LSBMD and/or FNBMD.

Lumbar spinal bone mineral density (LSBMD) and femoral neck bone mineral density (FNBMD) may be clinically determined using a BMD test. For example, a Dual Energy X-Ray Absorptiometry (DXA) scan may be used.

The present methods may be used to prognose one or more of the fractures phenotype, the WSHfractures phenotype, or the vertebral fractures phenotype or to estimate LSBMD and FNBMD in a subject. Thus the present methods may be useful for (reliably) determining whether a given phenotype (e.g. fractures, WSHfractures, or vertebral fractures) or a given quantitative trait value (LSBMD and FNBMD) already exists in a subject and/or for determining whether a given phenotype (e.g. fractures, WSHfractures, or vertebral fractures) or a given quantitative trait (LSBMD and FNBMD) value is likely to develop in the subject. Typically the method results in a probability of a given phenotype existing or developing in a subject. Typically the method results in an estimation of a quantitative trait value existing or developing in a subject.

In general the subject is a human. The subject may be for example, Chinese, Japanese or a Caucasian. Preferably the subject is a Caucasian, such as an Italian individual. The subject may be male or female and male or female variables may be selected accordingly, as described herein. The subject may be for example, a post-menopausal woman or an elderly man. In general the subject may be a man or woman over the age of 60.

In one aspect, the subject has already been diagnosed with osteoporosis according to WHO existing methods and criteria (Zscore+Tscore). The subject may be already diagnosed with osteoporosis. In another aspect, the subject may not have been diagnosed. Such subjects may be presenting symptoms typical of or associated with osteoporosis. In one aspect a subject may have been provisionally assigned a fractures or vertebral fractures phenotype, or a WSHfracture phenotype and LSBMD or FNBMD values. Thus the present methods may be used to confirm prognosis and estimations, or to make new prognosis and estimations.

The present methods involve determining an outcome for each of a number of variables or predictors. The variables are listed in Tables 5 and FIG. 9 and comprise 112 SNPs, together with clinical variables. Tables 1B, and 5, and FIG. 9 provide RefSNP codes (rs#) for each SNP. These are taken from the Single Nucleotide Polymorphism Database (dbSNP) curated by the National Center for Biotechnology Information (NCBI) as at 24 Nov. 2006 (Table 5) and 6 Jul. 2007 (Table 1B and FIG. 9)].

Table 5 lists SNP variables and clinical variables which are informative for predicting the fractures phenotype and the vertebral fractures phenotype (in males and females) and for estimating LSBMD and FNBMD (in males and females). The variables marked with an X in the column for a given phenotype or trait are those variables which are informative for predicting or estimating that phenotype or trait. These are the variables included in the predictive models (or probability functions) established in Example 2. Herein, the variables which are listed as informative for predicting or estimating a phenotype or trait in Table 5 are referred to as "phenotype name variables" or "quantitative trait name variables". Thus, for example the "female fractures variables" refers to the SNP and clinical variables which are marked with an X in the Females Fractures column of Table 5 and which are therefore informative for predicting the likelihood of the fractures phenotype in females.

Similarly FIG. 9 lists SNP variables and clinical variables which are informative for predicting the WSHfractures phenotype. In Example 3, six different models were established for predicting the WSHfractures phenotype. These are separated into 6 different columns in FIG. 9. There are 2 models (FTEP and BSTEP) which can be used to predict the likelihood of or prognosing the WSHphenotype in either a male or a female subject (general models), 2 models (FTEP and BSTEP) for predicting the likelihood of or prognosing the WSHphenotype in a male subject (male models), and 2 models (FTEP and BSTEP) for predicting the likelihood of or prognosing the WSHphenotype in a female subject (female models). The column for each model lists the SNP variables and clinical variables which are included in that predictive model. Thus, for example, the male FSTEP model includes the SNP variable rs3736228 and the clinical variable AGE. Herein the variables which are included in a model for predicting WSHfracture phenotype in FIG. 9 are referred to as "model name variables". Thus, for example, the SNP variable rs3736228 and the clinical variable AGE, which are included in the male FSTEP model are referred to as maleFSTEP model variables.

The outcome for a given SNP is the identity of the nucleotide at that position in the genomic DNA sequence of a subject or the genotype of the subject for that SNP. Thus an outcome for a given SNP may be A, T, C or G.

The present methods may also comprise determining or using an outcome for one or more clinical variables for a subject. These clinical variables are also listed in Table 5 and FIG. 9.

Age refers to the age of the subject in years. Menopause age in a female subject refers to the age in years of the onset of menopause. Menarche age in a female subject refers to the age in years of the onset of menarche. BMI is the body mass index and may be calculated according to known methods. The outcomes for the clinical (non-SNP) variables are therefore age, menopause age, menarche age and Body Mass Index (BMI), as shown.

Accordingly the invention in one aspect provides a method for predicting an osteoporosis phenotype or quantitative trait described herein in a subject, comprising the step of determining, for that subject, outcomes for one or more variables (e.g. one or more SNP variables and one or more clinical variables) listed as informative for predicting the phenotype or trait in Table 5 or FIG. 9. In one aspect the invention provides a method for prognosing the fractures phenotype or vertebral fractures phenotype in a subject comprising the step of determining outcomes for variables listed in Table 5 for that subject. The invention also provides a method for estimating LSBMD and FNBMD in a subject comprising the step of determining outcomes for variables listed in Table 5 for that subject.

The invention also provides a method for predicting the WSHfractures phenotype in a subject comprising the step of determining outcomes for variables listed in FIG. 9 for the subject. For example a method may comprise determining or obtaining outcomes for the general FSTEP model variables and/or the general BSTEP model variables and/or the male FTEP model variables and/or the male BSTEP model variables and/or the female FSTEP model variables and/or the female FTEP model variables. For a male subject, a method may comprise determining or obtaining outcomes for the variables in each of the male models and/or the general model. Similarly for a female subject, a method may comprise determining outcomes for the variables in each of the female models and/or the general model. Thus WSHfractures phenotype in a male may be predicted using either or both of the male models in FIG. 9, and/or the general model in FIG. 9. Similarly, the WSHfractures phenotype in a female may be predicted using either or both of the female models in FIG. 9, and/or the general model in FIG. 9. In one aspect a method for predicting WSHfractures phenotype comprises use of one or more of the BSTEP models in FIG. 9. Using a model typically refers to obtaining or determining outcomes for model variables, e.g. all of the model variables and using these outcomes to predict or determine the phenotype as described herein.

The present method may thus be for prognosis of the fractures phenotype, the vertebral fracture phenotype and/or the WSHfractures phenotype, and/or for estimating LSBMD and FNBMD. The method may be used to prognose the fractures phenotype and/or the vertebral fracture phenotype using variables selected from the (male or female) fractures variables and the (male or female) vertebral fractures variables in Table 5. The method may be used to estimate LSBMD and FNBMD using variables selected from the (male or female) LSBMD and (male or female) FNBMD variables in Table 5. The method may be used to prognose WSHfractures phenotype using variables selected from the model variables listed for each of the models in FIG. 9.

Preferably the above methods comprise determining outcomes for all of the male or female fractures variables, and/or all of the male or female vertebral fractures variables, and/or all of the LSBMD variables and/or all of the FNBMD variables (or SNP variables) listed as informative for predicting the given phenotype or estimating the given trait in Table 5. For example, for prognosing the fractures phenotype preferably all of the male or female fractures variables (or SNP variables) in Table 5 are tested or used. It is believed that this will produce the most accurate prediction of disease phenotype or trait.

Similarly, for any of the predictive models in FIG. 9, it is preferred that all of the model variables listed for that model are used to predict WSHfractures phenotype.

However, it is envisaged that the diagnostic method may be carried out (to a lower degree of accuracy) using fewer than the listed variables (or SNP variables) listed as informative for predicting a given phenotype or trait in Table 5, or for inclusion in a model in FIG. 9.

Thus for example, if x is the number of fractures, vertebral fractures, LSBMD or FNBMD variables (or SNP variables) listed as informative for predicting a given phenotype or estimating a trait in Table 5, the method may comprise determining the outcomes of (at least) (x-n) of the fractures, vertebral fractures, LSBMD or FNBMD variables (or SNP variables) where n is any number from 1 to 10 (1, 2, 3, 4, 5, 6, 7, 8, 9 or 10), and using the outcomes of these variables to predict the given phenotype or estimate the quantitative trait. Preferably the minimum number of variables used is the number that allow a discrimination power significantly greater than the discrimination power provided by chance (Press's Q test) (Hair J, Black B, Babin B, Anderson R, Tatham R. Multivariate Data Analysis. 6/E. Prentice Hall 2006).

For example, Table 5 lists 38 fracture variables for females, including 35 SNP variables which are informative for prognosing the fractures phenotype in females. Preferably the present method comprises determining outcomes for all 38 fracture variables or all 35 fracture SNP variables, and predicting the phenotype on the basis of these outcomes. However, in some cases, the method may comprise determining outcomes for as few as 20, 15 or 10 of these variables or SNP variables—the minimum number of variables being the number that allow a discrimination power significantly greater than the discrimination power provided by chance (Press's Q test)(as above).

Similarly, if x is the number of model variables (or SNP variables) listed as informative for predicting WSHfractures phenotype for a model in FIG. 9, the method may comprise determining the outcomes of (at least) (x-n) of the model variables (or SNP variables) where n is any number from 1 to 10 (1, 2, 3, 4, 5, 6, 7, 8, 9 or 10), and using the outcomes of these variables to predict the phenotype. Preferably the minimum number of variables used is the number that allow a discrimination power significantly greater than the discrimination power provided by chance (Press's Q test) (Hair J, Black B, Babin B, Anderson R, Tatham R. Multivariate Data Analysis. 6/E. Prentice Hall 2006).

For example, FIG. 9 lists 10 general BSTEP model variables, including 9 SNPs which are informative for prognosing WSHfractures phenotype in the general (male and female) population. Preferably the present method comprises determining outcomes for all 10 BSTEP fracture variables or all 9 SNP variables, and predicting the phenotype on the basis of these outcomes. However, in some cases, the method may comprise determining outcomes for as few as 8, 7, 6, or 5 of these variables or SNP variables—the minimum number of variables being the number that allow a discrimination power significantly greater than the discrimination power provided by chance (Press's Q test)(as above).

At least one of the fractures, vertebral fractures, model, LSBMD and/or FNBMD variables such as SNP variables is tested in the present methods.

In the case of the female fracture variables in Table 5, it is preferred that at least 2, for example at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 of the variables, such as SNP variables are tested for outcomes and used in the prediction. As in Example 2, the inventors have found that the present methods (based on female fracture variables in Table 5) may be used to prognose fractures phenotype in (Italian) females and assign phenotype with sensitivities greater than 55% and specificities of over 95%, with LR value of 11. Thus the present methods provide a more accurate and reliable means of prognosing fractures phenotype in females than current conventional methods.

In the case of the male fractures variables in Table 5, it is preferred that at least 2, for example at least 3, 4, 5, 6, 7, 8, 9, 10, 11, 12, 13, 14, 15, 16, 17, 18, 19, 20, 21, 22, 23, 24, 25, 26, 27 or 28 of the variables, such as SNP variables are tested for outcomes and used in the prediction. As in Example 2, the inventors have found that the present methods (based on male fractures variables in Table 5) may be used to prognose fractures phenotype in (Italian) males and assign phenotype with sensitivities greater than 57% and specificities of over 95%, with LR value of 11.4. Thus the present methods provide a more accurate and reliable means of prognosing fractures phenotype in males than current conventional methods.

In the case of the female vertebral fractures variables in Table 5, it is preferred that at least 2, for example, at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 of the variables, such as SNP variables are tested for outcomes and used in the prediction. As in Example 2, the inventors have found that the present methods (based on females vertebral fractures variables in Table 5) may be used to prognose vertebral fractures phenotype in (Italian) females and assign phenotype with sensitivities greater than 72% and specificities of over 95%, with LR value of 14. Thus the present methods provide a more accurate and reliable means of prognosing vertebral fractures phenotype in females than current conventional methods.

In the case of the male vertebral fractures variables in Table 5, it is preferred that at least 2, for example, at least 3, 4, 5, 6, 7, 8, 9, 10, 11, 12, 13, 14, 15, 16, 17, 18, 19, 20, 21, 22, 23, 24, 25, 26, 27, 28, 29 or 30 of the variables such as SNP variables are tested for outcomes and used in the prediction. As in Example 2, the inventors have found that the present methods (based on male vertebral fractures variables in Table 5) may be used to prognose vertebral fractures phenotype in (Italian) males and assign phenotype with sensitivities greater than 71% and specificities of over 94%, with LR value of 11.8. Thus the present methods provide a more accurate and reliable means of prognosing vertebral fractures phenotype in males than current conventional methods.

In the case of the female LSBMD variables in Table 5, it is preferred that at least 2, for example at least 3, 4, 5, 6, 7, 8, 9, 10, 11, 12, 13, 14, 15, 16, 17, 18, 19 or 20 of the variable such as SNP variables are tested for outcomes and used in the prediction. As in Example 2, the inventors have found that the present methods (based on female LSBMD variables in Table 5) may be used to estimate LSBMD in (Italian) females with an $R^2$ of 0.3. Thus the present methods provide a more accurate and reliable means of estimating LSBMD with the age in females than current conventional methods.

In the case of the male LSBMD variables in Table 5, it is preferred that at least 2, for example at least 3, 4, 5, 6, 7, 8, 9, 10, 11, 12, 13, 14, 15, 16 17, 18, 19, 20, 21, 22, 23, 24, 25, 26, 27, 28, 29, 30, 31, 32, 33 or 34 of the variables such as SNP variables are tested for outcomes and used in the prediction. As in Example 2, the inventors have found that the present methods based on male LSBMD variables in Table 5) may be used to estimate LSBMD in (Italian) males with an $R^2$ of 0.38. Thus the present methods provide a more accurate and reliable means of estimating LSBMD with the age in males than current conventional methods.

In the case of the female FNBMD variables in Table 5, it is preferred that at least 2, for example at least 3, 4, 5, 6, 7, 8, 9, 10, 11, 12, 13, 14, 15, 16, 17, 18, 19, 20, 21 or 22 of the variables such as SNP variables are tested for outcomes and used in the prediction. As in Example 2, the inventors have found that the present methods (based on female FNBMD variables in Table 5) may be used to estimate FNBMD in (Italian) females with an $R^2$ of 0.32. Thus the present methods provide a more accurate and reliable means of estimating FNBMD with the age in females than current conventional methods.

In the case of the male FNBMD variables in Table 5, it is preferred that at least 2, for example at least 3, 4, 5, 6, 7, 8, 9, 10, 11, 12, 13, 14, 15, 16, 17, 18, 19, 20, 21 or 22 of the variables such as SNP variables are tested for outcomes and used in the prediction. As in Example 2, the inventors have found that the present methods (based on male FNBMD variables in Table 5) may be used to estimate FNBMD in (Italian) males with an $R^2$ of 0.35. Thus the present methods provide a more accurate and reliable means of estimating FNBMD with the age in males than current conventional methods.

In the case of the general FSTEP model variables in FIG. 9, it is preferred that at least 2, for example at least 3, 4, 5, or 6 of the variables, such as SNP variables are tested for outcomes and used in the prediction. For example, a method may comprise determining for the subject, an outcome for each of the general FSTEP variables listed in FIG. 9. Use of these variables allows prognosis of WSHfractures phenotype in an Italian population with an LR+ of 7.7 (see Example 3 and FIG. 16).

In the case of the general BSTEP model variables in FIG. 9, it is preferred that at least 2, for example at least 3, 4, 5, 6, 7, 8, 9 or 10 of the variables, such as SNP variables are tested for outcomes and used in the prediction. For example, a method may comprise determining for the subject, an outcome for each of the general BSTEP variables listed in FIG. 9. Use of these variables allows prognosis of WSHfractures phenotype in an Italian population with an LR+ of 7.8 (see Example 3 and FIG. 16).

In the case of the male FSTEP model variables in FIG. 9, it is preferred that at least 2, of the variables are tested for outcomes and used in the prediction. For example, a method may comprise determining for the subject, an outcome for each of the male FSTEP variables listed in FIG. 9. Use of these variables allows prognosis of WSHfractures phenotype in an Italian population with an LR+ of 5.5 (see Example 3 and FIG. 16).

In the case of the male BSTEP model variables in FIG. 9, it is preferred that at least 2, for example at least 3, 4, 5, 6, 7, 8, 9 or 10 of the variables, such as SNP variables are tested for outcomes and used in the prediction. For example, a method may comprise determining for the subject, an outcome for each of the male BSTEP variables listed in FIG. 9. Use of these variables allows prognosis of WSHfractures phenotype in an Italian population with an LR+ of 8.7 (see Example 3 and FIG. 16).

In the case of the female FSTEP variables in FIG. 9, it is preferred that at least 2, for example at least 3, 4, 5, 6, or 7 of the variables, such as SNP variables are tested for outcomes and used in the prediction. For example, a method may comprise determining for the subject, an outcome for each of the female FSTEP variables listed in FIG. 9. Use of these variables allows prognosis of WSHfractures phenotype in an Italian population with an LR+ of 9.4 (see Example 3 and FIG. 16).

In the case of the female BSTEP variables in FIG. 9, it is preferred that at least 2, for example at least 3, 4, 5, 6, 7, 8, 9, 10, 11 or 12 of the variables, such as SNP variables are tested for outcomes and used in the prediction. For example, a method may comprise determining for the subject, an outcome for each of the female BSTEP variables listed in FIG. 9. Use of these variables allows prognosis of WSHfractures phenotype in an Italian population with an LR+ of 10.4 (see Example 3 and FIG. 16).

In one instance, the method comprises prognosing fractures phenotype and estimating LSBMD and FNBMD. For example, the method may comprise determining outcomes for fractures variables, vertebral fractures, LSBMD and/or FNBMD variables selected as above or any combination thereof, as appropriate to the subject, e.g male or female. The method may comprise determining an outcome for each of the variables in Table 5 or each of the male or female variables in Table 5. Thus, for example, it may be possible to simultaneously test a subject for osteoporosis and at the same time determine the likelihood of development of fractures/vertebral fractures and estimating LSBMD and FNBMD.

For example a method may comprise determining likelihood of fractures phenotype in a subject and estimating LSBMD and/or FNBMD using the outcomes of fractures variables in Table 5 and LSBMD and/or FNBMD variables in Table 5. The variables may be selected as described herein, and as appropriate to a male or female subject.

Similarly a method may comprise determining the likelihood of the WSHfractures phenotype in a subject using one or more of the models described in FIG. 9 as described herein, and estimating LSBMD and/or FNBMD using the LSBMD-variables and/or the FNBMD variables in Table 5.

In general the methods involve genotyping at least one SNP. In some instances the Table 5 or FIG. 9 variables for which an outcome is determined in the present methods are only SNPs listed in Table 5 or FIG. 9 (and not clinical variables) and therefore the outcomes are all genotypes.

In some aspects the present methods may include determining other factors for a subject. For example, the subject may be genotyped for one or more other genetic variations (such as other SNPs not listed in Table 5 or FIG. 9). These may be mutations associated with osteoporosis or another condition. Other markers (SNPs) associated with other diseases may also be determined. The present methods may also be used in conjunction with standard clinical tests for osteoporosis as described herein. For example, the methods may be used in conjunction with a clinical test for BMD.

The present methods allow accurate prediction of a fractures, vertebral fractures or WSHfractures phenotype and/or LSBMD/FNBMD estimation based on a relatively small number of informative variables (in particular, SNPs). This can be advantageous in that it allows use of genotyping techniques that would not necessarily be suitable for large scale SNP screening, as well as larger scale genotyping methods.

In general, even if a larger number of SNPs or genetic variations or factors are tested in the present methods, prediction of fractures/vertebral fractures phenotype and LSBMD/FNBMD estimation can be made based only on outcomes of informative variables listed in Table 5 and/or FIG. 9 and selected as described above. The variables in Table 5 and/or FIG. 9, selected in type and number as described above, are sufficient for the prediction. Therefore in one example, the present methods allow prognosis of fractures/vertebral fractures phenotypes and LSBMD/FNBMD estimation based on (at a maximum) the outcomes of Table 5 variables or SNP variables selected in number and type as described above.

Similarly, WSHfractures phenotype may be predicted based on (at a maximum) the outcomes of model variables in FIG. 9, selected as described herein. For example, a prediction for a male subject may be made based on the outcomes of (at a maximum) the male FSTEP model variables and/or the male BSTEP model variables and/or the general FSTEP model variables and/or the general BSTEP model variables.

In some instances though, it may be that some additional variables or SNP variables or factors are used in the prediction or estimation. Preferably in the present methods, prognosis or diagnosis is made based on the outcomes of a maximum of 130, 120, 110, 100, 90, 80, 70, 60, 50, 45, 40, 35, 30, 26, 24, 20, 10, 5 or 4 variables such as SNPs or osteoporosis associated SNPs, comprising (or consisting of) the Table 5 and/or FIG. 9 SNP variables selected as described above.

In one aspect the method may involve genotyping a maximum of 130, 120, 110, 100, 90, 80, 70, 60, 50, 40, 30, 26, 24, 20, 10, 5 or 4 SNPs or osteoporosis associated SNPs. The method may involve genotyping a maximum of the 11.2 SNPs in Table 5. In some instances, the method comprises genotyping at a maximum, the fractures SNP variables, vertebral fractures SNP variables, FIG. 9 model SNP variables, LSBMD SNP variables and/or FNBMD SNP variables selected as described above.

In some instances, the only osteoporosis associated SNPs which are genotyped in the method are those selected in number and type from Table 5 and/or FIG. 9 as described above.

Preferably the number and combination of variables such as SNPs used to construct a model for predicting a phenotype or trait according to the invention, is such that the model allows prediction to be made with an LR+ value of at least 5, such as at least 6, 7, 8, 9, or 10. Calculation of LR+ values is described herein.

Once an outcome is determined for each of the selected variables (e.g. SNP variables) for prediction of a given phenotype or estimation of a quantitative trait, these outcomes are then used to predict phenotype or estimate quantitative trait. The outcomes are used or inserted in a suitable probability function or quantitative function (for prediction of that phenotype or estimation of that quantitative trait) and a probability function value or quantitative function value is calculated. Outcomes may be codified for use in the probability function or quantitative function and calculation of the probability function or quantitative function value. In the case of probability function, the probability function value is then compared with probability function values obtained for a population of individuals of known (clinically determined) phenotype. For example, this may be done by comparison with a graph showing the distribution of values in the population, such as those in FIGS. 6.1, 6.2, 7.1 and 7.2. It can thus be determined whether a test individual is at high or low risk of developing the phenotype based on the phenotypic group to which the test probability function value belongs.

A suitable probability function or quantitative function for a given phenotype or quantitative trait may be derived by methods as set out in the present Examples and described below. Typically a study population of individuals is provided. These individuals are of known (clinically determined) phenotype and/or quantitative trait with respect to the phenotype or trait that the probability or quantitative function will be used to determine. Clinical diagnosis and phenotype determination of osteoporosis can be made following Clinical criteria of World Health Organization (WHO) based on Zscore and Tscore. Each of the osteoporosis phenotypes and traits which may be assessed according to the invention may be clinically diagnosed as described herein.

In one example, the individuals in the study population may meet one or more or all of the inclusion criteria for the study population in Example 2:

The population may be for example, a Chinese, Japanese or a Caucasian population, such as Italian population. The population may be male or female. If the probability function or quantitative function to be derived is based on female variables in Table 5 or female model variables in FIG. 9, preferably the population is of female individuals. If the probability function or quantitative function to be derived is based on male variables in Table 5 or male model variables in FIG. 9, preferably the population is of male individuals. In a mixed population, the distribution of males and females is preferably equilibrated. The population may comprise menopausal women and/or elderly men. Men and/or women may be over the age of 60. Preferably the population used for deriving the probability functions/quantitative functions comprises a representative sample of the population in which the probability functions will be applied.

In general at least n individuals are included in the study population. Typically n is 300-1200, for example 400, 500 or 600. Preferably there are approximately equal numbers of individuals with alternative phenotypes. Thus the population is preferably approximately 50% phenotype A and 50% phenotype B. However, the ratios may be for example, 60%/40%, 70%/30% or any statistically acceptable distribution.

The individuals in the study population are then tested and outcomes for each of the informative variables for the particular phenotype or quantitative trait (as listed in Table 5 and/or FIG. 9 and selected in number and type as described above for the diagnostic methods) are determined for each individual. Testing, e.g. genotyping, may be carried out by any of the methods described herein, e.g. by microarray analysis as described herein. This provides a number of outcomes for each individual.

Multiple logistic regression analysis is then carried out using as the dependent variable the clinically determined disease phenotype and as independent variables the outcomes of the informative variables. Probability functions are thereby derived. In general the probability functions are able to distinguish between the individuals of different phenotype in the study population in a statistically significant way, for example, at $p \leq 0.05$ in a t-test.

Multiple lineal regression analysis is then carried out using as the dependent variable the quantitative trait and as independent variables the outcomes of the informative variables. Quantitative functions are thereby derived. In general the quantitative functions are able to estimate the quantitative trait in the study population in a statistically significant way, for example, at $p \leq 0.05$ in a t-test.

Probability function values can then be calculated for each individual of known phenotype in the study population and plotted in a suitable graph. For example, suitable graphs are shown in FIGS. 6.1, 6.2, 7.1 and 7.2, and in FIGS. 10B-15B.

Thus for example, in deriving a probability function for use in predicting fractures phenotype, e.g in females using the Table 5 variables, a study population of individuals suffering from fractures phenotype and individuals not suffering from fractures phenotype is provided. Each female individual may then be tested to determine an outcome for each of the 35 female fractures SNP variables (or each of the 38 variables) in Table 5. Multiple logistic regression is performed on the "outcomes" and "phenotype" data and a probability function is derived which is able to distinguish between the two phenotypic groups in the study population in a statistically significant way.

Thus for example, in deriving a quantitative function for use in estimating LSBMD, e.g. in females, a study population of individuals with a wide range of LSBMD is provided. Each female individual may then be tested to determine an outcome for each of the 17 female LSBMD SNP variables in Table 5 (or all of the female LSBMD variables in Table 5). Multiple lineal regression is performed on the "outcomes" and "phenotype" data and a quantitative function is derived which is able to estimate LSBMD in the study population in a statistically significant way.

In one aspect therefore the invention further provides a method of deriving a probability function or quantitative function for use in prognosing an osteoporosis phenotype or estimating an osteoporosis quantitative trait respectively, comprising:

(i) providing a population of individuals each of known clinically determined phenotype or quantitative trait with respect to the phenotype or trait;

(ii) determining ex vivo the outcomes of a set of variables for each individual in the population thereby obtaining a set of outcomes for each individual;
and (iii)
  (a) applying multiple logistic regression analysis to the outcomes obtained in (ii) and the known phenotypes obtained in (i); and
  (b) thereby deriving a probability function which produces a statistically significant separation of individuals of different phenotype in the population;
and/or iv)
  (a) applying multiple lineal regression analysis to the outcomes obtained in (ii) and the quantitative traits obtained in (i); and
  (b) thereby deriving a quantitative function which produces a statistically significant estimation of the quantitative trait of individuals in the population;

wherein:
(a) the phenotype is the fractures or vertebral fractures phenotype and the set of variables is selected from the set of fractures variables or vertebral fractures variables in Table 5; and/or
(b) the quantitative trait is LSBMD/FNBMD and the set of variables is selected from the set of LSBMD or FNBMD variables in Table 5; and/or
(c) the phenotype is the WSHfractures phenotype and the set of variables is selected from the model variables for any of the models in FIG. 9.

In particular, wherein:
(a) the phenotype is fractures in female subjects and the set of variables is selected from or consists of the set of female fracture variables in Table 5;
(b) the phenotype is fractures in male subjects and the set of variables is selected from or consists of the set of male fracture variables in Table 5;
(c) the phenotype is vertebral fractures in female subjects and the set of variables is selected from or consists of the set of female vertebral fractures variables in Table 5;
(d) the phenotype is vertebral fractures in male subjects and the set of variables is selected from or consists of the set of male vertebral fractures variables in Table 5;
(e) the quantitative trait is lumbar spine bone mineral density (LSBMD) in female subjects and the set of variables is selected from or consists of the set of LSBMD female variables in Table 5;
(f) the quantitative trait is LSBMD in male subjects and the set of variables is selected from or consists of the set of LSBMD male variables in Table 5;
(g) the quantitative trait is femoral neck bone mineral density (FNBMD) in female subjects and the set of variables is selected from or consists of the set of FNBMD female variables in Table 5;
(f) the quantitative trait is FNBMD in male subjects and the set of variables is selected from or consists of the set of FNBMD male variables in Table 5;
(g) the phenotype is WSHfractures in female subjects and the set of variables is selected from or consists of the set of female FSTEP model variables in FIG. 9;
(h) the phenotype is WSHfractures in female subjects and the set of variables is selected from or consists of the set of female BSTEP model variables in FIG. 9;
(i) the phenotype is WSHfractures in male subjects and the set of variables is selected from or consists of the set of male FSTEP model variables in FIG. 9;
(j) the phenotype is WSHfractures in male subjects and the set of variables is selected from or consists of the set of male BSTEP model variables in FIG. 9;
(k) the phenotype is WSHfractures in a male or female subject and the set of variables is selected from or consists of the set of general FSTEP model variables in FIG. 9; and/or
(l) the phenotype is WSHfractures in a male or female subject and the set of variables is selected from or consists of the set of general BSTEP model variables in FIG. 9.

Derivation of the probability/quantitative functions may be carried out by a computer. Therefore in one aspect, the invention also relates to a computational method of deriving a probability function for use in prognosing an osteoporosis phenotype or a quantitative function for estimating an osteoporosis quantitative trait which method comprises:

(a) applying multiple logistic regression analysis to outcomes data and phenotype data obtained from a population of individuals each of known clinically determined phenotype, thereby deriving a probability function which produces a statistically significant separation of individuals of different phenotype in the population; and/or
(b) applying multiple lineal regression analysis to outcomes data and quantitative trait data obtained from a population of individuals each of known quantitative trait, thereby deriving a quantitative function which produces a statistically significant estimation of the quantitative trait of individuals in the population;

wherein:
(i) the phenotype data comprises the known clinically determined phenotype of each individual;
(ii) the quantitative trait data comprises the known quantitative trait value of each individual;
(ii) the outcomes data comprises the outcomes of a set of variables for each individual in the population;

and wherein:
(a) the phenotype is suffering the fractures phenotype or vertebral fractures phenotype as described herein and the set of variables is selected from or consists of the set of fractures variables or vertebral fractures variables in Table 5;
(b) the quantitative trait is LSBMD or FNBMD and the set of variables is selected from or consists of the sets of LSBMD or FNBMD variables in Table 5;
(c) the phenotype is the WSHfractures phenotype and the set of variables is selected from or consists of the model variables for any of the models in FIG. 9.

In particular, wherein:
(i) the phenotype data comprises the known clinically determined phenotype of each individual;
(ii) the quantitative trait data comprises the known quantitative trait value of each individual;
(ii) the outcomes data comprises the outcomes of a set of variables for each individual in the population;
and wherein:
(a) the phenotype is fractures in female subjects and the set of variables is selected from or consists of the set of female fracture variables in Table 5;
(b) the phenotype is fractures in male subjects and the set of variables is selected from or consists of the set of male fracture variables in Table 5;
(c) the phenotype is vertebral fractures in female subjects and the set of variables is selected from or consists of the set of female vertebral fractures variables in Table 5;
(d) the phenotype is vertebral fractures in male subjects and the set of variables is selected from or consists of the set of male vertebral fractures variables in Table 5;
(e) the quantitative trait is lumbar spine bone mineral density (LSBMD) in female subjects and the set of variables is selected from or consists of the set of LSBMD female variables in Table 5;
(f) the quantitative trait is LSBMD in male subjects and the set of variables is selected from or consists of the set of LSBMD male variables in Table 5;
(g) the quantitative trait is femoral neck bone mineral density (FNBMD) in female subjects and the set of variables is selected from or consists of the set of FNBMD female variables in Table 5;
(f) the quantitative trait is FNBMD in male subjects and the set of variables is selected from or consists of the set of FNBMD male variables in Table 5;
(g) the phenotype is WSHfractures in female subjects and the set of variables is selected from or consists of the set of female FSTEP model variables in FIG. 9;
(h) the phenotype is WSHfractures in female subjects and the set of variables is selected from or consists of the set of female BSTEP model variables in FIG. 9;
(i) the phenotype is WSHfractures in male subjects and the set of variables is selected from or consists of the set of male FSTEP model variables in FIG. 9;
(j) the phenotype is WSHfractures in male subjects and the set of variables is selected from or consists of the set of male BSTEP model variables in FIG. 9;
(k) the phenotype is WSHfractures in a male or female subject and the set of variables is selected from or consists of the set of general FSTEP model variables in FIG. 9; and/or
(l) the phenotype is WSHfractures in a male or female subject and the set of variables is selected from or consists of the set of general BSTEP model variables in FIG. 9.

In the derivation methods for each phenotype the variables to be tested may be selected from the informative variables in Table 5 or FIG. 9 for that phenotype or quantitative trait or model as already described herein in relation to the diagnostic methods. Preferably all of the variables listed as informative for the phenotype or quantitative trait or listed for inclusion in a model in FIG. 9 are tested.

The invention also relates to the probability functions/quantitative functions so derived and to their use in diagnostic and prognostic methods described herein.

Data for calculation of probability functions for predicting the WSHfracture phenotype according to each of the models in FIG. 9 is provided in FIGS. 17-19. Statistical analyses may be performed, for example, using the Statistical Package for the Social Sciences (SPSS Inc. Headquarters, Chicago, Ill., USA) version 14.0. These may be used for calculation of probability function values for use in the methods herein. The data in the Tables may be used to construct probability functions for use in the invention.

In one aspect the invention relates to probability functions constructed or derived using the data in any of FIG. 17-19, and to their use in a method, e.g. a computational method, for prognosing WSHfractures phenotype. The invention further relates to associated computer programs and computer systems as described herein. The invention also relates to the probability functions derived according to the present methods and to their use in the methods described herein.

The process of calculating a probability function value from test outcomes data and comparing the value to values obtained from a study population of known phenotypes in order to evaluate the risk of developing a phenotype in a test individual may also be carried out using appropriate software. The process of calculating a quantitative function value from test outcomes data may also be carried out using appropriate software.

Therefore in one aspect the invention relates to a computational method for prognosing an osteoporosis phenotype (fractures or vertebral fractures or WSHfractures) using the outcomes of variables ("outcomes data") informative for that phenotype obtained according to the methods described herein. In the computational method, test outcomes data for the informative variables for a particular phenotype is inputted in a suitable probability function to produce a probability function value for the test individual. The test probability function value is then compared with probability function values for individuals of known phenotype in order to diagnose or prognose the phenotype of the test individual.

In one aspect the invention relates to a computational method for estimating an osteoporosis quantitative trait (LSBMD or FNBMD) using the outcomes of variables ("outcomes data") informative for that quantitative trait obtained according to the methods described herein. In the computational method, test outcomes data for the informative variables for a particular quantitative trait is inputted in a suitable quantitative function to produce a quantitative function value for the test individual.

The invention further relates to a computer system comprising a processor and means for controlling the processor to carry out a computational method described herein, and to a computer program comprising computer program code which when run on a computer or computer network causes the computer or computer network to carry out the computational method. In one aspect, the computer program is stored on a computer readable medium.

In general the present methods are carried out ex vivo or in vitro, e.g. using a sample obtained from the individual. A method may comprise use of the outcomes of clinical variables which have been obtained by the methods described herein.

In the present methods, the genotype of a subject with respect to a given genetic variation (such as an SNP variable) may be determined by, any suitable means. For example, genotype may be determined by microarray analysis, sequencing, primer extension, ligation of allele specific oligonucleotides, mass determination of primer extension products, restriction length polymorphism analysis, single strand conformational polymorphism analysis, pyrosequencing, dHPLC or denaturing gradient gel electrophoresis (DGGE). Furthermore, having sequenced nucleic acid of an individual or sample, the sequence information can be retained and subsequently searched without recourse to the original nucleic acid itself. Thus, for example, a sequence alteration or mutation may be identified by scanning a database of sequence information using a computer or other electronic means.

In general, a sample is provided (having been obtained from the subject), containing nucleic acid which comprises at least one of the genetic variations to be tested. The nucleic acid comprises one or more target regions comprising the genetic variation(s) (SNPs) which are to be characterised.

The nucleic acid may be obtained from any appropriate biological sample which contains nucleic acid. The sample may be taken from a fluid or tissue, secretion, cell or cell line derived from the human body.

For example, samples may be taken from blood, including serum, lymphocytes, lymphoblastoid cells, fibroblasts, platelets, mononuclear cells or other blood cells, from saliva, liver, kidney, pancreas or heart, urine or from any other tissue, fluid, cell or cell line derived from the human body. For example, a suitable sample may be a sample of cells from the buccal cavity. Preferably nucleic acid is obtained from a blood sample.

In general, nucleic acid is extracted from the biological sample using conventional techniques. The nucleic acid to be extracted from the biological sample may be DNA, or RNA, typically total RNA. Typically RNA is extracted if the genetic variation to be studied is situated in the coding sequence of a gene. Where RNA is extracted from the biological sample, the methods may further comprise a step of obtaining cDNA from the RNA. This may be carried out using conventional methods, such as reverse transcription using suitable primers. Subsequent procedures are then typically carried out on the extracted DNA or the cDNA obtained from extracted RNA. The term DNA, as used herein, may include both DNA and cDNA.

In general the genetic variations to be tested are known and characterised, e.g. in terms of sequence. Therefore nucleic acid regions comprising the genetic variations may be obtained using methods known in the art.

In general, nucleic acid regions which contain the SNPs to be identified (target regions) are subjected to an amplification reaction. Any suitable technique or method may be used for amplification. In general, where multiple SNPs are to be analysed, it is preferable to simultaneously amplify all of the corresponding target regions (comprising the variations).

For example, the polymerase chain reaction (PCR) (reviewed for instance in "PCR protocols; A Guide to Methods and Applications", Eds. Innis et al, 1990, Academic Press, New York, Mullis et al, Cold Spring Harbor Symp. Quant. Biol., 51:263, (1987), Ehrlich (ed), PCR technology, Stockton Press, NY, 1989, and Ehrlich et al, Science, 252:1643-1650, (1991)) may be used. The nucleic acid used as template in the amplification reaction may be genomic DNA, cDNA or RNA.

Other specific nucleic acid amplification techniques include strand displacement activation, the QB replicase system, the repair chain reaction, the ligase chain reaction, rolling circle amplification and ligation activated transcription.

Multiplex PCR may be carried out, using appropriate pairs of oligonucleotide PCR primers. Any suitable pair of primers which allow specific amplification of a target region may be used. In one aspect, the primers allow amplification in the fewest possible number of PCR reactions.

PCR primers suitable for amplification of target DNA regions comprising the SNPs in Table 1A/1B, Table 5 and FIG. 9 are listed in Tables 3A, B, and C. The present methods may comprise the use of one or more of these primers or one or more of the listed primer pairs. In one aspect the method comprises use of all of the primers listed in FIG. 3A or 3C.

Suitable reaction conditions may be determined using the guidance in the present Examples and the knowledge in the art.

The amplified nucleic acid may then be sequenced and/or tested in any other way to determine the presence or absence of a particular feature. Nucleic acid for testing may be prepared from nucleic acid removed from cells or in a library using a variety of other techniques such as restriction enzyme digest and electrophoresis.

For example, the allele of the at least one polymorphism (i.e. the identity of the nucleotide at the position of single nucleotide polymorphism) may be determined by determining the binding of an oligonucleotide probe to the amplified region of the genomic sample. A suitable oligonucleotide probe comprises a nucleotide sequence which binds specifically to a particular allele of the at least one polymorphism and does not bind specifically to other alleles of the at least one polymorphism. Such a probe may correspond in sequence to a region of genomic nucleic acid, or its complement, which contains one or more of the SNPs described herein. Under suitably stringent conditions, specific hybridisation of such a probe to test nucleic acid is indicative of the presence of the sequence alteration in the test nucleic acid. For efficient screening purposes, more than one probe may be used on the same test sample.

Those skilled in the art are well able to employ suitable conditions of the desired stringency for selective hybridisation, taking into account factors such as oligonucleotide length and base composition, temperature and so on.

Suitable selective hybridisation conditions for oligonucleotides of 17 to 30 bases include hybridization overnight at 42° C. in 6×SSC and washing in 6×SSC at a series of increasing temperatures from 42° C. to 65° C.

Other suitable conditions and protocols are described in Molecular Cloning: a Laboratory Manual: $2^{nd}$ edition, Sambrook et al., 1989, Cold Spring Harbor Laboratory Press and Current Protocols in Molecular Biology, Ausubel et al. eds., John Wiley & Sons, 1992.

A further aspect of the present invention provides an oligonucleotide which hybridises specifically to a nucleic acid sequence which comprises a particular allele of a polymorphism selected from the group consisting of the single nucleotide polymorphisms shown in Table 1A/1B, Table 5 and FIG. 9, and does not bind specifically to other alleles of the SNP. Hybridisation may be determined under suitable selective hybridisation conditions as described herein.

Such oligonucleotides may be used in a method of screening nucleic acid.

In some preferred embodiments, oligonucleotides according to the present invention are at least about 10 nucleotides in length, more preferably at least about 15 nucleotides in length, more preferably at least about 20 nucleotides in length. Oligonucleotides may be up to about 100 nucleotides in length, more preferably up to about 50 nucleotides in length, more preferably up to about 30 nucleotides in length. The boundary value 'about X nucleotides' as used above includes the boundary value 'X nucleotides'. Oligonucleotides which specifically hybridise to particular alleles of the SNPs listed in Table 1A/1B, Table 5 and FIG. 9, are listed in Table 2A, B and C and are described herein.

Where the nucleic acid is double-stranded DNA, hybridisation will generally be preceded by denaturation to produce single-stranded DNA. The hybridisation may be as part of an amplification, e.g. PCR procedure, or as part of a probing procedure not involving amplification. An example procedure would be a combination of PCR and low stringency hybridisation. A screening procedure, chosen from the many available to those skilled in the art, is used to identify successful hybridisation events and isolated hybridised nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RN'ase cleavage and allele specific oligonucleotide probing. Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mismatch between two annealing nucleic acid molecules.

For instance, RN'ase A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid.

Nucleic acid in a test sample, which may be a genomic sample or an amplified region thereof, may be sequenced to identify or determine the identity of a polymorphic allele. The allele of the SNP in the test nucleic acid can therefore be compared with the susceptibility alleles of the SNP as described herein to determine whether the test nucleic acid contains one or more alleles which are associated with disease.

Typically in sequencing, primers complementary to the target sequence are designed so that they are a suitable distance (e.g. 50-400 nucleotides) from the polymorphism. Sequencing is then carried out using conventional techniques. For example, primers may be designed using software that aims to select sequence(s) within an appropriate window which have suitable Tm values and do not possess secondary structure or that will hybridise to non-target sequence.

Sequencing of an amplified product may involve precipitation with isopropanol, resuspension and sequencing using a TaqFS+ Dye terminator sequencing kit. Extension products may be electrophoresed on an ABI 377 DNA sequencer and data analysed using Sequence Navigator software.

Genotype analysis may be carried out by microarray analysis. Any suitable microarray technology may be used. The methodology reported in Tejedor et al 2005 (Clinical Chemistry 51: 1137-1144), including the MG 1.0 software and in International Patent Application No. PCT/IB2006/00796 filed 12 Jan. 2006 (the contents of which are hereby incorporated by reference) may be used. This technology uses a low-density DNA array and hybridisation to allele-specific oligonucleotide probes to screen for SNPs. Thus in one aspect the Osteochip microarray and the microarray methods and technology of the present invention described herein may be used to determine the genotype of the informative SNPs as described herein.

In one aspect the present invention relates to a microarray adapted for use in the present methods as described herein.

The present methods may be used to diagnose or prognose the probability of a given osteoporosis phenotype such as fractures or vertebral fractures or WSHfractures in a subject, or to estimate an osteoporosis quantitative trait (LSBMD or FNBMD) in a subject.

Once a subject has received an estimation of low LSBMD and/or FNBMD or a prognosis of developing fractures and/or vertebral fractures and/or WSHfractures, the most appropriate recommendations and/or treatment for that subject can be selected. In this way, the invention allows better targeting of therapies to patients.

A comprehensive osteoporosis treatment program includes a focus on proper nutrition, exercise, and safety issues to prevent falls that may result in fractures. In addition, there are therapeutic medications to slow or stop bone loss, increase bone density, and reduce fracture risk. Currently treatments for osteoporosis include alendronate, raloxifene, risedronate, and ibandronate and they are approved by the U.S. Food and Drug Administration (FDA) for preventing and treating postmenopausal osteoporosis. Teriparatide is approved for treating the disease in postmenopausal women and men at high risk for fracture. Estrogen/hormone therapy (ET/HT) is approved for preventing postmenopausal osteoporosis, and calcitonin is approved for treatment. In addition, alendronate is approved for treating osteoporosis in men, and both alendronate and risedronate are approved for use by men and women with glucocorticoid-induced osteoporosis.

Thus in a further aspect, the invention provides a method of selecting a suitable treatment for osteoporosis or its prevention in a subject, the method comprising:
(a) prognosing an osteoporosis phenotype (fractures or vertebral fractures or WSHfractures) in the subject and/or estimating an osteoporosis quantitative trait (LSBMD and/or FNBMD) in the subject by a method described herein; and
(b) selecting a treatment which is suitable for the determined phenotype(s) or trait(s).

The selected treatment may then be administered to the subject. Thus the invention also relates to a method of treating osteoporosis in a subject comprising:
(a) prognosing an osteoporosis phenotype (fractures or vertebral fractures or WSHfractures, e.g determining fractures risk) in the subject and/or estimating an osteoporosis quantitative trait (LSBMD and/or FNBMD) in the subject by a method described herein; and
(b) treating the subject with a treatment suitable for the determined phenotype and/or trait.

For example, the present methods may be used to predict the apparition of fractures and/or vertebral fractures and/or WSHfractures and to estimate low values of LSBMD and/or FNBMD with the age.

If an individual is predicted to be at significant risk of developing fractures, especially WSHfractures, and significantly low BMD, the individual may be selected for a more aggressive treatment.

Means for carrying out the present methods may be provided in kit form. Therefore in one aspect the invention further relates to diagnostic kits suitable for use in the methods described herein. Typically a kit comprises:
(i) means for determining outcomes for the selected (SNP) variables; and
(ii) instructions for determining risk of fractures and/or vertebral fractures and/or WSHfractures and estimating LSBMD and FNBMD and probable disease course based on the outcomes.

The means (i) may comprise oligonucleotide probes suitable for detection of one or more SNP variables to be determined. For example, the means (i) may comprise one or more probe pairs or probe sets listed in FIG. 2A, B or C. In one instance the kit may comprise all of the probe sets in FIG. 2A or 2C.

The means (i) may comprise a suitable microarray as described herein. The means (i) may comprise one or more pairs of sequencing primers suitable for sequencing one or more of the SNP variables to be determined.

The instructions (ii) typically comprise instructions to use the outcomes determined using the means (i) for the prediction of fractures and/or vertebral fractures and/or WSHfractures and estimating LSBMD and/or FNBMD. The instructions may comprise a chart showing risks of particular disease course occurring.

A kit may in some cases include a computer program as described herein.

A kit may include other components suitable for use in the present methods. For example, a kit may include primers suitable for amplification of target DNA regions containing the SNPs to be determined, such as those described herein. A kit may also include suitable labelling and detection means, controls and/or other reagents such as buffers, nucleotides or enzymes e.g. polymerase, nuclease, transferase.

Nucleic acid according to the present invention, such as an oligonucleotide probe and/or pair of amplification primers, may be provided as part of a kit. The kit may include instructions for use of the nucleic acid, e.g. in PCR and/or a method for determining the presence of nucleic acid of interest in a test sample. A kit wherein the nucleic acid is intended for use in PCR may include one or more other reagents required for the reaction, such as polymerase, nucleosides, buffer solution etc. The nucleic acid may be labelled.

A kit for use in determining the presence or absence of nucleic acid of interest may include one or more articles and/or reagents for performance of the method, such as means for providing the test sample itself, e.g. a swab for removing cells from the buccal cavity or a syringe for removing a blood sample (such components generally being sterile).

In a further aspect the present invention also relates to DNA chips or microarrays and methods for their use, which allow reliable genotyping of individuals with respect to multiple osteoporosis associated genetic variations simultaneously and for clinical purposes.

Thus in one aspect, the invention further provides a method of genotyping Osteoporosis associated genetic variations in an individual, which is sufficiently sensitive, specific and reproducible for clinical use. The inventors have developed low density DNA-microarrays with specifically designed probes for use in the method, and a computational method or algorithm for interpreting and processing the data generated by the arrays.

In one aspect, the invention relates to an in vitro method for genotyping osteoporosis associated genetic variations in an individual. The method allows simultaneous genotyping of multiple human genetic variations present in one or more genes of a subject. The method of the invention allows identification of nucleotide changes, such as, insertions, duplications and deletions and the determination of the genotype of a subject for a given genetic variation.

Genetic variation or genetic variant refers to mutations, polymorphisms or allelic variants. A variation or genetic variant is found amongst individuals within the population and amongst populations within the species.

An osteoporosis associated genetic variation may refer to a genetic variation that is associated with osteoporosis in a statistically significant way and that can be used as an aid in the diagnosis, prognosis or prediction of response to therapy in an individual.

Polymorphism refers to a variation in the sequence of nucleotides of nucleic acid where every possible sequence is present in a proportion of equal to or greater than 1% of a population; in a particular case, when the said variation occurs in just one nucleotide (A, C, T or G) it is called a single nucleotide polymorphism (SNP).

Genetic mutation refers to a variation in the sequence of nucleotides in a nucleic acid where every possible sequence is present in less than 1% of a population.

Allelic variant or allele refers to a polymorphism that appears in the same locus in the same population.

Thus a genetic variation may comprise a deletion, substitution or insertion of one or more nucleotides. In one aspect the genetic variations to be genotyped according to the present methods comprise SNPs.

A given gene may comprise one or more genetic variations. Thus the present methods may be used for genotyping of one or more genetic variations in one or more genes.

Typically the individual is a human.

Typically, for a given genetic variation there are three possible genotypes:
AA the individual is homozygous for genetic variation A (e.g. homozygous for a wild type allele)
BB the individual is homozygous for genetic variation B (e.g. homozygous for a mutant allele)
AB the individual is heterozygous for genetic variations A and B (e.g. one wild type and one mutant allele)

The genetic variations, such as SNPs, to be analysed according to the present methods, are associated with osteoporosis. Examples of genetic variations associated with osteoporosis which may be assessed by the present methods include those in Table 1A/1B (FIG. 1).

The sequences of all the genes mentioned in Table 1A are known and recognized on the following websites: GeneBank (NCBI), GeneCard (Weizmann Institute of Sciences) and Snpper.chip.org (Innate Immunity PGA). RefSNP codes (rs#) for each SNP in Table 1B are taken from the Single Nucleotide Polymorphism Database (dbSNP) curated by the National Center for Biotechnology Information (NCBI) (available on the World Wide Web at www.ncbi.nlm.nih.qov/entrez/query.fcqi?CMD=search&DB=snp, as at 6 Jul. 2007).

By permitting clinical genotyping of one or more of the above genetic variations, the present method has use in for example, diagnosing susceptibility to or the presence of osteoporosis in a subject. The present genotyping methods are also be useful in prognosing osteoporosis phenotypes, as described herein.

At least one osteoporosis associated genetic variation, e.g. SNP, is analysed in the present genotyping methods. The present methods allow simultaneous genotyping of multiple variations in an individual and typically multiple variations are analysed, in general, at least 10, 12, 14, 16, 18 or 20 Osteoporosis associated genetic variations. For example, at least 25, 30, 35, 40, 45, 50, 55, 60, 65, 70, 75, 80, 85, 90, 95, 100, 105 or 110 variations or up to 150, 200, 300, 400, 500, or 600 variations may be tested, such as 250, 350 or 450 variations.

Thus the genotyping methods may be used for genotyping an individual with respect to all of or a selection of the variations in Table 1A/1B, as described herein. For example, at least 1, 2, 3, 4, 5, 10, 15, 20, 25, 30, 35, 40, 45, 50, 55, 60, 65, 70, 75, 80, 85, 90, 95, 100, 105, 110 or all of the Table 1A/1B variations may be genotyped. The variations to be detected may additionally include other osteoporosis associated genetic variations.

The present invention also encompasses methods in which other genetic variations are assessed in addition to the osteoporosis associated genetic variations.

According to the present methods, a sample is provided, containing nucleic acid which comprises at least one of the genetic variations to be tested (the target DNA). Suitable samples and methods for obtaining the samples are described herein in relation to the prognostic methods.

As described, DNA regions which contain the genetic variations to be identified (target DNA regions) may be subjected to an amplification reaction in order to obtain amplification products which contain the genetic variations to be identified. Any suitable technique or method may be used for amplification. In general, the technique allows the (simultaneous) amplification of all the DNA sequences containing the genetic variations to be identified. In other words, where multiple genetic variations are to be analysed, it is preferable to simultaneously amplify all of the corresponding target DNA regions (comprising the variations). Carrying out the amplification in a single step (or as few steps as possible) simplifies the method.

For example, multiplex PCR may be carried out, using appropriate pairs of oligonucleotide PCR primers which are capable of amplifying the target regions containing the genetic variations to be identified. Any suitable pair of primers which allow specific amplification of a target DNA region may be used. In one aspect, the primers allow amplification in the least possible number of PCR reactions. Thus, by using appropriate pairs of oligonucleotide primers and appropriate conditions, all of the target DNA regions necessary for genotyping the genetic variations can be amplified for genotyping (e.g. DNA-chip) analysis with the minimum number of reactions. Suitable PCR primers for amplification of target DNA regions comprising the osteoporosis-associated genetic variations in Table 1A/1B are listed in Tables 3A, 3B and 3C. The present method may comprise the use of one or more of these primers or one or more of the listed primer pairs. For example, the present methods may be used for genotyping of Table 1A/1B variations selected as described above. The corresponding primers in Table 3A, 3B or 3C may be selected for use accordingly.

In one instance, the amplification products can be labelled during the amplification reaction with a detectable label. The aim is to be able to later detect hybridisation between the fragments of target DNA containing the genetic variations being analysed and probes fixed on a solid support. The greater the extent of hybridisation of labelled target DNA to a probe, the greater the intensity of detectable label at that probe position.

The amplification products may be labelled by conventional methods. For example, a labelled nucleotide may be incorporated during the amplification reaction or labelled primers may be used for amplification.

Labelling may be direct using for example, fluorescent or radioactive markers or any other marker known by persons skilled in the art. Examples of fluorophores which can be used, include for example, Cy3 or Cy5. Alternatively enzymes may be used for sample labelling, for example alkaline phosphatase or peroxidase. Examples of radioactive isotopes which can be used include for example $^{33}P$, $^{125}I$, or any other marker known by persons skilled in the art. In one instance, labelling of amplification products is carried out using a nucleotide which has been labelled directly or indirectly with one or more fluorophores. In another example, labelling of amplification products is carried out using primers labelled directly or indirectly with one or more fluorophores.

Labelling may also be indirect, using, for example, chemical or enzymatic methods. For example, an amplification product may incorporate one member of a specific binding pair, for example avidin or streptavidin, conjugated with a fluorescent marker and the probe to which it will hybridise may be joined to the other member of the specific binding pair, for example biotin (indicator), allowing the probe/target binding signal to be measured by fluorimetry. In another example, an amplification product may incorporate one member of a specific binding pair, for example, an anti-dioxigenin antibody combined with an enzyme (marker) and the probe to which it will hybridise may be joined to the other member of the specific binding pair, for example dioxigenin (indicator). On hybridization of amplification product to probe the enzyme substrate is converted into a luminous or fluorescent product and the signal can be read by, for example, chemiluminescence or fluorometry.

The nucleic acid comprising the genetic variation(s) to be tested, e.g. the (optionally labelled) amplification products, may further undergo a fragmentation reaction, thereby obtaining some fragmentation products which comprise or contain the genetic variations to be identified or analysed. Typically fragmentation increases the efficiency of the hybridisation reaction. Fragmentation may be carried out by any suitable method known in the art, for example, by contacting the nucleic acid, e.g. the amplification products with a suitable enzyme such as a DNase.

If the nucleic acid has not been previously labelled, e.g. during the amplification reaction, (and, typically, where no posthybridisation amplification or ligation is carried out on the solid support) then labelling with a detectable label may be carried out prehybridisation by labelling the fragmentation products. Suitable labelling techniques are known in the art and may be direct or indirect as described herein. Direct labelling may comprise the use of, for example, fluorophores, enzymes or radioactive isotopes. Indirect labelling may comprise the use of, for example, specific binding pairs that incorporate e.g. fluorophores, enzymes, etc. For example, if amplification products have not been labelled during the amplification reaction the fragmentation products may undergo a direct or indirect labelling with one or various markers, for example one or various fluorophores, although other known markers can be used by those skilled in the art.

According to the present methods the nucleic acid, e.g. the amplification or fragmentation products, comprising the genetic variation(s) to be detected (target DNA), is contacted with oligonucleotide probes which are capable of detecting the corresponding genetic variations by hybridisation under suitable conditions.

Typically the hybridisation conditions allow specific hybridisation between probes and corresponding target nucleic acids to form specific probe/target hybridisation complexes while minimising hybridisation between probes carrying one or more mismatches to the DNA. Such conditions may be determined empirically, for example by varying the time and/or temperature of hybridisation and/or the number and stringency of the array washing steps that are performed following hybridisation and are designed to eliminate all probe-DNA interactions that are inspecific. In the method, the probes are provided deposited on a solid support or surface. The probes are deposited at positions on the solid support according to a predetermined pattern, forming a "DNA-chip". It has been found that the chips should comply with a number of requirements in order to be used in the present methods, for example in terms of the design of the probes, the number of probes provided for each genetic variation to be detected and the distribution of probes on the support. These are described in detail herein. The inventors have developed suitable genotyping chips for use in the present methods and accordingly in one aspect the invention provides a DNA-chip or (micro)array comprising a plurality of probes deposited or immobilised on a solid support as described herein.

In general the solid support or phase comprises oligonucleotide probes suitable for detection of each genetic variation to be tested in the present method. The number and type of genetic variations to be tested using a chip may be selected as described herein.

Typically there will be at least one probe which is capable of hybridising specifically to genetic variation A (e.g. a wildtype or normal allele) (probe 1) and one probe which is capable of hybridising specifically to genetic variation B (e.g. a mutant allele) (probe 2) under the selected hybridisation conditions. These probes form a probe pair. Probe 1 is for detection of genetic variation A and probe 2 for detection of genetic variation B. Typically the probes can be used to discriminate between A and B (e.g. the wildtype and mutant alleles).

The probes may examine either the sense or the antisense strand. Typically, probes 1 and 2 examine the same nucleic acid strand (e.g. the sense strand or antisense strand) although in some cases the probes may examine different strands. In one aspect probes 1 and 2 have the same sequence except for the site of the genetic variation.

In one instance, the probes in a probe pair have the same length. In some aspects, where two or more pairs of probes are provided for analysis of a genetic variation, the probes may all have the same length.

Preferably more than one probe pair is provided for detection of each genetic variation. Thus, at least 2, 3, 4, 5, 6, 7, 8, 9, 10 or more probe pairs may be provided per genetic variation. In one aspect, (at least) 2 probe pairs are provided. The aim is to reduce the rate of false positives and negatives in the present methods.

For example, for a given genetic variation there may be:
Probe 1 which is capable of hybridising to genetic variation A (e.g. a normal allele)
Probe 2 which is capable of hybridising to genetic variation B (e.g. a mutant allele)
Probe 3 which is capable of hybridising to genetic variation A (e.g. a normal allele)
Probe 4 which is capable of hybridising to genetic variation B (e.g. a mutant allele).

The probes may examine the same or different strands. Thus in one embodiment, probes 3 and 4 are the complementary probes of probes 1 and 2 respectively and are designed to examine the complementary strand. In one aspect it is preferred that the probes provided for detection of each genetic variation examine both strands.

More than 2 pairs of probes may be provided for analysis of a genetic variation as above. For example, where a genetic variation exists as any one of 4 bases in the same strand (e.g. there are three mutant possibilities), at least one pair of probes may be provided to detect each possibility. Preferably, at least 2 pairs of probes are provided for each possibility.

Thus, for example, for an SNP G2677T/A/C, at least one pair of probes may be provided for detection of G2677T, one pair for detection of G2677/A, and one pair for detection of G2677C. Preferably at least two pairs of probes are provided for each of these substitutions.

A number of methods are known in the art for designing oligonucleotide probes suitable for use in DNA-chips.

A "standard tiling" method may be used. In this method, 4 oligonucleotides are designed that are totally complementary to the reference sequence except in the central position where, typically the 4 possible nucleotides A, C, G and T are examined. An illustrative example of this strategy is the DNA-chip for genotyping of HIV-1 (Affymetrix).

In "alternative tiling" 5 oligonucleotides are designed, so that the fifth examines a possible deletion in the sequence. An example of this strategy is the DNA-chip to detect mutations in p53 (Affymetrix).

In "block tiling" 4 oligonucleotides are designed that are totally complementary to the normal sequence and another 4 totally complementary to the mutant sequence. The nucleotide which changes is placed in the central position, but a mismatch of one of the 4 bases (A, C, T or G) is placed 2 nucleotides before or after the nucleotide position that it is wished to interrogate. An example of this strategy is the DNA-chip for the detection of mutations in cytochrome p450 (Roche and Affymetrix).

A further example is "alternative block tiling" where the "mismatch" is used to increase the specificity of the hybrid not only in one position but also in the positions −4, −1, 0, +1 and +4 to identify the change produced in the central position or 0. An example is the DNA-chip to detect 1,500 SNPs (Affymetrix).

Any one or more of these strategies may be used to design probes for the present invention. Preferably standard tiling is used, in particular with 2 pairs of probes e.g. 2 pairs of complementary probes as above. Thus it is preferable that the oligonucleotide sequence is complementary to the target DNA or sequence in the regions flanking the variable nucleotide(s). However, in some cases, one or more mismatches may be introduced, as described above.

The oligonucleotide probes for use in the present invention typically present the base to be examined (the site of the genetic variation) at the centre of the oligonucleotide. This is particularly the case where differential hybridisation methods are used, as in general this allows the best discrimination between matched and mismatched probes. In these methods, typically there is formation of specific detectable hybridisation complexes without post-hybridisation on-chip amplification. For example, for precise (single base) mutations, the base which differs between the normal and the mutant allele is typically placed in the central position of the probe. In the case of insertions, deletions and duplications, the first nucleotide which differs between the normal and the mutant sequence is placed in the central position. It is believed that placing the mutation at the centre of the probe maximises specificity.

Where post-hybridisation on-chip amplification (e.g. ligation or primer extension methods) is employed, oligonucleotide probes typically present the variable base(s) at the 3' end of the probe. Where OLA methodology is used, oligonucleotides (labelled directly or indirectly) are also designed which hybridise to probe-target complexes to allow ligation.

In general the probes for use in the present invention comprise or in some embodiments consist (essentially) of 17 to 27 nucleotides, for example, 19, 21, 23, or 25 nucleotides or 18, 20, 22, 24 or 26 nucleotides.

Preferably the individual probes provided for detection of a genetic variation are capable of hybridising specifically to the normal and mutant alleles respectively under the selected hybridisation conditions. For example, the melting temperature of the probe/target complexes may occur at 75-85° C. and hybridisation may be for one hour, although higher and lower temperatures and longer or shorter hybridisations may also suffice.

The probes provided for (suitable for) detection of each genetic variation (as described above) are typically capable of discriminating between genetic variation A and B (e.g. the normal and mutant alleles) under the given hybridisation conditions as above. Preferably the discrimination capacity of the probes is substantially 100%. If the discrimination capacity is not 100%, the probes are preferably redesigned. Preferably the melting temperature of the probe/target complexes occurs at 75-85 degrees C. Methods for testing discrimination capacity are described herein.

In one example, the probes provided for detection of a genetic variation examine both strands and have lengths ranging from 19-27 nucleotides. Preferably the probes have 100% discrimination capacity and the melting temperature of probe/target complexes is 75-85 degrees C.

Typically in order to obtain probes for use in the present methods, a number of probes are designed and tested experimentally for, e.g. hybridisation specificity and ability to discriminate between genetic variants (e.g. a normal and a mutant allele). Candidate oligonucleotide probe sequences may be designed as described above. These may vary for example in length, strand specificity, position of the genetic variation and degree of complementarity to the sequence flanking the genetic variation in the target DNA. Once probe pairs have been designed, these can be tested for hybridisation specificity and discrimination capacity. The capacity of specific probes to discriminate between the genetic variations A and B (e.g. normal and mutant alleles) depends on hybridisation conditions, the sequence flanking the mutation and the secondary structure of the sequence in the region of the mutation. By using stable hybridisation conditions, appropriate parameters such as strand specificities and lengths can be established in order to maximise discrimination. Preferably, the genetic variation is maintained at the central position in the tested probes.

Methods for testing discrimination capacity of probes are described herein. Typically a number of candidate probe pairs are provided and used in a training method as described below. In general two pairs of probes (probes 1 and 2, and probes 3 and 4) are tested in the method. For example, two pairs of probes examining both strands (complementary to each other) may be tested. If it is not possible to obtain 100% discrimination between the three genotyping groups using the probes, the probes are typically redesigned. Hybridisation conditions in the training method are generally maintained stably. Typically the melting temperature of probe/target complexes is 75-85° C.

For example, starting from probes of 25 nucleotides which detect a genetic variation (e.g. the normal allele) and another genetic variation (e.g. a mutant allele) in both strands (sense and antisense), in general an average of 8 probes may be experimentally tested to identify two definite pairs.

Probes are chosen to have maximum hybridisation specificity and discrimination capacity between genetic variants (e.g. a normal and a mutant allele) under suitable hybridisation conditions. For example, the probes for detection of a given genetic variation, e.g. two probe pairs, typically have substantially 100% discrimination capacity. Typically the melting temperature of probe/target complexes is at 75-85° C.

Using the methods herein the inventors have developed oligonucleotide probes suitable for detection of the osteoporosis-associated genetic variations in Table 1A/1B. These probes are presented in Tables 2A, 2B and 2C. The probes are listed in probe sets, according to the genetic variation to be detected. At least two pairs of probes are listed in each set.

In one aspect the invention relates to any one or more of the oligonucleotide probes, pairs of probes or sets of probes set out in Table 2A, 2B or 2C, and to their use in the genotyping, diagnostic or therapeutic methods of the invention. The invention further relates to any one or more of the oligonucleotide probes, pairs of probes or sets of probes set out in Table 2A, 2B or 2C for use in medicine, for example in a diagnostic or therapeutic method described herein. A chip of the invention may comprise one or more of the listed probe pairs or sets as described herein.

In general probes are provided on the support in replicate. Typically, at least 4, 6, 8, 10, 12, 14, 16, 18 or 20 replicates are provided of each probe, in particular, 6, 8 or 10 replicates. Thus for example, the support (or DNA-chip) may comprise or include 10 replicates for each of (at least) 4 probes used to detect each genetic variation (i.e. 40 probes). Alternatively the support (or DNA-chip) may comprise or include 8 replicates for each of (at least) 4 probes used to detect each genetic variation (i.e. 32 probes). Still further the support (or DNA-chip) may comprise or include 6 replicates for each of (at least) 4 probes used to detect each genetic variation (i.e. 24 probes). Using probe replicates helps to minimise distortions in data interpretation from the chip and improves reliability of the methods.

In general the support also comprises one or more control oligonucleotide probes. These are also provided in replicate as above. Thus the support (or DNA-chip) may additionally comprise one or more oligonucleotides deposited on the support which are useful as positive and/or negative controls of the hybridisation reactions. If post-hybridisation amplification or ligation reactions are carried out on the chip, there may also be one or more positive or negative controls of these reactions.

Typically the chip or array will include positive control probes, e.g., probes known to be complementary and hybridisable to sequences in the target polynucleotide molecules, probes known to hybridise to an external control DNA, and negative control probes, e.g., probes known to not be complementary and hybridizable to sequences in the target polynucleotide molecules. The chip may have one or more controls specific for each target, for example, 2, 3, or more controls. There may also be at least one control for the array.

Positive controls may for example be synthesized along the perimeter of the array or in diagonal stripes across the array. The reverse complement for each probe may be synthesized next to the position of the probe to serve as a negative control. In yet another example, sequences from other species of organism may be used as negative controls in order to help determine background (non-specific) hybridisation.

As above, the support (or DNA-chip) may include some (one or more) oligonucleotides deposited on the support which are useful as positive and negative controls of the hybridization reactions. In general, each one of the sub-arrays, for example 16, which typically constitute a DNA-chip, is flanked by some external hybridization controls, which serve as reference points allowing allow the points within the grid to be located more easily.

In one instance, the nucleotide sequence of an external control DNA is the following (5'→3'):

CEH:
(SEQ ID NO: 669)
GTCGTCAAGATGCTACCGTTCAGGAGTCGTCAAGATGCTACCGTTCAGGA and the sequences of the oligonucleotides for its detection are the following:

```
ON1:    CTTGACGACTCCTGAACGG      (SEQ ID NO: 670)

ON2:    CTTGACGACACCTGAACGG      (SEQ ID NO: 671)
```

Positive control probes are generally designed to hybridise equally to all target DNA samples and provide a reference signal intensity against which hybridisation of the target DNA (sample) to the test probes can be compared. Negative controls comprise either "blanks" where only solvent (DMSO) has been applied to the support or control oligonucleotides that have been selected to show no, or only minimal, hybridisation to the target, e.g. human, DNA (the test DNA). The intensity of any signal detected at either blank or negative control oligonucleotide features is an indication of non-specific interactions between the sample DNA and the array and is thus a measure of the background signal against which the signal from real probe-sample interactions must be discriminated.

Desirably, the number of sequences in the array will be such that where the number of nucleic acids suitable for detection of genetic variations is n, the number of positive and negative control nucleic acids is n', where n' is typically from 0.01 to 0.4n.

In general, the support or chip is suitable for genotyping osteoporosis associated genetic variations, in particular, genotyping according to the present methods. The chip typically comprises probes suitable for detection of at least one but preferably multiple, osteoporosis associated genetic variation(s), typically at least 10, 12, 14, 16, 18 or 20 variations. For example, at least 25, 30, 35, 40, 45, 50, 55, 60, 65, 70, 75, 80, 85, 90, 95, 100, 105 or 110 variations or up to 150, 200, 300, 400, 500, or 600 variations may be tested, such as 250, 350 or 450 variations.

The osteoporosis associated genetic variations may include any or all of those in Table 1A/1B. Thus an array or chip may comprise probes suitable for genotyping an individual with respect to all of the variations in Table 1A/1B, or a selection of the variations in the Table, as described herein.

A DNA-chip according to the invention ('Osteochip') allows simultaneous, sensitive, specific and reproducible genotyping of genetic variations associated with osteoporosis. Non-limiting examples of such variations are given in Table 1A/1B. Nevertheless, the number of genetic variations contained in the Table can be increased as other genetic variations are subsequently identified and are associated with osteoporosis. Thus the genetic variations detectable by the chip may comprise, or consist (essentially) of those listed in Table 1A/1B or FIG. 5 or FIG. 9 or a selection of these, as described in relation to the present diagnostic and prognostic methods. The chip will comprise probes suitable for detection of these genetic variations as described herein. Preferably where a chip comprises probes for detection of a genetic variation in Table 1A/1B the chip comprises one or more of the probes listed in Table 2A, B or C as suitable for detection of that genetic variation, e.g. the probes set listed in Table 2A, B or C for detection of that variation. In one aspect the present chip comprises one or more probes selected from those in Table 2A, 2B or 2C.

The probes are listed in probe sets, according to the genetic variation to be detected. At least two pairs of probes are provided in each set. A chip may comprise at least one probe pair or at least one probe set, or a selection of the probe sets, for example a probe pair or a probe set from at least 5, 10, 15, 20, 25, 30, 35, 40, 45, 50, 55, 60, 65, 70, 75, 80, 85, 90, 95, 100, 105, 110 or all 112 sets in Table 2A or 2C, according to the genetic variations being tested. A chip may comprise other probes for detection of variations in Table 1A/1B or other variations associated with osteoporosis instead of or in addition to those specifically listed.

Osteochip may additionally comprise oligonucleotide probes for detection of genetic variations not associated with osteoporosis. For example, the chips may comprise probes for detection of genetic variations such as SNPs associated with another (related) inflammatory condition such as osteoarthritis or psoriasis. Typically, in Osteochip, the number of nucleic acids suitable for detection of genetic variations associated with osteoporosis (e.g. those in Table 1N1B or FIG. 5 or FIG. 9) represent at least 50%, 60%, 70%, 75%, 80%, 85%, 90%, 95%, 97%, 98%, 99% or more of the nucleic acids in the array.

In general the support or chip has from 300 to 40000 nucleic acids (probes), for example, from 400 to 30000 or 400 to 20000. The chip may have from 1000 to 20000 probes, such as 1000 to 15000 or 1000 to 10000, or 1000 to 5000. A suitable chip may have from 2000 to 20000, 2000 to 10000 or 2000 to 5000 probes. For example, a chip may have 1000, 2000, 3000, 4000, 5000, 6000, 7000, 8000, 9000, 10000, 12000, 14000, 16000, 18000 or 20000 probes. Smaller chips 400 to 1000 probes, such as 400, 500, 600, 700, 800, 900 or 950 probes are also envisaged.

In general the array or chip of the invention comprises a support or surface with an ordered array of binding (e.g. hybridisation) sites or probes. Thus the arrangement of probes on the support is predetermined. Each probe (i.e. each probe replicate) is located at a known predetermined position on the solid support such that the identity (i.e. the sequence) of each probe can be determined from its position in the array. Typically the probes are uniformly distributed in a predetermined pattern.

Preferably, the probes deposited on the support, although they maintain a predetermined arrangement, are not grouped by genetic variation but have a random distribution. Typically they are also not grouped within the same genetic variation. If desired, this random distribution can be always the same. Therefore, typically the probes are deposited on the solid support (in an array) following a predetermined pattern so that they are uniformly distributed, for example, between the two areas that may constitute a DNA-chip, but not grouped according to the genetic variation to be characterised. Distributing probe replicates across the array in this way helps to reduce or eliminate any distortion of signal and data interpretation, e.g. arising from a non-uniform distribution of background noise across the array.

As explained above, probes may be arranged on the support in subarrays.

The support, on which the plurality of probes is deposited, can be any solid support to which oligonucleotides can be attached. Practically any support, to which an oligonucleotide can be joined or immobilized, and which may be used in the production of DNA-chips, can be used in the invention. For example, the said support can be of a non-porous material, for example, glass, silicone, plastic, or a porous material such as a membrane or filter (for example, nylon, nitrocellulose) or a gel. In one embodiment, the said support is a glass support, such as a glass slide.

Microarrays are in general prepared by selecting probes which comprise a given polynucleotide sequence, and then immobilizing such probes to a solid support or surface. Probes may be designed, tested and selected as described herein. In general the probes may comprise DNA sequences. In some embodiments the probes may comprise RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

Microarrays or chips can be made in a number of ways. However produced, microarrays typically share certain characteristics. The arrays are reproducible, allowing multiple copies of a given array to be produced and easily compared with each other. Preferably, microarrays are made from materials that are stable under binding (e.g., nucleic acid hybridization) conditions. The micro-arrays are preferably small, e.g., between 0.25 to 25 or 0.5 to 20 $cm^2$, such 0.5 to 20 $cm^2$ or 0.5 to 15 $cm^2$, for example, 1 to 15 $cm^2$ or 1 to 10 $cm^2$, such as 2, 4, 6 or 8 $cm^2$.

Probes may be attached to the present support using conventional techniques for immobilization of oligonucleotides on the surface of the supports. The techniques used depend, amongst other factors, on the nature of the support used [porous (membranes, micro-particles, etc.) or non-porous (glass, plastic, silicone, etc.)] In general, the probes can be immobilized on the support either by using non-covalent immobilization techniques or by using immobilization techniques based on the covalent binding of the probes to the support by chemical processes.

Preparation of non-porous supports (e.g., glass, silicone, plastic) requires, in general, either pre-treatment with reactive groups (e.g., amino, aldehyde) or covering the surface of the support with a member of a specific binding pair (e.g. avidin, streptavidin). Likewise, in general, it is advisable to pre-activate the probes to be immobilized by means of corresponding groups such as thiol, amino or biotin, in order to achieve a specific immobilization of the probes on the support.

The immobilization of the probes on the support can be carried out by conventional methods, for example, by means of techniques based on the synthesis in situ of probes on the support (e.g., photolithography, direct chemical synthesis, etc.) or by techniques based on, for example, robotic arms which deposit the corresponding pre-synthesized probe (e.g. printing without contact, printing by contact).

In one embodiment, the support is a glass slide and in this case, the probes, in the number of established replicates (for example, 6, 8 or 10) are printed on pre-treated glass slides, for example coated with aminosilanes, using equipment for automated production of DNA-chips by deposition of the oligonucleotides on the glass slides ("micro-arrayer"). Deposition is carried out under appropriate conditions, for example, by means of crosslinking with ultraviolet radiation and heating (80° C.), maintaining the humidity and controlling the temperature during the process of deposition, typically at a relative humidity of between 40-50% and typically at a temperature of 20° C.

The replicate probes are distributed uniformly amongst the areas or sectors (sub-arrays), which typically constitute a DNA-chip. The number of replicas and their uniform distribution across the DNA-chip minimizes the variability arising from the printing process that can affect experimental results. Likewise, positive and negative hybridisation controls (as described herein) may be printed. To control the quality of the manufacturing process of the DNA-chip, in terms of hybridization signal, background noise, specificity, sensitivity and reproducibility of each replica as well as differences caused by variations in the morphology of the spotted probe features after printing, a commercial DNA can be used. For example, as a quality control of the printing of the DNA-chips, hybridization may be carried out with a commercial DNA (e.g. k562 DNA High Molecular Weight, Promega)

In the first place, the morphology and size of the printed spots are analyzed. In the hybridization with control DNA the parameters described below for determining reliability of genotype determination, are adhered to; specifically the relationship between the signal intensity and background noise, average specificity and sensitivity and reproducibility between replicated copies of the same probe. This method allows the correct genotype of the control DNA to be determined. As above, in accordance with the present method, a nucleic acid sample, e.g. amplification or fragmentation products, comprising the genetic variation(s) to be detected (target DNA) is contacted with a probe array as described herein, under conditions which allow hybridisation to occur between target DNA and the corresponding probes. Specific hybridisation complexes are thus formed between target nucleic acid and corresponding probes.

The hybridization of e.g. fragmentation products, with probes capable of detecting corresponding genetic variations deposited on a support may be carried out using conventional methods and devices. In one instance, hybridization is carried out using an automated hybridisation station. For hybridization to occur, the e.g. fragmentation products, are placed in contact with the probes under conditions which allow hybridization to take place. Using stable hybridization conditions allows the length and sequence of the probes to be optimised in order to maximize the discrimination between genetic variations A and B, e.g. between wild type and mutant sequences, as described herein.

In, one instance, the method relies on differential hybridisation, in particular an increase in hybridisation signal. The method involves formation of specific hybridisation complexes between target DNA and corresponding probes. Thus target DNA bearing the wild type sequence will hybridise to the probes designed to detect the wild type sequence, whereas target DNA bearing a mutant sequence will hybridise to the probes designed to detect that mutant sequence. The hybridisation complexes are detectably labelled by means described herein (e.g. the target DNA is directly labelled, or both target and probe are labelled in such a way that the label is only detectable on hybridisation). By detecting the intensity of detectable label (if any) at the predetermined probe positions it is possible to determine the nature of the target DNA in the sample. In this instance the probes (also referred to as allele specific oligonucleotides, ASOs) preferably have the variable nucleotide(s) at the central position, as described herein.

In another instance, hybridisation of target DNA to probes on the solid support (chip) may be followed by on-chip amplification, for example, using primer extension or ligation, e.g. oligonucleotide ligation assay (OLA) technologies (Eggerding F A, Iovannisci D M, Brinson E., Grossman P., Winn-Deen E. S. 1995 Human Mutation, 5:153-65). In this case, the probes on the support typically comprise the variable nucleotide(s) at the 3' end of the probe.

Labelling can be carried out during post hybridisation amplification. The labelling can be by direct labelling using, for example, fluorophores, enzymes, radioactive isotopes, etc. or by indirect labelling using, for example, specific binding pairs which incorporate fluorophores, enzymes etc., by using conventional methods, such as those previously mentioned in relation to labelling amplification or fragmentation products.

Post-hybridization amplification may be carried out, for example, using the "primer extension" methodology. Typically, after hybridization, an extension reaction of the hybrid oligonucleotides is carried out on the support (e.g. a glass slide). Extension may be carried out with directly or indirectly labelled nucleotides and will only happen if the extreme 3' of the oligonucleotide hybridizes perfectly with the amplification product.

Primer extension is a known method for genotype discrimination (Pastinen T, Raitio M, Lindroos K, Tainola P, Peltonen L, Syvanen A C. 2000 *Genome Research* 10:1031-42.) and can be performed in a number of different ways. In a commonly used approach a set of allele specific oligonucleotide probes are designed to hybridise to the target sequences. The probes differ from one another in their extreme 3' nucleotide, which for each probe is designed to complement one of the possible polymorphic nucleotides at a given position.

When the 3' nucleotide of the probe complements the sequence under test then the ensuing base pairing allows a DNA polymerase to extend the oligonucleotide primer by incorporation of additional nucleotides that can be directly or indirectly labelled thereby allowing the subsequent identification of those probes that have been extended and those that have not. Probes that are successfully extended carry the complementary nucleotide to the SNP at their 3' end thus allowing the genotype of the test sample to be determined. Similar approaches, for example the Amplification Refractory Mutation System (ARMS) have also been developed.

Alternatively, a post hybridization ligation reaction may be carried out, for example using OLA methodology. After hybridization, a ligation reaction of the hybridised oligonucleotides is carried out on the support (e.g. glass slide) with labelled oligonucleotides. A ligation will only take place if the extreme 3' end of the probe deposited on the support hybridizes perfectly with the target DNA (e.g. amplification product).

The oligonucleotide ligation assay (OLA) is another method for interrogating SNPs (Eggerding F A, Iovannisci D M Brinson E., Grossman P., Winn-Deen E. S. 1995 Human Mutation, 5:153-65). OLA uses a pair of oligonucleotide probes that hybridize to adjacent segments of target DNA including the variable base. The probe designed to hybridise to the 5' side of the polymorphic nucleotide is an allele-specific oligonucleotide (ASO) to one of the target alleles. The last base at the 3' end of this ASO is positioned at the site of the target DNA's polymorphism; the ASO typically also has a biotin molecule at its 5' end that functions as a "hook" that can subsequently be used to recover the oligonucleotide by virtue of the highly specific interaction that biotin undergoes with streptavidin.

The oligomer on the 3' or right-hand side of the pair is the common oligomer (the sequence is the same for the two or more different alleles it is wished to test.) The common oligomer is positioned at an invariable site next to the target DNA's polymorphism and is fluorescently labelled at its 3' end.

If the ASO is perfectly complementary to the target sequence the ASO hybridizes completely when annealed and will lie flat against that target allowing DNA ligase to covalently join the ASO to the common oligomer. After the ligation reaction the biotin hook is used to remove the ASO and the e.g. fluorescently labeled common oligomer will also be removed, producing detectable fluorescence.

When the ASO is not a perfect match to the target sequence hybridization is incomplete and the 3' base of the oligomer will not be base-paired to the target DNA thus preventing ligation. Under these circumstances when the biotin hook is used to remove the ASO, the common oligonucleotide will not be removed and therefore there is no detectable label, e.g. fluorescence, in the molecule removed.

To distinguish between two known alleles that differ by a single base, three oligonucleotides are necessary: Two are allele-specific oligonucleotides (ASOs) that differ from each other only in the single 3' terminal base; the first is complementary to one allele and the second is complementary to the second allele. The third oligonucleotide is complementary to the invariable sequence adjacent to the variant base.

Once hybridisation (and optionally post-hybridisation amplification) has taken place, the intensity of detectable label at each probe position (including control probes) can be determined. The intensity of the signal (the raw intensity value) is a measure of hybridisation at each probe.

The intensity of detectable label at each probe position (each probe replica) may be determined using any suitable means. The means chosen will depend upon the nature of the label. In general an appropriate device, for example, a scanner, collects the image of the hybridized and developed DNA-chip. An image is captured and quantified.

In one instance, e.g. where fluorescent labelling is used, after hybridization, (optionally after post-hybridization amplification or ligation) the hybridized and developed DNA-chip is placed in a scanner in order to quantify the intensity of labelling at the points where hybridization has taken place. Although practically any scanner can be used, in one embodiment a fluorescence confocal scanner is used. In this case, the DNA-chip is placed in the said apparatus and the signal emitted by the fluorpohore due to excitation by a laser is scanned in order to quantify the signal intensity at the points where hybridization has taken place. Non-limiting examples of scanners which can be used according to the present invention, include scanners marketed by the following companies: Axon, Agilent, Perkin Elmer, etc.

Typically, in determining the intensity of detectable label at each probe position (i.e for each probe replica), account is taken of background noise, which is eliminated. Background noise arises because of non-specific binding to the probe array and may be determined by means of controls included in the array. Once the intensity of the background signal has been determined, this can be subtracted from the raw intensity value for each probe replica in order to obtain a clean intensity value. Typically the local background, based on the signal intensity detected in the vicinity of each individual feature is subtracted from the raw signal intensity value. This background is determined from the signal intensity in a predetermined area surrounding each feature (e.g. an area of X, Y or Z μm2 centred on the position of the probe).

The background signal is typically determined from the local signal of "blank" controls (solvent only). In many instances the device, e.g. scanner, which is used to determine signal intensities will provide means for determining background signal.

Thus, for example, where the label is a fluorescent label, absolute fluorescence values (raw intensity values) may be gathered for each probe replica and the background noise associated with each probe replica can also be assessed in order to produce "clean" values for signal intensity at each probe position.

Once the target DNA has been hybridised to the chip and the intensity of detectable label has been determined at the probe replica positions on the chip (the raw intensity values), it is necessary to provide a method (model) which can relate the intensity data from the chip to the genotype of the individual.

The inventors have found that this can be done by applying a suitable algorithm to the intensity data. The algorithm and computer software developed by the inventors allows analysis of the genetic variations with sufficient sensitivity and reproducibility as to allow use in a clinical setting. The algorithm uses three linear functions which characterise each of the three genotypes AA, AB and BB for a given genetic variation. The method generally involves collating the intensity values for all of the replicas of each probe, to calculate an average intensity value for each probe. Optionally, the raw intensity values for each replica may be amended to take account of background noise (to obtain a clean intensity value) before the intensity values for each of the replicas are collated.

In general, for a given genetic variation, analysis and interpretation of a chip comprises the following steps:

(a) providing the intensity of detectable label at each replica for each of at least four probes (probes 1, 2, 3 and 4) provided for detection of the genetic variation (the raw intensity value), wherein:
  probe 1 detects (is capable of specifically hybridising to) genetic variation A (e.g. a normal allele), and probe 2 detects (is capable of specifically hybridising to) genetic variation B (e.g. a mutant allele);
  probe 3 detects (is capable of specifically hybridising to) genetic variation A (e.g. a normal allele) and probe 4 detects (is capable of specifically hybridising to) genetic variation B (e.g. a mutant allele); and
  probes 1 and 2 form a first probe pair and probes 3 and 4 form a second probe pair;
(b) optionally amending the raw intensity value for each replica to take account of background noise, thus obtaining a clean intensity value;
(c) collating the (optionally clean) intensity values for each of the replicas of each probe and determining an average intensity value for each probe;
(d) calculating ratios 1 and 2 wherein:
  Ratio 1=average intensity value for probe 1
  average intensity value for probe 1
  average intensity value for probe 2
  and $$\text{Ratio 2} = \frac{\text{average intensity value for probe 3}}{\text{average intensity value for probe 3}}$$

average intensity value for probe 4
(e) inputting ratios 1 and 2 into each of three linear functions which characterise each of the three possible genotypes, AA, AB and BB, wherein:
  Function 1 is the linear function that characterises individuals with the genotype AA and consists of a linear combination of ratios 1 and 2;
  Function 2 is the linear function that characterises individuals with the genotype AB and consists of a linear combination of ratios 1 and 2;
  Function 3 is the linear function that characterises individuals with the genotype BB and consists of a linear combination of ratios 1 and 2;
  the linear functions are formed by coefficients which accompany the variables ratio 1 and 2;
(f) determining which of the three linear functions has the highest, value; and
(g) thereby determining the genotype of the individual for the genetic variation.

Thus the linear function corresponding to the genotype of that individual will have the highest absolute value.

The inventors have found that the use of replicas and averages calculated from replicas is important for reliable working of the invention. Use of the functions speeds up analysis and allows better discrimination.

Preferably the discrimination capacity between the three genotypes is (approximately) 100%. If the discrimination is less than 100% the probes are preferably redesigned.

The raw intensity value for each probe replica may be determined according to the methods described above. Thus probe sequences and replicas can be selected as described herein. In one example, 4 probes are used per genetic variation and 6, 8 or 10 replicas are used per probe.

Typically, amending the raw intensity value to obtain the clean intensity value for each probe replica comprises subtracting background noise from the raw value. Background noise is typically determined using appropriate controls as described herein.

Typically calculating the average intensity value comprises eliminating extreme values or outliers. Thus, when the (optionally clean) intensity values from each of the probe replicas are collated, outlying values can be identified and excluded from further consideration. In one embodiment outliers make up between 10% and 50%, for example, 15, 20, 25, 30, 35, 40 or 45% of the values obtained. In one embodiment, 40% of values are eliminated. In one embodiment, 4 probes are used with 6, 8 or 10 replicas per probe and extreme values or outliers make up between 10% and 50% of the values obtained.

A number of suitable linear functions are known in the art. These functions may be used in a linear discriminant analysis for the purposes of the present invention.

In one aspect the invention thus relates to a computational method or model (algorithm) for determining genotype with respect to a given genetic variation using ratios 1 and 2 in the three linear functions as defined above (steps e and f). The method can thus in one embodiment produce an output of genotype (AA, AB or BB) from an input of ratios 1 and 2. The method may also include calculating one or both of ratios 1 and 2 (step d). In some embodiments the method additionally comprises calculating an average intensity value for each probe (step c) and/or calculating a clean intensity value for each probe replica (step b). Thus the input to the model may comprise one or more of the average intensity values, clean replica intensity values or raw replica intensity values. The method may additionally comprise determining the raw intensity value for each probe replica (step a). The method may comprise one or more of the above steps.

In order to carry out the above methods, the coefficients for the linear functions must first be determined in a training process using data from control individuals whose genotype for the genetic variation is already known. Methods for training are known in the art. Typically in such methods, input data (in this case, typically ratios 1 and 2) is used for which the output (in the present case, genotype) is already known. Coefficients are substituted in the three linear equations at random and the output is calculated. Based on that output, one or more coefficients are altered and the input data is entered again to produce another output. The process is continued until coefficients are obtained which optimise the desired output. These optimised coefficients are then used in the linear functions when the method is applied to test data (where the output is as yet unknown).

In order to train the present model, ratios 1 and 2 are obtained for n control individuals having genotype AA (for example, homozygous wild type), n control individuals having genotype AB (heterozygous) and n control individuals having genotype BB (for example, homozygous mutant). The ratios may be obtained using the methods described above. The ratios are inputted as above and the coefficients altered in a discriminatory analysis until three linear functions are obtained which maximise discrimination between the AA, AB and BB groups. These coefficients are then used in the three functions when the model is used on unknown test samples (where the genotype is not predetermined).

Thus in one aspect the invention provides a method of deriving linear functions for use in the present genotyping methods. The method typically comprises carrying out the steps of the genotyping methods as described, for n control individuals having genotype AA (for example, homozygous wild type), n control individuals having genotype AB (heterozygous) and n control individuals having genotype BB (for example, homozygous mutant) with respect to a genetic variation. The intensity values obtained for each of the probe replicas are gathered as described and an algorithm is applied.

As described for the genotyping methods, application of the algorithm comprises calculating an average intensity value for each probe and the algorithm uses three linear functions intended to characterise each of the three possible genotypes, AA, AB and BB for the given genetic variation. Coefficients are inserted in the functions in a repetitive way until functions are derived which maximise discrimination between the genotypes in a discriminatory analysis. This provides the coefficients for use in the linear functions when the method or algorithm is in operational use (i.e. to determine the genotype of test individuals).

The algorithm or method which uses the three linear functions for analysing the intensity data may be as described above.

In some cases, the training method allows feedback optimisation. Thus, as intensity values and ratios are obtained for test individuals and these are genotyped, the intensity data, e.g. the ratios, and genotype are inputted and coefficients recalculated for the linear functions.

In one aspect the invention relates to a computational method for training. The method can be used to derive linear functions for use in the present genotyping methods by using ratios 1 and 2 obtained for each of n individuals having genotype M, n individuals having genotype AB and n individuals having genotype BB with respect to a genetic variation. The ratios can be obtained by the methods described above. The method typically comprises applying the algorithm which uses the three linear functions (Functions 1, 2 and 3) intended to characterise each of the three possible genotypes AA, AB or BB for the genetic variation such that:
Function 1 is the linear function that characterises individuals with the genotype AA and consists of a linear combination of ratios 1 and 2;
Function 2 is the linear function that characterises individuals with the genotype AB and consists of a linear combination of ratios 1 and 2;
Function 3 is the linear function that characterises individuals with the genotype BB and consists of a linear combination of ratios 1 and 2; and
the linear functions are formed by coefficients which accompany the variables ratio 1 and 2;
and deriving linear functions which maximise discrimination between the three genotype groups AA, AB and BB in a discriminatory analysis, so as to obtain the coefficients which can be used in the linear functions when the algorithm is used in a test method (i.e. is in operational use for determining genotype).

The algorithm or method which uses the three linear functions for analysing the intensity data may be as described above.

The computational training method may additionally involve calculating ratios 1 and 2 from average intensity value provided for each of the probes, and/or collating intensity values from probe replicas to determine an average intensity value for each probe and/or amending a raw intensity value for a probe replica to take account of background noise thereby obtaining clean intensity values for the replica.

In some aspects the computational method also allows a feedback optimisation step as described.

Typically in training n is $\geq 3$, for example, 3, 4, 5, 6, 7, 8, 9 or 10. In one aspect, n is $\geq 5$. In some cases n may be from 10 to 50 or more, for example, 15 to 40, or 25 to 35, such as 20 or 30.

Probes and probe replicas for the training method are selected as described herein. In one embodiment 4 probes are used for each genetic variation, with 6, 8 or 10 replicas of each probe. Once selected, the probes used in training are also used when the model is in operational use (to determine unknown genotype). If the probes are altered, typically the model must be retrained to optimise discrimination with the new probes.

Preferably the coefficients are such that the discrimination between the three genotype groups (both in training and in operational use) is substantially 100%. If the discrimination is not 100%, the probes are preferably redesigned.

As above, the model may also undergo feedback optimisation when it is in operational use. In that case, the model is first used to determine the genotype of an individual (AA, AB or BB). The ratios 1 and 2 for that individual are then inputted into the model and the coefficients in the linear functions altered as necessary in order to optimise discrimination between the three genotype groups. In this way, the additional data gathered as the model is in use can be used to optimise the discrimination capacity of the linear functions.

There are a number of parameters which can be determined and optimised in order to optimise performance and reliability of the analytical model or method.

(i) In one aspect ratios 1 and 2 determined for an individual fall within the range of ratios 1 and 2 used to train the model (i.e. to optimise the three linear functions). If desired this can thus provide a double test for the genotype of an individual.

(ii) In one aspect the average fluorescence intensity of 4n replicas (where "n" is the number of replicas for each probe, e.g. 6, 8 or 10), for example, 40 replicas, with regard to the background noise is greater than 5.

(iii) In one aspect the variation between intensity values (raw or clean) for replicas of the same probe is a minimum: For example, the coefficient of variation between the intensity values for the replicas of a given probe is preferably less than 0.25

(iv) In one aspect the ratio of the sum of the raw intensity values for all probe replicas on a chip to the intensity of the background noise is greater than 15 when a fluorescence scanner is used.

(v) In one aspect the raw signal intensity value obtained for the negative controls is 53 times greater than the intensity value of the background noise. For example, negative controls may include the DMSO "blank" and the non-hybridising oligonucleotides referred to above. The background noise is the signal derived from the regions of the array where no probe has been spotted and may be determined as above.

Preferably any one or more of (i) to (v) applies when intensity is fluorescence intensity of a fluorescent label, in particular where the intensity is determined by means of a confocal fluorescent scanner.

Ensuring that the model meets one or more of the above helps to provide reliability and reproducibility. Any one or more of (i) to (v) may be true for the model. Preferably the model meets (i) above. In one example, (i), (ii) and (iii) are true. In another example, (iii), (iv), (v) are true. Preferably, all of the above are true for the model. This applies both to training and to operational use.

As above, the experimentally derived ratios obtained for a test sample may be compared to the ratios previously obtained for the (n) control samples obtained from individuals of known genotype, where n is as above, usually >5, or >10, or >20. The reference ratios derived from analysis of the control samples permits a genotype to be assigned to the test sample. This can therefore be a double test.

In one instance the analytical method or algorithm of the invention comprises a sequence of the following steps: using 4 probes (2 pairs of probes) in replicate (6, 8 or 10 replicas), calculating the average intensity of each probe from the collated intensities of the replicas; calculating ratios 1 and 2 as above for the 2 pairs of probes (to detect the genetic variations A and B); substituting ratios 1 and 2 obtained in three linear equations which have been derived in a discriminatory analysis using ratios 1 and 2 calculated for "n" control patients with genotype AA, "n" control patients with genotype AB and "n" control patients with genotype BB (with respect to the genetic variation) (in one experiment "n" is 5); and determining the genotype of a patient for the genetic variation (for each genetic variation included in the DNA-chip) based on which linear function has the greatest absolute value. The test ratios may also be compared to the ratios of the "n" control patients to determine each genotype.

The analysis and interpretation above has been described with respect to one genetic variation. However, it is to be understood that the present chip generally includes probes for detection of multiple genetic variations which can be analysed at the same time. Thus the present methods include analysis of multiple genetic variations, as described herein, in parallel.

In a further aspect the invention relates to a computer system comprising a processor and means for controlling the processor to carry out a computational method of the invention. The invention additionally relates to a computer program comprising computer program code which when run on a computer or computer network causes the computer or computer network to carry out a computational method of the invention. The computer program may be stored on a computer readable medium.

In addition to the probes and chips described herein, the inventors have also designed and validated oligonucleotide primers which are capable of amplifying, e.g. by means of multiplex PCR, target DNA regions containing the human genetic variations associated with osteoporosis in Table 1A/1B. These primers are useful in preparing nucleic acid for use in the present genotyping, prognostic and therapeutic methods.

Tables 3A, 3B and 3C list pairs of primers which amplify target DNA regions containing the osteoporosis associated genetic variations in Table 1A/1B along with the corresponding genetic variation.

The listed oligonucleotide primers have the advantage of allowing specific amplification of the said target DNA regions in a very low number of PCR reactions. The listed primers in Table 3A or 3C allow, in a minimum number of multiplex PCR reactions, amplification of all the fragments necessary for genotyping the genetic variations in Table 1A/1B, and which may be analyzed on Osteochip.

In a further aspect, the present invention relates to each of the PCR primers listed in Tables 3A, B and C, and in particular to each of the listed pairs of PCR primers and their use in PCR amplification, e.g. in a multiplex PCR reaction, of a target DNA region containing the corresponding genetic variation. The invention in one aspect provides any one of these primers or pairs of primers for use in medicine, in particular for use in the present genotyping, diagnostic/prognostic or therapeutic methods.

The invention further relates to a PCR amplification kit comprising at least one pair of listed PCR primers. The kit may additionally include, for example, a (thermostable) polymerase, dNTPs, a suitable buffer, additional primers, and/or instructions for use, e.g. to amplify a target DNA region containing the corresponding genetic variation. The kit may be used for amplification of target DNA regions from nucleic acid samples, for use in the present methods.

In another aspect the present invention relates to a genotyping or diagnostic (preferably in vitro) kit for genotyping osteoporosis associated genetic variations and/or for diagnosing osteoporosis or susceptibility to osteoporosis. The kit comprises a DNA-chip or array according to the invention.

The kit may additionally comprise instructions for use of the chip in a genotyping method of the invention, for example instructions for use in the present analytical method or algorithm. Further components of a kit may include:
  computer software, a computer program or a computer system according to the invention;
  one or more PCR primers or pairs of PCR primers according to the invention; and/or
  a PCR amplification kit according to the invention.

The probes for the chip or PCR primers may be selected as above depending on the genetic variations to be detected or the diagnostic purpose of the kit.

The kit may contain one or more positive and/or negative controls of the hybridisation reaction. The invention further relates to the use of the kit in a genotyping, prognostic or therapeutic method of the invention.

As described herein, the present genotyping methods are useful for diagnosing osteoporosis or susceptibility to osteoporosis in a subject. The genotyping results obtained in the methods may be used to determine prognosis and may be useful in determining the appropriate treatment for osteoporosis (e.g. by predicting response to therapy).

Osteoporosis presents a number of phenotypes, most notably skeletal fragility and susceptibility to fracture, which are complex polygenic traits that will be affected by variation in many different genes. Genetic variants involved in determining bone mass, density, size, geometry, microarchitecture, fragility, and trauma risk are also important in determining the risk to an individual of an osteoporotic fracture.

Particular genetic variations associated with osteoporosis may be predictive of particular phenotypes or development of particular phenotypes and hence disease progression. In other words, it may be that there is a statistically significant association between e.g. the mutant allele B, of a given genetic variation and the occurrence/development of a particular phenotype.

Since the present genotyping methods allow reliable genotyping of multiple genetic variations in a clinical setting, these can be used to genotype individuals of known osteoporosis phenotype, and to thus identify genetic variations predictive of particular osteoporosis phenotypes.

In one aspect the invention therefore relates to a method of identifying genetic variations predictive of a particular osteoporosis phenotype, such as the phenotypes listed above. The method involves genotyping a plurality of individuals with respect to one or more genetic variations associated with osteoporosis using a method of the invention. In such a retrospective study typically 300-1000 individuals are genotyped, for example 400, 500 or 600 individuals may be genotyped. The osteoporosis disease phenotype, is already known, based on standard clinical parameters (e.g. bone mineral density, history of bone fracture) for all individuals to be genotyped.

Once the genotypes are obtained, this data is compared with the phenotype data and statistically significant associations between particular genotypes and particular phenotypes are identified. Methods for determining statistical significance are known in the art.

The genetic variations identified as predictive of particular phenotypes/disease course can then be used to diagnose these phenotypes/disease courses in test individuals, by genotyping the individuals with respect to the predictive genetic variation(s). Thus it is possible to determine the likely course of disease progression in the individual. Genotyping can be done by any appropriate method, depending on the number of variations to be tested. For example, a genotyping method of the invention may be used. Alternatively, sequence based or other chip-based methods may be appropriate.

Thus in one aspect the invention further relates to a method of diagnosing osteoporosis phenotype or predicting the likely course of disease progression in an individual by determining the genotype of the individual with respect to one or more genetic variations which have been identified as predictive (of the particular Osteoporosis phenotype or disease course) by the methods described herein.

Once the prediction has been made, it will then be possible to select the most suitable therapeutic approach, e.g. to determine the need for surgical intervention.

The present arrays and methods thus provide a means for clinicians to predict the likely course of disease progression in osteoporosis patients and also aid in the selection of the most suitable treatment regime. They are therefore useful prognostic tools. Genotype information obtained according to the present invention may aid in clinical decision making or diagnosis in cases where symptoms (disease phenotype) are ambiguous. Genetic information provided by Osteochip or other methods could also help in determining the likelihood of disease development in asymptomatic individuals (e.g. immediate family members of osteoporosis sufferers) allowing, for example, guidance on lifestyle and diet to be provided and indicating the need for continued monitoring of individuals who have a genetic constitution that indicates possible susceptibility to disease development.

In one aspect the invention therefore relates to a method of diagnosing osteoporosis or susceptibility to osteoporosis in an individual, or determining the likely course of disease progression in an individual as above. Preferably the method is in vitro. The invention further relates to a method of selecting a treatment, for an individual having osteoporosis, in some cases where the individual has been diagnosed or tested according to the methods of the invention. Still further the invention in some aspects relates to methods of treating an individual suffering from osteoporosis, wherein, after the treatment is selected, the treatment is administered to the individual.

The diagnostic, predictive and therapeutic methods may comprise carrying out a genotyping method of the invention as described herein. Any of the methods may involve carrying out a training method of the invention as described herein in order to derive linear functions for use in determining genotype. Further the methods may comprise the use of a chip, computer system, computer program, oligonucleotide probes or pair or set of probes, oligonucleotide primer or pair of primers, PCR amplification kit or diagnostic kit of the invention as described herein.

In one aspect the present invention relates to a microarray adapted for use in the present methods as described herein.

The invention further relates to the use of one or more oligonucleotide probe(s) and/or one or more primer(s) or primer pair(s) of the invention in a method for prognosing osteoporosis, such as a method described herein.

Further aspects of the invention will now be illustrated with reference to the accompanying Figures and experimental exemplification, by way of example and not limitation. Further aspects and embodiments will be apparent to those of ordinary skill in the art. All documents mentioned in this specification are hereby incorporated herein by reference.

EXAMPLES

Although in general, the techniques mentioned herein are well known in the art, reference may be made in particular to Sambrook et al, 1989, Molecular Cloning: a laboratory manual.

Example 1

Detection of Osteoporosis Associated Human Genetic Variations Using a DNA-Chip According to the Invention (Osteochip)

1.1 Design of the DNA-Chip for Genotyping Osteoporosis Associated Genetic Variations A DNA-chip to detect human genetic variations associated with osteoporosis which permits simultaneous, sensitive, specific and reproducible detection was designed and manufactured. The said genetic variations are related to a greater or lesser risk of suffering from osteoporosis, a better or worse response to treatment and also a better or worse prognosis of the disease. Illustrative examples of human genetic variations associated with antigens connected to osteoporosis which can be determined using this DNA-chip are shown in Tables 1A and 1B.

The DNA-chip designed and manufactured consists of a support (glass slide) which shows a plurality of probes on its surface that permits the detection of genetic variations previously mentioned. These probes are capable of hybridizing with the amplified sequences of the genes related to osteoporosis. The DNA sequences of each one of the probes used is referred to below in Table 2A (FIG. 2). All of the listed probes have been technically validated.

1.2 Production of the DNA-Chip

Printing and Processing of the Glass Slides

The probes capable of detecting the genetic variations previously identified are printed onto aminosilane coated supports (glass slides) using DMSO as a solvent. The printing is carried out using a spotter or printer of oligonucleotides (probes) while controlling the temperature and relative humidity.

The joining of the probes to the support (glass slides) is carried out by means of crosslinking with ultraviolet radiation and heating as described in the documentation provided by the manufacturer (for example, Corning Lifesciences, available on the World Wide Web at www.corning.com). The relative humidity during the deposition process is maintained between 40-50% and the temperature around 20° C.

1.3 Validation of the Clinical Usefulness of the DNA-Chip 1.3.1 Preparation of the Sample to be Hybridized The DNA of the individual is extracted from a blood sample by a standard protocol of filtration. (For example, commercial kits from Macherey Nagel, Qiagene etc).

Target DNA regions containing the genetic variations of interest are amplified by multiplex PCR using appropriate pairs of oligonucleotide primers. Any suitable pair of oligonucleotides can be used which allow specific amplification of genetic fragments where a genetic variation to be detected might exist. Advantageously, those pairs of oligonucleotide primers which permit the said amplifications to be performed in the least possible number of PCR reactions are used.

The oligonucleotide primers used to PCR amplify (by multiplex PCR) target regions containing the genetic variations in Tables 1A and 1B are in Table 3A (FIG. 3). These primers represent an additional aspect to the invention.

The PCR multiplex reactions are carried out simultaneously under the same conditions of time and temperature which permit specific amplification of the gene fragments in which the genetic variations to be detected might exist. Once the PCR multiplex has finished, agarose gel analysis is used to check that the amplification reaction has taken place.

Next, the sample to be hybridized (products of amplification) is subjected to fragmentation with a DNase and the resulting fragmentation products subjected to indirect labelling. A terminal transferase adds a nucleotide, covalently joined to one member of a pair of molecules that specifically bind to one another (e.g. biotin allowing subsequent specific binding to streptavidin) to the ends of these small DNA fragments.

Before applying the sample to the DNA-chip, the sample is denatured by heating to 95° C. for 5 minutes and then, the "ChipMap Kit Hybridization Buffer" (Ventana Medical System) is added.

1.3.2 Hybridization

Hybridization is carried out automatically in a hybridisation station such as the Ventana Discovery (Ventana Medical Systems) that has been specifically developed for such a use. Alternatively hybridisation can be performed manually.

The prehybridization and blocking of the slides is carried out with BSA. Next, the hybridization solution {ChipMap Kit Hybridization Buffer, Ventana Medical System) is applied to the surface of the DNA-chip which is maintained at 45° C. for 1 hour following the protocol of Ventana 9.0 Europe (Ventana Medical System). Finally the slides are subjected to different cleaning solutions (ChipMap hybridisation Kit Buffers, Ventana Medical System). Once the process of hybridization has finished, the final cleaning and drying of the slides begins.

When hybridization has taken place, the DNA chip is developed by incubation with a fluorescently labelled molecule that is able to specifically bind to the molecule incorporated into the amplification product by terminal transferase (e.g. in the case of biotin incorporation a fluorophore coupled to streptavidin such as streptavidin-Cy3 can be used) to label the probe positions where hybridization has occurred.

1.3.3. Scanning the Slides

The slides are placed in a fluorescent confocal scanner, for example Axon 4100$^a$, and the signal emitted by the fluorophore is scanned when stimulated by the laser.

1.3.4 Quantification of the Image

The scanner's own software allows quantification of the image obtained from the signal at the points where hybridization has taken place.

1.3.5 Interpretation of the Results

From the signal obtained with the probes which detect the different genetic variations, the genotype of the individual is established. In the first instance the scanner software executes a function to subtract the local background noise from the absolute signal intensity value obtained for each probe. Next, the replicates for each of the 4 probes that are used to characterize each genetic variation are grouped. The average intensity value for each of 4 probes is calculated using the average collated from the replicates in order to identify abnormal values (outliers) that can be excluded from further consideration. Once the average intensity value for each of the probes is known then two ratios are calculated (ratio 1 and ratio 2):

Average Intensity for Probe 1

$$\text{Ratio 1} = \frac{\text{Average Intensity for Probe 1}}{\text{Average intensity for probe 1} + \text{Average intensity for probe 2}}$$

Average Intensity for Probe 3

$$\text{Ratio 2} = \frac{\text{Average Intensity for Probe 3}}{\text{Average intensity for probe 3} + \text{Average intensity for probe 4}}$$

wherein probe 1 detects (is capable of specifically hybridising to) genetic variation A (e.g. a normal allele), probe 2 detects (is capable of specifically hybridising to) genetic variation B (e.g. a mutant allele), probe 3 detects (is capable of specifically hybridising to) genetic variation A (e.g. a normal allele) and probe 4 detects (is capable of specifically hybridising to) genetic variation B (e.g. a mutant allele).

These ratios are substituted in three linear functions which characterize each one of the three possible genotypes:

| | |
|---|---|
| AA | Function 1 |
| AB | Function 2 |
| BB | Function 3 |

The function which presents the highest absolute value determines the genotype of the patient.

In this case, the linear functions are obtained by analyzing 5 subjects for each of the three possible genotypes of the genetic variation (AA, AB, BB). With the results, ratios 1 and 2 are calculated for the 15 subjects. These ratios are classification variables for the three groups to create the linear functions, with which the discriminatory capacity of the two pairs of designed probes are evaluated. If the discriminatory capacity is not 100%, the probes are redesigned. New subjects characterized for each of the three genotypes make up new ratios 1 and 2 to perfect the linear functions and in short, to improve the discriminatory capacity of the algorithm based on these three functions.

When using a confocal fluorescent scanner, to obtain reliable results it is preferable that ratios 1 and 2 are within the range of the ratios used to build the groups, the average fluorescence intensity of the 4n (for example 40) replicates with regard to background noise is greater than 5 and the coefficient of variation of all of the DNA-chip replicates is below 0.25.

Again when a fluorescent confocal scanner is used in the experiment, for a complete hybridization to be considered reliable preferably the ratio of probe fluorescence intensity to background noise of all the DNA-chip probes is above 15.

Likewise, the average of all the ratios is preferably above 0.6 and the negative control is preferably less than or equal to 3 times the background noise.

To sum up, in this example 4 probes (repeated 10 times) are presented on the slide for detection of each mutation. Two of the probes detect one genetic variation (A) and the other two the other genetic variation (B). The examined base is located in the central position of the probes.

A subject homozygous for the genetic variation A will not show genetic variation B. Consequently, in the image obtained from the glass support the probes which detect genetic variation B will show a hybridization signal significantly less than that shown by variation A and vice versa. In this case the ratios 1 and 2 will show 1 and the subjects will be assigned as homozygous AA by the software analysis.

On the other hand, a heterozygous subject for the determined genetic variation shows both the genetic variations. Therefore, the probes which detect them show an equivalent hybridization signal. The ratios 1 and 2 will show 0.5 and the subject will be assigned as heterozygous AB by the software analysis.

Example 2

Establishing Models for Predicting Osteoporosis Phenotypes Patients and Methods 2.1. Selection of Patients A cohort of 904 postmenopausal Italian women and elderly Italian men and 125 consecutive patients with non-traumatic fractures were selected. BMD (spine-LS, hip-FN and hand) and other phenotypes relevant to the pathogenesis of osteoporosis, such as ultrasound properties of bone, bone volume, bone turnover (bone alkaline phosphatase and serum CTX), PTH and sex hormone levels were evaluated. Besides, Osteoporosis diagnosis was made on the basis of WHO criteria on the basis of BMD (Tscore+Zscore). Hip, vertebral, wrist and other kind of fractures were already registered. Age, menopause age, menarche age, gender, smoking habits, weight, height, and physical exercise were also considered as covariates.

Clinical characteristics of the cohort and patients included in the present study are shown in FIG. 4 (Table 4).

The medical-ethics committee of Policlinico Santa Maria alle Scotte, (having its office in Italy, at Viale Bracci 1, 53100 SIENA) approved the study, and the participants gave written informed consent. The study has followed the ethical issues of the The World Medical Association's Declaration of Helsinki.

2.2. Genotyping by the Osteochip Array

Venous blood samples were collected into tubes containing anticoagulant to obtain genomic DNA. DNA was isolated from peripheral blood cells using the salting out method (Miller et al., 1988).

The methodology for genotyping based on DNA arrays has been previously reported (Tejedor et al., 2005). Briefly, two pairs of oligonucleotides were designed for the detection of each SNP to ensure the accuracy of SNP detection. Each probe pair consisted of a probe specific for the A allele and a probe specific for the B allele. Several replicates of each oligonucleotide probe were spotted on aminosilane-coated glass slides (UltraGAPs, Corning) using a Microgrid II robotic spotter (BioRobotics). The length of the oligonucleotides ranges from 17 to 25 nucleotides with the target polymorphic nucleotide located in the central position of the oligonucleotide in order to maximize hybridization specificity (FIG. 2, Table 2A).

Target DNA for hybridisation was prepared in 8 independent multiplex amplification reactions, each of which contained 14, 12, 15, 14, 13, 14, 15 and 13 separate primer pairs respectively (FIG. 3, Table 3A). The multiplex amplification reactions were performed simultaneously using the same thermocycling program, allowing amplification of 110 DNA fragments. Each multiplex amplification reaction was performed using genomic DNA as template, and the appropriate primer pairs. The amplification reaction was performed using an initial denaturation at 95° C. for 15 min, followed by 45 cycles of denaturation at 95° C. for 30 s, primer annealing at 62° C. for 90 s, and primer extension at 72° C. for 90 s, after the final amplification cycle primer extension was extended to 10 min at 72° C. The sizes of the fragments amplified (amplicons) ranged from 100 to 400 bp.

Following amplification the resulting products were fragmentated by digestion with DNAase I, and terminal transferase (Roche) was used to catalyse the addition of a biotinylated nucleotide (Perkin Elmer) to the 3'-hydroxyl termini of the double stranded DNA fragments.

Hybridization was carried out automatically at 45° C. for 1 h in a Ventana Discovery station using ChipMap hybridization buffers and the protocol for the Microarray 9.0 Europe station (Ventana Medical Systems). Following labelling the biotinylated DNA fragments were allowed to hybridise to the array in the automated hybridization station and stained with Cy3-conjugated streptavidin (Amersham Biosciences). Prior to scanning the DNA arrays were washed in order to remove non-specifically bound Cy3 molecules.

DNA array images were captured by use of a GenePix Pro 4100 confocal fluorescent scanner (Axon), equipped with a green laser (543 nm for Cy3 excitation). Absolute values of the Cy3 hybridization signal from each oligonucleotide probe were obtained by use of Gene Pix Pro Acuity 4.0 software (Axon). After scanning and quantifying the hybridization signals from the array, the export file from the scanner was processed with the genotyping software MG v1.0 (Tejedor D et al 2005). The ratio of the hybridization signal mean of the A allele to the sum of hybridization signal means of the A and B alleles was then defined for the 2 pairs of oligonucleotides used for genotyping each SNP (ratios 1 and 2). The specificity and sensitivity of the DNA array were assessed by use of at least 10 control DNA samples for each genotype group, identified previously by nucleotide sequence analysis in at least one of the ten cases for each genotype. These DNA control samples were used to determine the 2 ratio values corresponding to the 3 clusters (AA, AB and BB). In the present study, MG 1.0 software was used to determine to which of the previously defined clusters each of the 1029 samples belonged.

2.3. Statistical Analysis

Statistical analyses were performed using the Statistical Package for the Social Sciences (SPSS) version 14.0. A $x^2$ test was performed in order to determine that distribution of the genetic polymorphisms under analysis were in Hardy-Weinberg equilibrium. Genotype-phenotype associations were analysed by means of multivariate logistic regression with clinically determined disease phenotypes as dependent variables and the SNPs as independent variables. To evaluate the impact of the SNPs included in the DNA array in the prognosis of the analysed phenotypes, the sensitivity, specificity, and positive likelihood ratio (LR+=sensitivity/(1-specificity)) were computed by means of Receiver Operating Characteristic curves. Comparisons of mean probability function values between each of the compared phenotypes were performed using a t-test. The threshold for statistical significance was predefined as a p level of $\leq 0.05$.

Genotype-quantitative trait associations were analysed by means of multivariate linear regression with quantitative trait as dependent variables and the SNPs as independent variables. To evaluate the impact of the SNPs and the clinical variables analysed in the estimation of BMD, $R^2$ values were computed.

Results 2.1. Specificity and Sensitivity of Osteo DNA Array as a Genotyping Tool The specificity and sensitivity of this genotyping DNA array technology are 99.7% and 99.9%, respectively, as has been described previously (Tejedor et al, 2005). Three independent genotyping clusters were obtained for each SNP analyzed.

2.2. Genotype-Phenotype Associations

All genotype distributions of cohort patients were in Hardy-Weinberg equilibrium. Genotype-phenotype associations were analysed by means of logistic regression including as the dependent variable the clinically determined disease phenotype (described in 2.2.1 and 2.2.2) and as independent variables the variables shown in Table 5 (FIG. 5). Probability functions were obtained for each phenotype analysed. Informative SNPs included in each probability function are shown in Table 5.

2.2.1. Fractures and Vertebral Fracture Risk in Males

To identify predictors for development of fractures or vertebral fractures in males, a logistic regression analysis was performed with the presence of fractures or vertebral fractures as dependent variable.

The probability function fractures in males compares individuals suffering from fractures (1) against individuals without fractures (0). The variables included in the fractures function in males are indicated in Table 5.

The statistical analysis showed that the SNPs included in the probability function fractures in males (Table 5) were able to predict fractures with a sensitivity of 57% at a specificity of 95% (LR+=11.4). The 1 and 0 individuals are also represented in the box plot FIG. 6.1. Comparing mean probability function values fractures in males function, statistically significant differences were found between both subgroups: 1 vs 0, P<0.05.

The probability function vertebral fractures in males compares individuals suffering from vertebral fractures (1) against individuals without vertebral fractures (0). The variables included in the fractures function in males are indicated in Table 5.

The sensitivity and specificity values of vertebral fractures function in males were 71% and 94%, respectively, with a positive likelihood ratio (LR+) of 11.8. The 1 and 0 individuals are also represented in the box plot FIG. 6.2. Comparing mean probability function values fractures in males function, statistically significant differences were found between both subgroups: 1 vs 0, P<0.05.

2.2.2. Fractures and Vertebral Fracture Risk in Females

To identify predictors for development of fractures or vertebral fractures in females, a logistic regression analysis was performed with the presence of fractures or vertebral fractures as dependent variable.

The probability function fractures in females compares individuals suffering from fractures (1) against individuals without fractures (0). The variables included in the fractures function in females are indicated in Table 5.

The statistical analysis showed that the SNPs included in the probability function fractures in females (Table 5) were able to predict fractures with a sensitivity of 55% at a specificity of 95% (LR+=11). The 1 and 0 individuals are also represented in the box plot FIG. 7.1. Comparing mean probability function values fractures in males function, statistically significant differences were found between both subgroups: 1 vs 0, P<0.05.

The probability function vertebral fractures in females compares individuals suffering from vertebral fractures (1) against individuals without vertebral fractures (0). The variables included in the fractures function in females are indicated in Table 5.

The sensitivity and specificity values of vertebral fractures function in females were 72% and 95%, respectively, with a positive likelihood ratio (LR+) of 14. The 1 and 0 individuals are also represented in the box plot FIG. 7.2. Comparing mean probability function values fractures in males function, statistically significant differences were found between both subgroups: 1 vs 0, P<0.05.

2.3. Genotype-Quantitative Trait Associations

All genotype distributions of cohort patients were in Hardy-Weinberg equilibrium.

Genotype-quantitative trait associations were analysed by means of linear regression including as the dependent variable the quantitative trait (described in 2.3.1 and 2.3.2) and as independent variables the variables shown in Table 5. Quantitative functions were obtained for each quantitative trait analysed. Informative SNPs included in each probability function are shown in Table 5.

2.3.1. LSBMD and FNBMD in Males

To identify predictors for estimating LSBMD and FNBMD in males, a linear regression analysis was performed with the presence of LSBMD and FNBMD as dependent variable.

The quantitative functions estimate LSBMD and FNBMD on the basis of SNPs, age and BMI. The variables included in the LSBMD and FNBMD functions in males are indicated in Table 5.

The quantitative function for estimating LSBMD in males showed an $R^2$ of 0.38 (FIG. 3). The quantitative function for estimating FNBMD in males showed an $R^2$ of 0.35 (FIG. 8).

2.3.2. LSBMD and FNBMD in Females

To identify predictors for estimating LSBMD and FNBMD in females, a linear regression analysis was performed with the presence of LSBMD and FNBMD as dependent variable.

The quantitative functions estimate LSBMD and FNBMD on the basis of SNPs, age, menopause age, menarche age and BMI. The variables included in the LSBMD and FNBMD functions in females are indicated in Table 5.

The quantitative function for estimating LSBMD in females showed an $R^2$ of 0.3 (FIG. 8). The quantitative function for estimating FNBMD in females showed an $R^2$ of 0.32 (FIG. 8).

2.4. General Associations with LSBMD, FNBMD, Fractures and Vertebral Fractures by Gender.

Some conclusions can be assessed on the basis of Table 5:

ADRB1 gene SNPs showed an association with fractures and vertebral fractures in both genders.

ADRB2 gene SNPs showed an association with FNBMD and fractures in both genders.

ALOX12 gene SNPs showed an association with LSBMD and FNBMD in both genders. Another association was already assessed with fractures in females and vertebral fractures in both genders.

ALOX15 gene SNPs showed an association with LSBMD in both genders and vertebral fractures in males.

ALOX5 gene SNPs showed an association with LSBMD and FNBMD in both genders.

ALOX5P gene SNPs showed an association with LSBMD in both genders and fractures in males.

AR (androgen receptor) gene SNPs showed an association with FNBMD in females, fractures in males and vertebral fractures in females.

Aromatase gene SNPs showed an association with LSBMD and FNBMD in males. Besides, an association with fractures in both genders were assessed.

BMP4 gene SNPs showed an association with LSBMD and FNBMD in females. The association was also showed with fractures and vertebral fractures in both genders.

BMP6 gene SNPs showed an association with FNBMD in females. These SNPs were also associated with fractures and vertebral fractures in both genders.

CaSR gene SNPs were associated with fractures in males and vertebral fractures in females.

CICN7 gene SNPs showed an association with LSBMD and FNBMD in both genders. These SNPs were also associated with fractures and vertebral fractures in females.

Col1A1 gene SNPs showed an association with vertebral fractures in both genders.

Col1A2 gene SNPs showed an association with LSBMD and FNBMD in females and vertebral fractures in both genders.

COMT gene SNPs showed an association with LSBMD and FNBMD in both genders. These SNPs were also associated with fractures in females and vertebral fractures in both genders.

COX1 gene SNPs showed an association with LSBMD and FNBMD in males, and vertebral fractures in females.

CTR gene SNPs showed an association with LSBMD in males and females, and fractures in females.

CYP17 gene SNPs were associated with fractures in females.

CYP1A1 gene SNPs showed an association with fractures and vertebral fractures in males.

CYP1B1 gene SNPs showed an association with LSBMD and FNBMD in males, and vertebral fractures in both genders.

ESRA gene SNPs showed an association with fractures and vertebral fractures in both genders.

ESRB gene SNPs showed an association with LSBMD and FNBMD in males.

FDPS gene SNPS showed an association with fractures in males and vertebral fractures in both genders.

IGF-II gene SNPs showed an association with fractures in females and vertebral fractures in both genders.

IL-10 gene SNPs showed an association with fractures and vertebral fractures in males.

IL-1 RA gene SNPs showed an association with fractures in females and vertebral fractures.

IL-6 gene SNPs showed an association with LSBMD and FNBMD in both genders, and fractures in females, and fractures in females.

INTEGRINB3 gene SNPs showed an association with fractures in both genders and vertebral fractures in females.

KL gene SNPs showed an association with fractures in females.

LRP5 gene SNPs showed an association with LSBMD and FNBMD in both genders, fractures in females and vertebral fractures in both genders.

LRP6 gene SNPs showed and association with fractures in females.

MTHFR gene SNPs showed and association with vertebral fractures in males.

OPG gene SNPs showed an association with LSBMD and FNBMD in males.

PPARGAMMA gene SNPs showed an association with LSBMD and FNBMD in males, fracturas and vertebral fractures in both genders.

PTH gene SNPs showed an association with fractures in males and vertebral fractures in both genders.

PTHR1 gene SNPs showed an association with LSBMD and FNBMD in males and females, fractures in both genders and vertebral fractures in males.

RANKL gene SNPs showed an association with LSBMD and FNBMD in females.

SOST gene SNPs showed an association with LSBMD and FNBMD in males.

SRD5A2 gene SNPs showed an association with FNBMD in females, fractures and vertebral fractures in both genders.

TGF-B1 gene SNPs showed an association with LSBMD and FNBMD in males, fractures in males and vertebral fractures in females.

ALPL gene SNPs showed an association with FNBMD in females, and vertebral fractures in males.

VITDR gene SNPs showed an association with LSBMD and FNBMD in females, fracturas and vertebral fractures in both genders.

TNFalpha and TNFR2 gene SNPs showed an association with fractures and vertebral fractures in males.

Discussion

Currently, diagnosis of osteoporosis is based on measurement of BMD (LSBMD and/or FNBMD). The diagnosis cannot practically be applied to the general population, because not enough BMD measurement machines are available. Besides, the diagnosis is normally made only when a fracture has already appeared. The present methods provide accurate BMD (LSBMD and FNBMD) estimation and fractures prediction, and are therefore helpful in preventing osteoporosis and fractures. Osteochip also provides the first tool for selecting those patients with high risk of fractures.

The Osteochip described in the present study is the first low-density DNA array for diagnosis and prognosis of Osteoporosis based on hybridisation to allele-specific oligonucleotide probes that is able to screen for such a large number of SNPs.

Thus the Osteochip and the present methods provide an additional tool for clinical disease management thereby benefiting both patients and their doctors.

Example 3

Providing Further Models for Predicting Fractures of the Wrist, Hip or Spine (WSHfractures Phenotype)

Using chemical data and genomic DNA samples from the same population as in Example 2, the inventors carried out a further study of fractures.

In this study, vertebral, femoral and wrist fractures were grouped together as a single phenotype. Thus, in this study, positive fractures were considered as wrist, spine and hip non-traumatic fractures. The aim was to compare fractures occurring in any of these three places as opposed to fractures occurring anywhere else in the body.

The population was genotyped by the same method as in Example 2, but using the probes in Table 2C and the primers in Table 3C (thus incorporating the optimised probes of Table 2B and optimised primers of Table 3B, compared to the Example 2 study).

Statistical analysis was carried out as in Example 2, except where indicated below.

Three different approaches were carried out. The first one does not take into account gender. This results in the "General Models". The other two approaches separate between male and female populations, generating the "Male Models" and the "Female Models" respectively.

For each of the three approaches, two probability functions were generated, one using the Forward variable selection (FSTEP) and the other using the Backstep (BSTEP) variable selection. These are two methodologies for constructing models by the same statistical approach (multivariate logistic regression). In the Example 2 only BSTEP was considered.

The variables included in each model are listed in FIG. 9. FIGS. 10-15 show ROC curves for each of the six models showing the relationship between specificity and sensitivity. The Figures also show probability boxplots showing probability distributions for each group considered in the analysis (1=Vertebral, femoral and wrist fractures; 0=No Vertebral, femoral or wrist fractures. Sensitivity, specificity, and LR+ values for each of the models are shown in FIG. 16.

Data for calculation of probability functions for each of the models is shown in FIGS. 17 to 19.

The backstep models appeared to give better results in all three studies. For the General Models and the Female models, both Backstep and Forward results were rather similar. However, for the Male population, Backstep gave much better results, suggesting that Backstep model might be overfitting data.

The TAG sequences added to the forward and reverse primers are:

```
SEQ ID NO 672      TTGAAGTTCG
                   CAGAATCGTA

SEQ ID NO 673      AATACACGAA
                   GGAGTTAGCT
```

REFERENCES

1. Sundeep Khosla, B. Lawrence Riggs, Elizabeth J. Atkinson, et al. Relationship of Estrogen Receptor Genotypes to Bone Mineral Density and to Rates of Bone Loss in Men. The Journal of Clinical Endocrinology & Metabolism 89(4):1808-1816
2. Nigel A. Morrisona, Peter M. Georgeb, Tanya Vaughana, et al. Vitamin D receptor genotypes influence the success of calcitriol therapy for recurrent vertebral fracture in osteoporosis. Pharmacogenetics and Genomics 2005, 15:127-135
3. I. Sayers*, S. Bartonw, S. Rorkew, et al. Promoter polymorphism in the 5-lipoxygenase (ALOX5) and 5-lipoxygenaseactivatingprotein (ALOX5AP) genes and asthma susceptibility in a Caucasian population. Clin Exp Allergy 2003; 33:1103-1110
4. Tomohiko Urano, Masataka Shiraki, Masayo Fujita, et al. Association of a single nucleotide polymorphism in the lipoxygenase ALOX15 5_-flanking region (_5229G/A) with bone mineral density. J Bone Miner Metab (2005) 23:226-230
5. Chitra Sundarrajan, Wu Xiang Liao, Ashim Chandra Roy, et al. Association between Estrogen Receptor-b Gene Polymorphisms and Ovulatory Dysfunctions in Patients with Menstrual Disorders. The Journal of Clinical Endocrinology & Metabolism. Vol. 86 (2001).
6. Masaki Inada*†, Yingmin Wang*\, Michael H. Byrne*, et al. Critical roles for collagenase-3 (Mmp13) in development of growth plate cartilage and in endochondral ossification. PNAS Dec. 7, 2004; 101.
7. Koustubh Ranade, Eric Jorgenson, Wayne H.-H. Sheu, et al. A Polymorphism in the b1 Adrenergic Receptor Is Associated with Resting Heart Rate. Am. J. Hum. Genet. 70:935-942, 2002.
8. Morinaga T, Nakagawa N, Yasuda H, et al. Cloning and characterization of the gene encoding human osteoprotegerin/osteoclastogenesis-inhibitory factor. Eur J. Biochem 254, 685-691 (1998).
9. Elaine M. Dennison, Nigel K. Arden, Richard W. Keen, et al. Birthweiht, vitamin D receptor genotype and the programming of osteoporosis. Paediatric and Perinatal Epidemiology 2001, 15, 211-219.
10. Gennari L., Merlotti D., De Paola V., et al. Estrogen Receptor Gene Polymorphisms and the Genetics of Osteoporosis: A HuGE Review. Am J Epidemiol 2005; 161:307-320 the classification of fibromyalgia. Arthritis Rheum. 1990; 33:160-72.

The invention claimed is:

1. A method of prognosing an osteoporosis phenotype in a subject, which comprises:
    (I) determining in a biological sample from the subject the genotype of the subject at one or more positions of single nucleotide polymorphism, thereby obtaining outcomes for one or more single nucleotide polymorphism variables, and determining one or more clinical variables for the subject; and
    (II) using the variable outcomes obtained in (I) to prognose the phenotype; wherein:
    (a) the osteoporosis phenotype is a presence of one or more non-traumatic fractures in the wrist, hip or spine (WSH-fractures) and the variables for which outcomes are obtained in step (I) comprise the general BSTEP model variables in FIG. 9; and/or
    (b) the osteoporosis phenotype is a presence of one or more non-traumatic fractures in the wrist, hip or spine (WSH-fractures) and the variables for which outcomes are obtained in step (I) comprise the general FSTEP model variables in FIG. 9; and/or
    (c) the osteoporosis phenotype is a presence of one or more non-traumatic fractures in the wrist, hip or spine (WSH-fractures) and the variables for which outcomes are obtained In step (I) comprise the male BSTEP model variables in FIG. 9; and/or
    (d) the osteoporosis phenotype is a presence of one or more non-traumatic fractures in the wrist, hip or spine (WSH-fractures) and the variables for which outcomes are obtained in step (I) comprise the male FSTEP model variables In FIG. 9; and/or
    (e) the osteoporosis phenotype is a presence of one or more non-traumatic fractures in the wrist, hip or spine (WSH-fractures) and the variables for which outcomes are obtained in step (I) comprise the female BSTEP model variables in FIG. 9; and/or
    (f) the osteoporosis phenotype is a presence of one or more non-traumatic fractures in the wrist, hip or spine (WSH-fractures) and the variables for which outcomes are obtained in step (I) comprise the female FSTEP model variables in FIG. 9; and/or
    (g) the osteoporosis phenotype is presence of one or more non-traumatic vertebral fractures and the variables for which outcomes are obtained in step (I) comprise the male vertebral fractures variables or the female vertebral fractures variables in Table 5;
    and wherein
    (i) an outcome for an SNP variable is the identity of the nucleotide in the genomic DNA of the subject at the position of the single nucleotide polymorphism;

(ii) an outcome for the clinical variable AGE is age of the subject in years;
(iii) an outcome for the clinical variable MENOPAUSE AGE is the age in years of the onset of menopause in a female subject;
(iv) an outcome for the clinical variable MENARCHE AGE is the age in years of the onset of menarche in a female subject;
(v) an outcome for the clinical variable BMI is the body mass index of the subject.

2. A method of estimating an osteoporosis quantitative trait in a subject, which comprises:
(I) determining in a biological sample from a subject the genotype of the subject at one or more positions of single nucleotide polymorphism, thereby obtaining outcomes for one or more single nucleotide polymorphism variables, and determining one or more clinical variables for the subject; and
(II) using the variable outcomes obtained in (I) to estimate the trait;
wherein:
(a) the quantitative trait is lumbar spine bone mineral density (LSBMD) and the variables for which outcomes are obtained in step (I) comprise the male or female LSBMD variables in Table 5; and/or
(b) the quantitative trait is femoral neck bone mineral density (FNBMD) and the variables for which outcomes are obtained in step (I) comprise the male or female FNBMD variables in Table 5;
and wherein
(i) an outcome for an SNP variable is the identity of the nucleotide in the genomic DNA of the subject at the position of the single nucleotide polymorphism;
(ii) an outcome for the clinical variable AGE is age of the subject in years;
(iii) an outcome for the clinical variable MENOPAUSE AGE is the age in years of the onset of menopause in a female subject;
(iv) an outcome for the clinical variable MENARCHE AGE is the age in years of the onset of menarche in a female subject;
(v) an outcome for the clinical variable BMI is the body mass index of the subject.

3. A method according to claim 1 wherein in any of (a) to (g) the variables for which outcomes are obtained in step (I) consist of the SNP and clinical variables listed in FIG. 9 for the model or in Table 5 for the phenotype.

4. A method according to claim 1 wherein in step (II), only the outcomes obtained in step (I) are used to prognose the phenotype or estimate the trait.

5. A method according to claim 1 wherein obtaining outcomes for SNP variables comprises microarray analysis or sequencing.

6. A method according to claim 1 wherein obtaining outcomes for SNP variables comprises the use of one or more oligonucleotide probe pairs or probe sets listed in FIG. 2A, 2B or 2C.

7. A method according to claim 1 which comprises use of one or more oligonucleotide primer pairs listed in FIG. 3A, 3B or 3C.

8. A method according to claim 1 wherein step (II) comprises:
(i) inputting the outcomes determined in step (I) into a probability function or quantitative function thereby calculating a probability function value or a quantitative function value; and
(ii) where a probability function value is obtained, comparing the probability function value with probability function values calculated for individuals of known phenotype.

9. A method according to claim 1 wherein in any of (a) to (g) the variables for which outcomes are obtained consist of the SNP variables and clinical variables listed in FIG. 9 for the model or in Table 5 for the phenotype.

10. A method according to claim 1 comprising use of a probability function derived using the data in any of FIGS. 17A, 17B, 18A, 18B, 19A or 19B.

11. A method of selecting a suitable treatment for treating osteoporosis in a subject, the method comprising:
(a) prognosing an osteoporosis phenotype in the subject by a method according to claim 1; and
(b) selecting a treatment which is suitable for the determined osteoporosis phenotype or trait.

12. A method of treating osteoporosis in a subject comprising:
(a) prognosing an osteoporosis phenotype in the subject by a method according to claim 1; and
(b) administering to the subject a treatment which is suitable for the determined osteoporosis phenotype or trait.

* * * * *

UNITED STATES PATENT AND TRADEMARK OFFICE
CERTIFICATE OF CORRECTION

PATENT NO. : 8,296,073 B2  
APPLICATION NO. : 12/309162  
DATED : October 23, 2012  
INVENTOR(S) : Cadaval et al.

Page 1 of 1

It is certified that error appears in the above-identified patent and that said Letters Patent is hereby corrected as shown below:

In the Specification:

Column 13, line 29, "Table 1N1B" should read --Table 1A/1B--.

Column 40, line 13, "Table 1N1B" should read --Table 1A/1B--.

Signed and Sealed this
Twentieth Day of May, 2014

Michelle K. Lee
*Deputy Director of the United States Patent and Trademark Office*